US011078235B2

(12) United States Patent
Hazlehurst et al.

(10) Patent No.: US 11,078,235 B2
(45) Date of Patent: Aug. 3, 2021

(54) CYCLIC PEPTIDE CONJUGATES AND METHODS OF USE

(71) Applicants: H. Lee Moffitt Cancer Center And Research Institute, Inc., Tampa, FL (US); University of South Florida, Tampa, FL (US); The Scripps Research Institute, La Jolla, CA (US); Modulation Therapeutics, Tampa, FL (US)

(72) Inventors: Lori Hazlehurst, Morgantown, WV (US); Christoph Rader, Jupiter, FL (US); Xiuling Li, Jupiter, FL (US); Mark McLaughlin, Tampa, FL (US)

(73) Assignees: H. Lee Moffitt Cancer Center And Research Institute, Inc., Tampa, FL (US); The Scripps Research Institute, La Jolla, CA (US); University of South Florida, Tampa, FL (US)

( * ) Notice: Subject to any disclaimer, the term of this patent is extended or adjusted under 35 U.S.C. 154(b) by 0 days.

(21) Appl. No.: 16/025,382

(22) Filed: Jul. 2, 2018

(65) Prior Publication Data

US 2019/0092812 A1    Mar. 28, 2019

Related U.S. Application Data

(63) Continuation of application No. 15/024,928, filed as application No. PCT/US2014/057763 on Sep. 26, 2014, now Pat. No. 10,011,635.

(60) Provisional application No. 61/883,910, filed on Sep. 27, 2013.

(51) Int. Cl.
| | |
|---|---|
| C07K 7/06 | (2006.01) |
| C07K 7/08 | (2006.01) |
| C07K 14/705 | (2006.01) |
| C07K 1/00 | (2006.01) |
| A61K 38/00 | (2006.01) |

(52) U.S. Cl.
CPC ............ *C07K 7/06* (2013.01); *C07K 1/00* (2013.01); *C07K 7/08* (2013.01); *C07K 14/705* (2013.01); *C07K 14/70596* (2013.01); *A61K 38/00* (2013.01); *C07K 2319/21* (2013.01); *C07K 2319/30* (2013.01)

(58) Field of Classification Search
USPC ........................................................ 530/300
See application file for complete search history.

(56) References Cited

U.S. PATENT DOCUMENTS

| | | |
|---|---|---|
| 5,595,756 A | 1/1997 | Bally et al. |
| 5,767,071 A | 6/1998 | Palladino et al. |
| 5,770,565 A | 6/1998 | Cheng et al. |
| 5,817,750 A | 10/1998 | Ruoslahti et al. |
| 5,932,217 A | 8/1999 | Tuomanen et al. |
| 5,955,572 A | 9/1999 | Ruoslahti et al. |
| 6,034,056 A | 3/2000 | Dutta et al. |
| 6,034,057 A | 3/2000 | Dutta et al. |
| 6,096,707 A | 8/2000 | Heino et al. |
| 6,107,275 A | 8/2000 | Harbeson et al. |
| 6,235,711 B1 | 5/2001 | Dutta et al. |
| 6,713,604 B1 | 3/2004 | Kogan et al. |
| 6,849,712 B1 | 2/2005 | Mccarthy et al. |
| 6,933,314 B2 | 8/2005 | Artis et al. |
| 7,632,814 B2 | 12/2009 | Hazlehurst et al. |
| 8,227,434 B1 | 7/2012 | Dalton et al. |
| 8,853,149 B2 | 10/2014 | Hazlehurst et al. |
| 2003/0125243 A1 | 7/2003 | Liu et al. |
| 2004/0096906 A1 | 5/2004 | Lam et al. |
| 2004/0126379 A1 | 7/2004 | Adolf et al. |
| 2006/0019900 A1 | 1/2006 | Lam et al. |
| 2006/0041105 A1 | 2/2006 | Jiang et al. |
| 2007/0048325 A1 | 3/2007 | Van Epps et al. |
| 2008/0108552 A1 | 5/2008 | Hazlehurst et al. |
| 2009/0104116 A1 | 4/2009 | Zischinsky et al. |
| 2009/0169570 A1 | 7/2009 | Daelken et al. |
| 2009/0247549 A1 | 10/2009 | Frankel et al. |
| 2010/0104510 A1 | 4/2010 | Rader et al. |
| 2013/0171074 A1 | 7/2013 | Barbas et al. |
| 2014/0080762 A1 | 3/2014 | Hazlehurst et al. |
| 2014/0322227 A1 | 10/2014 | Hazlehurst et al. |

FOREIGN PATENT DOCUMENTS

| | | |
|---|---|---|
| WO | WO-2001/062776 | 8/2001 |
| WO | WO-2005/045430 | 5/2005 |
| WO | WO-2007/098575 | 9/2007 |
| WO | WO-2008/031064 | 3/2008 |
| WO | WO-2011/115688 | 9/2011 |
| WO | WO-2012/129335 | 9/2012 |
| WO | WO-2013/170066 | 11/2013 |

OTHER PUBLICATIONS

Gravanis, I. et al. "The changing world of cancer drug development: the regulatory bodies' perspective" *Chin. Clin. Oncol.*, 2014, 3(2):1-5.
Hait, W. "Anticancer drug development: the grand challenges" *Nature Reviews/Drug Discovery*, 2010, 9:253-254.
Merck Manual, "Cellular and Molecular Basis of Cancer", Nov. 7, 2012, pp. 1-5.
Neidle, S. (Ed.) "Failure Modes in the Discovery Process" in Cancer Drug Design and Discovery, Elsevier/Academic Press, 2008, pp. 427-431.

(Continued)

*Primary Examiner* — Christina Bradley
(74) *Attorney, Agent, or Firm* — Meunier Carlin & Curfman LLC

(57) ABSTRACT

The present invention concerns cyclic compounds, compositions comprising the cyclic compounds, linkers, a method of preparing a carrying agent:cyclic compound adduct, a method for treating disorders such as proliferation disorders (e.g., malignancies), bone deficiency diseases, and autoimmune diseases, and a method for suppressing the growth of, or inducing apoptosis in, cells (e.g., malignant cells).

3 Claims, 15 Drawing Sheets
Specification includes a Sequence Listing.

(56) References Cited

OTHER PUBLICATIONS

Sporn, M. and Nanjoo, S. "Chemoprevention of cancer" *Carcinogenesis*, 2000, 21(3):525-530.
Abe M et al., "Vicious cycle between myeloma cell binding to bone marrow stromal cells via VLA-4-V CAM-1 adhesion and macrophage inflammatory protein-Iα and MIP-Iβ production" Journal of Bone and Mineral Metabolism, 2009, 27(1):16-23.
Abram CL and Lowell CA, "The ins and outs of leukocyte integrin signaling" Annual Review of Immunology, 2009, 27:339-362.
Anderson KC et al., "Multiple Myeloma: New Insights and Therapeutic Approaches" Hematology, 2000, 147-165.
Aoudjit F, and Vuori K. Integrin signaling inhibits paclitaxel-induced apoptosis in breast cancer cells. *Oncogene*. 2001;20:4995-5004.
Astier A et al. The related adhesion focal tyrosine kinase differentially phosphorylates p130Cas and the Cas-like protein, p105HEF1. *J Biol Chem*. 1997;272:19719-19724.
Azab AK et al., "CXCR4 inhibitor AMD3100 disrupts the interaction of multiple myeloma cells with the bone marrow microenvironment and enhances their sensitivity to therapy" Blood, 2009, 113(18):4341-4351.
Baker DE, "Natalizumab: Overview of Its Pharmacology and Safety" Reviews in Gastroenterological Disorders, 2007, 7(1):38-46.
Banerjee D et al., "Novel aspects of resistance to drugs targeted to dihydrofolate reductase and thymidylate synthase" Biochimica et Biophysica Acta, 2002, 1587:164-173.
Bednarczyk JL et al., "Post-translational Processing of the Leukocyte Integrin α4β1" Journal of Biological Chemistry, 1992, 267(35):25274-25281.
Bertrand, RD et al., "Unusual behavior of Hexafluorobenzene and Benzene in the Aromatic Nuclear Magnetic Resonance Shift Effect" *Journal of the American Chemical Society*, 1970, 92(9):2702-9.
Bissell MJ and Radisky D, "Putting tumours in context" Nature Review / Cancer, 2001, 1(1):46-54.
Chen Q, et al. Integrin-mediated activation of MEK and mitogen-activated protein kinase is independent of Ras [corrected]. J Biol Chem. 1996;271:18122-18127.
Chorev, M and Goodman, M, "A Dozen Years of Retro-Inverso peptidomimetics" *American Chemical Society*, 1993, 26(5):266-73.
Cox D et al. "Integrins as therapeutic targets: lessons and opportunities" *Nature Rev. Drug Disc.*, 2010, 9:804-820.
Crimmins, MT and Zuercher, WJ, "Solid-Phase Synthesis of Carbocyclic Nucleosides" *Organic letters*, 2000, 2(8):1065-7.
Dalton WS. "The tumor microenvironment: focus on myeloma" *Cancer Treat Rev.*, 2003, 29(Suppl 1):11-19.
Damiano JS et al. Cell adhesion mediated drug resistance (CAM-DR): role of integrins and resistance to apoptosis in human myeloma cell lines. *Blood*. 1999;93:1658-1667.
Damiano JS et al. Cell adhesion-mediated drug resistance (CAM-DR) protects the K562 chronic myelogenous leukemia cell line from apoptosis induced by BCR/ABL inhibition, cytotoxic drugs, and gamma-irradiation. *Leukemia*. 2001;15:1232-1239.
De Bruyn et al., "The small GTPase Rap1 is Required for Mn2+- and Antibody-induced LFA-1- and VLA-4-mediated Cell Adhesion" Journal of Biological Chemistry, 2002, 277(33):29468-29476.
Deroock, IB et al., "Synthetic Peptides Inhibit Adhesion of Human Tumor Cells to Extracellular Matrix Proteins" *Cancer Research*, 2001, 61(8):3308-3313.
Dressman, BA et al., "Solid Phase Synthesis of Hydantoins Using a Carbamate Linker and a Novel Cyclization/Cleavage Step" *Tetrahedron Letters*, 1996, 37(7):937-40.
Epstein J and Yaccoby S, "Consequences of interactions between the bone marrow stroma and myeloma" The Hematology Journal, 2003, 4(5):310-314.
Favre, M et al., "Structural Mimicry of Canonical Conformations in Antibody Hypervariable Loops Using Cyclic Peptides Containing a Heterochiral Diproline Template" *Journal of the American Chemical Society*, 1999, 121(12):2679-2685.

Ficht, S et al., "Solid-Phase Synthesis of Peptide and Glycopeptide Thioesters through Side-Chain-Anchoring Strategies" *Chemistry—A European Journal*, 2008, 14(12):3620-3629.
Fletcher, MD and Campbell, MM, "Partially Modified Retro-Inverso Peptides: Development, Synthesis and Conformational Behavior" *Chemical Reviews* (Washington, D. C.), 1998, 98(2):763-795.
Gatenby RA et al., "Adaptive Therapy" Cancer Research, 2009, 69(11):4894-4903.
Gebhard A et al. "Validation of CD44 as a binding partner of the novel peptide HYD1 in multiple myeloma" presented at Moffitt Cancer Symposium in Tampa, FL on May 10, 2012, poster and abstract (Abstract No. B-68).
Gebhard, A. et al. "MTI-101 (Cyclized HYD1) Binds a CD44 Containing Complex and Induces Necrotic Cell Death in Multiple Myeloma" *Mol. Cancer Ther.*, 2013, 12(11):2446-2458.
Gottesman MM and Ling V, "The molecular basis of multidrug resistance in cancer: The early years of P-glycoprotein research" FEBS Letters, 2006, 580(4):998-1009.
Gutman D et al., "Acquisition of a Multidrug Resistant Phenotype with a Proteasome Inhibitor in Multiple Myeloma" Leukemia, 2009, 23(11):2181-2183.
Hannigan GE et al. Regulation of cell adhesion and anchorage-dependent growth by a new beta 1-integrin-linked protein kinase. Nature. 1996;379:91-96.
Hazlehurst L et al. "Comparison of aza-anthracenedione-induced DNA damage and cytotoxicity in experimental tumor cells" *Biochem Pharmacol.*, 1995, 50(7):1087-1094.
Hazlehurst L and Dalton WS "Mechanisms associated with cell adhesion mediated drug resistance (CAM-DR) in hematopoietic malignancies" *Cancer Metastasis Rev.*, 2001, 20:43-50.
Hazlehurst LA et al. Adhesion to fibronectin via beta1 integrins regulates p27kip1 levels and contributes to cell adhesion mediated drug resistance (CAM-DR). *Oncogene*. 2000;19:4319-4327.
Hazlehurst LA et al. Cell adhesion to fibronectin (CAM-DR) influences acquired mitoxantrone resistance in U937 cells. *Cancer Res*. 2006;66:2338-2345.
Hazlehurst LA et al. Genotypic and phenotypic comparisons of de novo and acquired melphalan resistance in an isogenic multiple myeloma cell line model. *Cancer* Res. 2003;63:7900-7906.
Hazlehurst LA et al. Reduction in drug-induced DNA double-strand breaks associated with beta1 integrin-mediated adhesion correlates with drug resistance in U937 cells. *Blood*. 2001;98:1897-1903.
Hazlehurst LA et al. β1 integrin adhesion increases Bim protein degradation and confers drug resistance in leukemia cells *British Journal Haematology*. 2006.
Hazlehurst LA et al., "Multiple Mechanisms Confer Drug Resistance to Mitoxantrone in the Human 8226 Myeloma Cell Line" Cancer Research, 1999, 59(5):1021-1028.
Hazlehurst LA et al., "Role of the tumor microenvironment in mediating de novo resistance to drugs and physiological mediators of cell death" Oncogene, 2003, 22(47):7396-7402.
Hazlehurst LA, Targeting beta1 Integrins in Multiple Myeloma. Presentation at Advancing Myeloma Therapy: Translating Laboratory Concepts into Clinical Reality Symposium held in conjunction with the XIth International Myeloma Symposium. Jun. 25, 2007.
His, S et al., "Solid phase synthesis of amides by the Beckmann rearrangement of ketoxime carbonates" *Tetrahedron Letters*, 2003, 44(47):8581-8584.
Hofer, T. et al. "Molecularly Defined Antibody Conjugation through a Selenocysteine Interface" *Biochemistry*, 2009, 48:12047-12057.
Hofer, T. et al. "An engineered selenocysteine defines a unique class of antibody derivatives" *Proceedings of the National Academy of Sciences*, 2008, 105(34):12451-12456.
Hughes, RM and Waters, ML, "Influence of N-Methylation on a Cation-pi Interaction Produces a Remarkably Stable beta-Hairpin Peptide" *Journal of the American Chemical Society*, 2005, 127(18):6518-6519.
Hutchinson, EG et al., "Determinants of strand register in antiparallel beta-sheets of proteins" *Protein Science*, 1998, 7(11):2287-2300.
Li, X. et al., "Antibody conjugation via one and two C-terminal selenocysteines" *Methods*, 2014, 65:133-138.
Li ZW, Dalton WS, "Tumor microenvironment and drug resistance in hematologic malignancies" *Blood Rev.* 2006, 20(6):333-342.

(56) References Cited

OTHER PUBLICATIONS

Jain P. et al. "Cyclic β-hairpin peptidomimetics targeting protein-protein interactions" presented at Moffitt Cancer Symposium in Tampa, FL on May 10, 2012, poster and abstract (Abstract No. B-171).
Jemal A et al., "Cancer Statistics, 2010" CA: A Cancer Journal for Clinicians, 2010, 60(5):277-300.
Jin, L. and Harrison, S. "Crystal structure of human calcineurin complexed with cyclosporin A and human cyclophilin" PNAS, 2002, 99(21):13522-13526.
Khleif SN et al., "AACR-FDA-NCI Cancer Biomarkers Collaborative Consensus Report: Advancing the Use of Biomarkers in Cancer Drug Development" Clinical Cancer Research, 2010, 16(13):3299-3318.
Kim, J-H. et al. "Combined use of tamoxifen, cyclosporin A, and verapamil for modulating multidrug resistance in human hepatocellular carcinoma cell lines" Yonsei Medical Journal, 1993, 34(1):35-44.
King WG et al. Phosphatidylinositol 3-kinase is required for integrin-stimulated AKT and Raf-1/mitogen-activated protein kinase pathway activation. Mol Cell Biol. 1997;17:4406-4418.
Kuwahara, M et al., "Hybridization between Oxy-Peptide Nucleic Acids and DNAs: Dependence of Hybrid Stabilities on the Chain-Lengths, Types of Base Pairs, and the Chain Directions" Journal of the American Chemical Society, 2001, 123(20):4653-4658.
Kuwahara, M et al., "Synthesis of delta-Amino Acids with an Ether Linkage in the Main Chain and Nucleobases on the Side Chain as Monomer Units for Oxy-peptide Nucleic Acids" Tetrahedron, 1999, 55(33):10067-10078.
Kyle RA and Rajkumar SV, "Multiple Myeloma" New England Journal of Medicine, 2004, 351(18):1860-1873.
Luo BH et al., "Structural basis of integrin regulation and signaling" Annual Review of Immunology, 2007, 25:619-647.
Lwin T et al. Cell adhesion induces p27Kip1-associated cell-cycle arrest through down-regulation of the SCFSkp2 ubiquitin ligase pathway in mantle cell and other non-Hodgkin's B-cell lymphomas. Blood. 2007.
Mahon FX, et al., "Selection and Characterization of BCR-ABL positive cell lines with differential sensitivity to the tyrosine kinase inhibitor STI571: diverse mechanisms of resistance" Blood, 2000, 96(3):1070-1079.
Matsunago T et al., "Interaction between leukemic-cell VLA-4 and stromal fibronectin is a decisive factor for minimal residual disease of acute myelogenous leukemia" Nature Medicine, 2003, 9(9):1158-1165.
McMillin DW et al., "Tumor cell-specific bioluminescence platform to identify stroma-induced changes to anticancer drug activity" Nature Medicine, 2010, 16(4):483-489.
Meester, WJN et al., "Synthesis of Homoallylic Amines via N-Acyliminium Ion Reactions on Solid Support" Tetrahedron Letters, 1999, 40(8):1601-1604.
Morgan SE et al., "Differences in mutant p53 protein stability and functional activity in teniposide-sensitive and -resistant human leukemic CEM cells" Oncogene, 2000, 19(43):5010-5019.
Mori Y et al., "Anti-α4 integrin antibody suppresses the development of multiple myeloma and associated osteoclastic osteolysis" Blood, 2004, 104(7):2149-2154.
Morin PJ, "Drug resistance and the microenvironment: nature and nurture" Drug Resistance Updates, 2003, 6(4):169-172.
Murray P "cHYD1 solution phase synthesis optimization and the development of a novel human growth hormone antagonist and agonist" Graduate School Theses and Dissertaions, University of South Florida, Apr. 4, 2012.
Nair RR et al., "HYD1-induced increase in ROS leads to autophagy and necrotic cell death in multiple myeloma cells" Molecular Cancer Therapeutics. 2009, 8(8):2441-51.
Nair RR et al., "The bone marrow microenvironment as a sanctuary for minimal residual disease in CML" Biochemical Pharmacology, 2010, 80(5):602-612.
Nair, DT et al., "Mimicry of Native Peptide Antigens by the Corresponding Retro-Inverso Analogs is Dependent on Their Intrinsic Structure and Interaction Propensities" The Journal of Immunology, 2003, 170(3):1362-1373.
Nefedova Y et al. Bone marrow stromal-derived soluble factors and direct cell contact contribute to de novo drug resistance of myeloma cells by distinct mechanisms. Leukemia. 2003;17:1175-1182.
Nefedova Y et al., "Inhibition of Notch signaling induces apoptosis of myeloma cells and enhances sensitivity to chemotherapy" Blood, 2008, 111(4):2220-2229.
Olson DL et al., "Anti-α4 integrin monoclonal antibody inhibits multiple myeloma growth in a murine model" Molecular Cancer Therapeutics, 2005, 4(1):91-99.
Palioura, S. et al. "The human SepSecS-tRNASec complex reveals the mechanism of selenocysteine formation" Science, 2009, 325(5938):321-325.
Park, KH and Cox, LJ, "Solid-phase synthesis of 1,2,4-triazolidine-3,5-diones" Tetrahedron Letters, 2002, 43(21):3899-3901.
Pennington, ME et al., "The use of a combinatorial library method to isolate human tumor cell adhesion peptides" Molecular Diversity, 1996, 2(1/2):19-28.
Rabinowitz, M et al., "Solid-Phase/ Solution-Phase Combinatorial Synthesis of Neuroimmunophilin Ligands" Bioorganic & Medicinal Chemistry Letters. 2000, 10(10):1007-1010.
Rader, C. "Chemically programmed antibodies" Trends Biotechnol., 2014, 32:186-197.
Robey RW et al., "ABCG2: determining its relevance in clinical drug resistance" Cancer and Metastasis Reviews, 2007, 26(1):39-57.
Roopenian, D.C. and Akilesh, S. "FcRn: The neonatal Fc receptor comes of age" Nat Rev Immunol., 2007, 7:715-725.
Schaller MD and Parsons JT. pp125FAK-dependent tyrosine phosphorylation of paxillin creates a high-affinity binding site for Crk. Mol Cell Biol. 1995;15:2635-2645.
Schlaepfer DD et al. Integrin-mediated signal transduction linked to Ras pathway by GRB2 binding to focal adhesion kinase. Nature. 1994;372:786-791.
Sethi T et al. Extracellular matrix proteins protect small cell lung cancer cells against apoptosis: a mechanism for small cell lung cancer growth and drug resistance in vivo. Nat Med. 1999;5:662-668.
Shibata, K et al., "G-CSF receptor-binding cyclic peptides designed with artificial amino-acid links" Biochemical and Biophysical Research Communications, 2006, 341(2):483-488.
Sroka T et al., "Synthetic D-amino acid peptide inhibits tumor cell motility on laminin-5" Carcinogenesis, 2006, 27(9):1748-57.
Sroka T et al., "The Minimum Element of a Synthetic Peptide Required to Block Prostate Tumor Cell Migration" Cancer Biological Therapies, 2006, 5(11):1556-62.
Taylor, EM et al., "Retro-Inverso Prosaptide Peptides Retain Bioactivity, Are Stable In Vivo, and Are Blood-Brain Barrier Permeable" The Journal of Pharmacological and Experimental Therapeutics, 2000, 295(1):190-194.
Teixido J et al., "Functional and Structural Analysis of VLA-4 Integrin α4 Subunit Cleavage" Journal of Biological Chemistry, 1992, 267(3):1786-1791.
Thomson, SA et al., "Fmoc Mediated Synthesis of Peptide Nucleic Acids" Tetrahedron, 1995, 51(22):6179-94.
Tian E et al., "The Role of the Wnt-Signaling Antagonist DKKI in the Development of Osteolytic Lesions in Multiple Myeloma" New England Journal of Medicine, 2003, 349(26):2483-2494.
Tolentino JH et al. "HM-27 targets AML cells via cell death by necrosis" presented at Moffitt Cancer Symposium in Tampa, FL on May 10, 2012, Abstract No. B-159).
Van Riet I et al. Expression of cytoadhesion molecules (CD56, CD54, CD18 and CD29) by myeloma plasma cells. Br J Haematol. 1991;79:421-427.
Wang, C-C and Li, W-R, "Traceless Solid-Phase Synthesis of Substituted Benzimidazolones" Journal of Combinatorial Chemistry 2004, 6(6):899-902.

(56) References Cited

OTHER PUBLICATIONS

Wang, P and Miranda, LP, "Fmoc-Protein Synthesis: Preparation of Peptide Thioesters Using a Side-Chain Anchoring Strategy" *International Journal of Peptide Research and Therapeutics*, 2005, 11(2):117-123.

Wishart, DS et al., "Relationship Between Nuclear Magnetic Resonance Chemical Shift and Protein Secondary Structure" *Journal of Molecular Biology*, 1991, 222(2):311-33.

Wishart, DS et al., "The Chemical Shift Index: A Fast and Simple Method for the Assignment of Protein Secondary Structure Through NMR Spectroscopy" *Biochemistry*, 1992, 31(6):1647-51.

Yaccoby S et al. Primary myeloma cells growing in SCID-hu mice: a model for studying the biology and treatment of myeloma and its manifestations. Blood. 1998;92:2908-2913.

Yaccoby S et al., "Cancer and the Microenvironment: Myeloma-Osteoclast Interactions as a Model" Cancer Research, 2004, 64(6):2016-2023.

Yamamoto, Y et al., "NMR study of *Galeorhinus japonicus* myoglobin: Proton-NMR study of molecular structure of the heme cavity" *European Journal of Biochemistry*, 1991, 198(2):299-306.

Zhou, P et al., "Geometric characteristics of hydrogen bonds involving sulfur atoms in proteins" Proteins, 2009, 76:151-163.

Zhu K et al. Farnesyltransferase inhibitor R115777 (Zarnestra, Tipifarnib) synergizes with paclitaxel to induce apoptosis and mitotic arrest and to inhibit tumor growth of multiple myeloma cells. Blood. 2005;105:4759-4766.

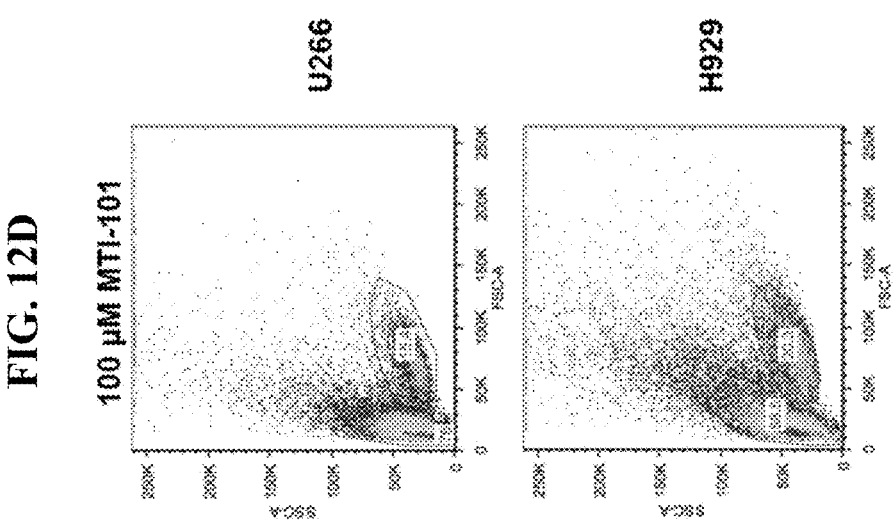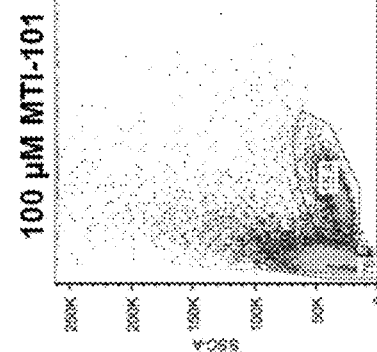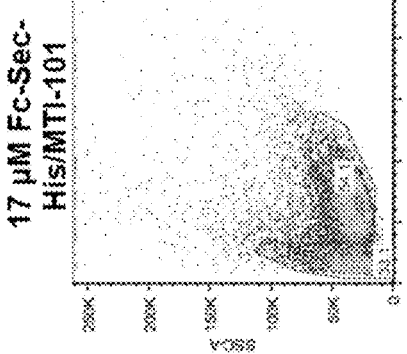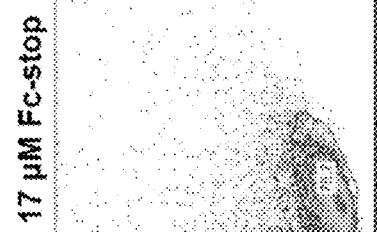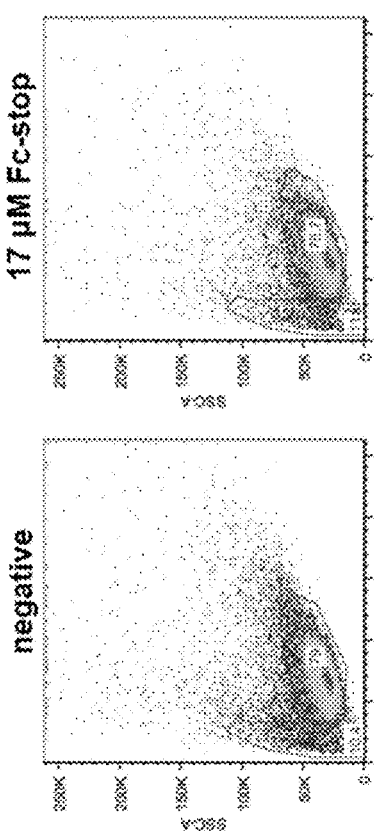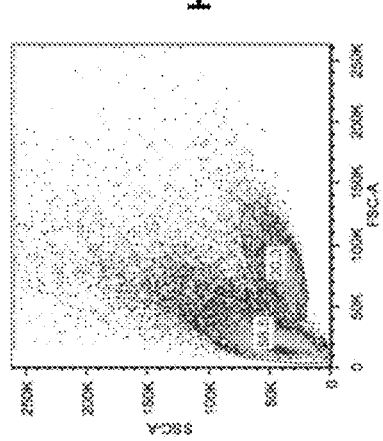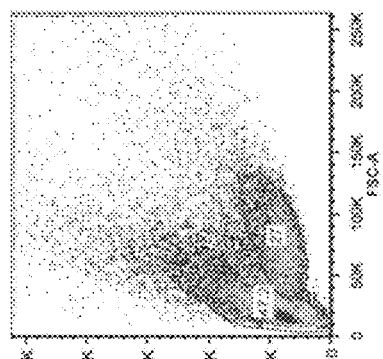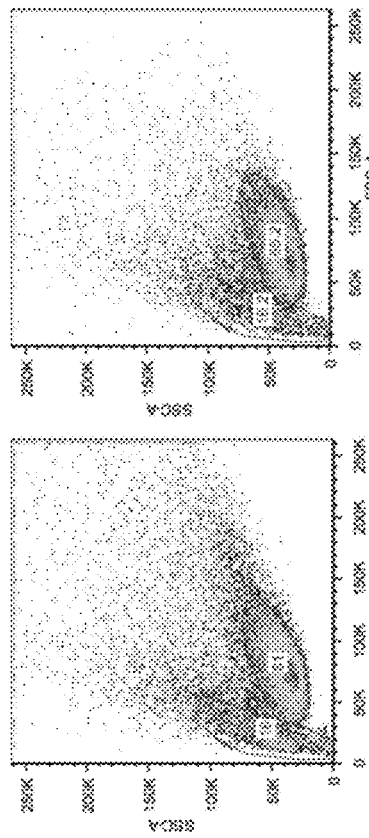

FIG. 14A
36 µM scFv-Fc-
stop
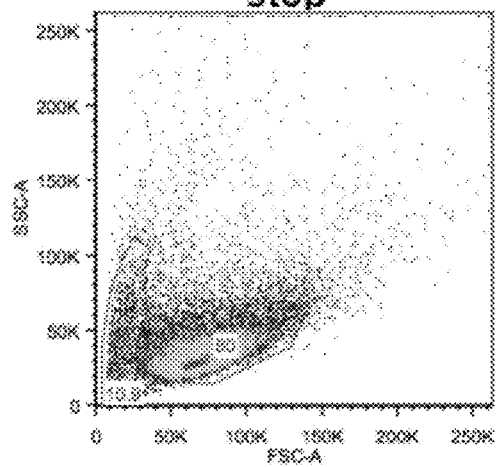
FIG. 14B
36 µM scFv-Fc-
Sec-His/MTI-101
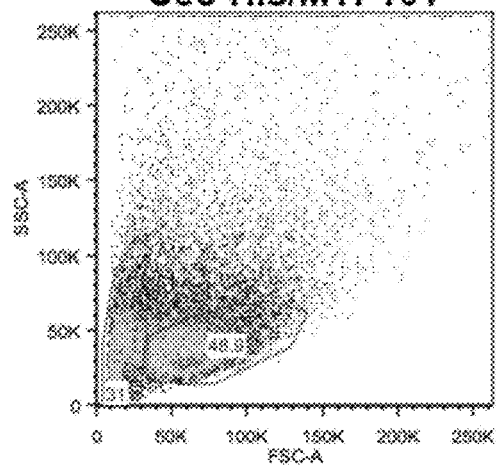
U266
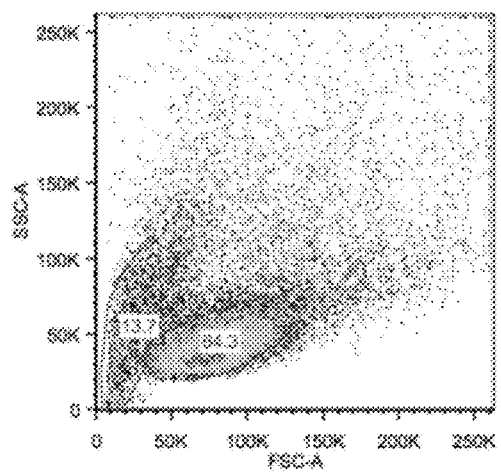
FIG. 14C
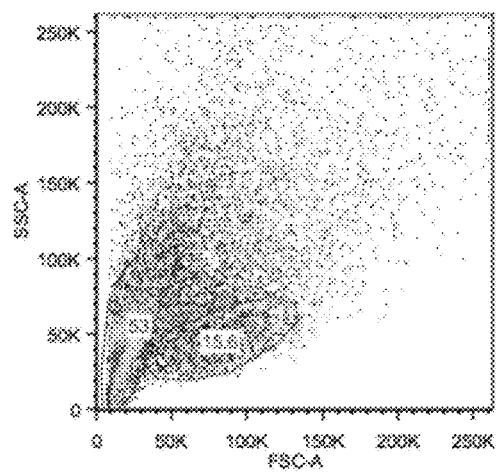
FIG. 14D
H929

SEQUENCE LISTING

```
<160> NUMBER OF SEQ ID NOS: 230

<210> SEQ ID NO 1
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 1

Lys Leu Gln Leu Lys
1               5

<210> SEQ ID NO 2
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 2

Gln Leu Lys Leu Lys
1               5

<210> SEQ ID NO 3
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 3

Lys Gln Lys Leu Lys
1               5

<210> SEQ ID NO 4
<211> LENGTH: 5
<212> TYPE: PRT
<213> ORGANISM: Artificial sequence
<220> FEATURE:
<223> OTHER INFORMATION: amino acid non-recognition sequence
<220> FEATURE:
```

```
<221> NAME/KEY: MISC_FEATURE
<222> LOCATION: (2)..(2)
<223> OTHER INFORMATION: Xaa = sarcosine
<220> FEATURE:
<221> NAME/KEY: MISC_FEATURE
<222> LOCATION: (4)..(4)
<223> OTHER INFORMATION: Xaa = sarcosine

<400> SEQUENCE: 4

Lys Xaa Lys Xaa Lys
1               5

<210> SEQ ID NO 5
<211> LENGTH: 5
<212> TYPE: PRT
<213> ORGANISM: Artificial sequence
<220> FEATURE:
<223> OTHER INFORMATION: amino acid non-recognition sequence

<400> SEQUENCE: 5

Glu Leu Lys Leu Lys
1               5

<210> SEQ ID NO 6
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 6

Trp Ala Val Ala Trp
1               5

<210> SEQ ID NO 7
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 7

Trp Ala Val Ala Ala
1               5

<210> SEQ ID NO 8
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 8

Trp Ala Val Ala Met
1               5

<210> SEQ ID NO 9
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 9
```

Trp Ala Val Ala Xaa
1               5

<210> SEQ ID NO 10
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 10

Trp Ala Val Val Xaa
1               5

<210> SEQ ID NO 11
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 11

Trp Ala Val Ser Xaa
1               5

<210> SEQ ID NO 12
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 12

Trp Ala Ala Ala Trp
1               5

<210> SEQ ID NO 13
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 13

Trp Ala Ala Ala Ala
1               5

<210> SEQ ID NO 14
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 14

Trp Ala Ala Ala Met
1               5

<210> SEQ ID NO 15
<211> LENGTH: 5

```
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 15

Trp Ala Ala Ala Xaa
1               5

<210> SEQ ID NO 16
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 16

Trp Ala Ala Val Trp
1               5

<210> SEQ ID NO 17
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 17

Trp Ala Ala Val Ala
1               5

<210> SEQ ID NO 18
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 18

Trp Ala Ala Val Met
1               5

<210> SEQ ID NO 19
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 19

Trp Ala Ala Val Xaa
1               5

<210> SEQ ID NO 20
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
```

```
<222> LOCATION: (5)..(5)
<223> OTHER INFORMATION: Xaa = norleucine

<400> SEQUENCE: 20

Trp Ala Ala Ser Xaa
1               5

<210> SEQ ID NO 21
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 21

Trp Val Val Ala Trp
1               5

<210> SEQ ID NO 22
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 22

Trp Val Val Ala Ala
1               5

<210> SEQ ID NO 23
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 23

Trp Val Val Ala Met
1               5

<210> SEQ ID NO 24
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 24

Trp Val Val Ala Xaa
1               5

<210> SEQ ID NO 25
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 25

Trp Val Val Val Trp
1               5

<210> SEQ ID NO 26
```

```
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 26

Trp Val Val Val Ala
1               5

<210> SEQ ID NO 27
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 27

Trp Val Val Val Met
1               5

<210> SEQ ID NO 28
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 28

Trp Val Val Val Xaa
1               5

<210> SEQ ID NO 29
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 29

Trp Val Val Ser Xaa
1               5

<210> SEQ ID NO 30
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 30

Trp Val Ala Ala Xaa
1               5

<210> SEQ ID NO 31
<211> LENGTH: 5
<212> TYPE: PRT
```

```
<213> ORGANISM: Artificial sequence
<220> FEATURE:
<223> OTHER INFORMATION: amino acid recognition sequence

<400> SEQUENCE: 31

Trp Val Ala Val Trp
1               5

<210> SEQ ID NO 32
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 32

Trp Val Ala Val Ala
1               5

<210> SEQ ID NO 33
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 33

Trp Val Ala Val Met
1               5

<210> SEQ ID NO 34
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 34

Trp Val Ala Val Xaa
1               5

<210> SEQ ID NO 35
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 35

Trp Val Ala Ser Xaa
1               5

<210> SEQ ID NO 36
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 36
```

Trp Ser Val Ala Trp
1               5

<210> SEQ ID NO 37
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 37

Trp Ser Val Ala Ala
1               5

<210> SEQ ID NO 38
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 38

Trp Ser Val Ala Met
1               5

<210> SEQ ID NO 39
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 39

Trp Ser Val Ala Xaa
1               5

<210> SEQ ID NO 40
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 40

Trp Ser Val Val Trp
1               5

<210> SEQ ID NO 41
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 41

Trp Ser Val Val Ala
1               5

<210> SEQ ID NO 42
<211> LENGTH: 5
<212> TYPE: PRT
<213> ORGANISM: Artificial sequence
<220> FEATURE:
<223> OTHER INFORMATION: amino acid recognition sequence

```
<400> SEQUENCE: 42

Trp Ser Val Val Met
1               5

<210> SEQ ID NO 43
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 43

Trp Ser Val Val Xaa
1               5

<210> SEQ ID NO 44
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 44

Trp Ser Val Ser Trp
1               5

<210> SEQ ID NO 45
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 45

Trp Ser Val Ser Ala
1               5

<210> SEQ ID NO 46
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 46

Trp Ser Val Ser Met
1               5

<210> SEQ ID NO 47
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 47

Trp Ser Val Ser Xaa
1               5
```

<210> SEQ ID NO 48
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 48

Trp Ser Ala Ala Trp
1               5

<210> SEQ ID NO 49
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 49

Trp Ser Ala Ala Ala
1               5

<210> SEQ ID NO 50
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 50

Trp Ser Ala Ala Met
1               5

<210> SEQ ID NO 51
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 51

Trp Ser Ala Ala Xaa
1               5

<210> SEQ ID NO 52
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 52

Trp Ser Ala Val Trp
1               5

<210> SEQ ID NO 53
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 53

Trp Ser Ala Val Ala
1               5

<210> SEQ ID NO 54
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 54

Trp Ser Ala Val Met
1               5

<210> SEQ ID NO 55
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 55

Trp Ser Ala Val Xaa
1               5

<210> SEQ ID NO 56
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 56

Trp Ser Ala Ser Trp
1               5

<210> SEQ ID NO 57
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 57

Trp Ser Ala Ser Ala
1               5

<210> SEQ ID NO 58
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 58

Trp Ser Ala Ser Met
1               5

<210> SEQ ID NO 59
<211> LENGTH: 5
<212> TYPE: PRT
<213> ORGANISM: Artificial sequence
<220> FEATURE:
<223> OTHER INFORMATION: amino acid recognition sequence

```
<220> FEATURE:
<221> NAME/KEY: MISC_FEATURE
<222> LOCATION: (5)..(5)
<223> OTHER INFORMATION: Xaa = norleucine

<400> SEQUENCE: 59

Trp Ser Ala Ser Xaa
1               5

<210> SEQ ID NO 60
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 60

Trp Tyr Val Ala Trp
1               5

<210> SEQ ID NO 61
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 61

Trp Tyr Val Ala Ala
1               5

<210> SEQ ID NO 62
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 62

Trp Tyr Val Ala Met
1               5

<210> SEQ ID NO 63
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 63

Trp Tyr Val Ala Xaa
1               5

<210> SEQ ID NO 64
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 64

Trp Tyr Val Val Trp
1               5
```

```
<210> SEQ ID NO 65
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 65

Trp Tyr Val Val Ala
1               5

<210> SEQ ID NO 66
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 66

Trp Tyr Val Val Met
1               5

<210> SEQ ID NO 67
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 67

Trp Tyr Val Val Xaa
1               5

<210> SEQ ID NO 68
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 68

Trp Tyr Val Ser Trp
1               5

<210> SEQ ID NO 69
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 69

Trp Tyr Val Ser Ala
1               5

<210> SEQ ID NO 70
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 70
```

Trp Tyr Val Ser Met
1               5

<210> SEQ ID NO 71
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 71

Trp Tyr Val Ser Xaa
1               5

<210> SEQ ID NO 72
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 72

Trp Tyr Ala Ala Trp
1               5

<210> SEQ ID NO 73
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 73

Trp Tyr Ala Ala Ala
1               5

<210> SEQ ID NO 74
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 74

Trp Tyr Ala Ala Met
1               5

<210> SEQ ID NO 75
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 75

Trp Tyr Ala Ala Xaa
1               5

<210> SEQ ID NO 76
<211> LENGTH: 5

```
<212> TYPE: PRT
<213> ORGANISM: Artificial sequence
<220> FEATURE:
<223> OTHER INFORMATION: amino acid recognition sequence

<400> SEQUENCE: 76

Trp Tyr Ala Val Trp
1               5

<210> SEQ ID NO 77
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 77

Trp Tyr Ala Val Ala
1               5

<210> SEQ ID NO 78
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 78

Trp Tyr Ala Val Met
1               5

<210> SEQ ID NO 79
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 79

Trp Tyr Ala Val Xaa
1               5

<210> SEQ ID NO 80
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 80

Trp Tyr Ala Ser Trp
1               5

<210> SEQ ID NO 81
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 81

Trp Tyr Ala Ser Ala
1               5
```

```
<210> SEQ ID NO 82
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 82

Trp Tyr Ala Ser Met
1               5

<210> SEQ ID NO 83
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 83

Trp Tyr Ala Ser Xaa
1               5

<210> SEQ ID NO 84
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 84

Ala Ala Val Ala Ala
1               5

<210> SEQ ID NO 85
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 85

Ala Ala Val Ala Met
1               5

<210> SEQ ID NO 86
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 86

Ala Ala Val Ala Xaa
1               5

<210> SEQ ID NO 87
<211> LENGTH: 5
<212> TYPE: PRT
<213> ORGANISM: Artificial sequence
<220> FEATURE:
```

```
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 87

Ala Ala Val Val Xaa
1               5

<210> SEQ ID NO 88
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 88

Ala Ala Val Ser Xaa
1               5

<210> SEQ ID NO 89
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 89

Ala Ala Ala Ala Ala
1               5

<210> SEQ ID NO 90
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 90

Ala Ala Ala Ala Met
1               5

<210> SEQ ID NO 91
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 91

Ala Ala Ala Ala Xaa
1               5

<210> SEQ ID NO 92
<211> LENGTH: 5
<212> TYPE: PRT
<213> ORGANISM: Artificial sequence
<220> FEATURE:
<223> OTHER INFORMATION: amino acid recognition sequence
```

```
<400> SEQUENCE: 92

Ala Ala Ala Val Trp
1               5

<210> SEQ ID NO 93
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 93

Ala Ala Ala Val Ala
1               5

<210> SEQ ID NO 94
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 94

Ala Ala Ala Val Met
1               5

<210> SEQ ID NO 95
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 95

Ala Ala Ala Val Xaa
1               5

<210> SEQ ID NO 96
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 96

Ala Ala Ala Ser Met
1               5

<210> SEQ ID NO 97
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 97

Ala Ala Ala Ser Xaa
1               5
```

```
<210> SEQ ID NO 98
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 98

Ala Val Val Ala Trp
1               5

<210> SEQ ID NO 99
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 99

Ala Val Val Ala Ala
1               5

<210> SEQ ID NO 100
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 100

Ala Val Val Ala Met
1               5

<210> SEQ ID NO 101
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 101

Ala Val Val Ala Xaa
1               5

<210> SEQ ID NO 102
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 102

Ala Val Val Val Ala
1               5

<210> SEQ ID NO 103
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 103

Ala Val Val Val Met
```

<210> SEQ ID NO 104
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 104

Ala Val Val Val Xaa
1               5

<210> SEQ ID NO 105
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 105

Ala Val Val Ser Xaa
1               5

<210> SEQ ID NO 106
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 106

Ala Val Ala Ala Trp
1               5

<210> SEQ ID NO 107
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 107

Ala Val Ala Ala Met
1               5

<210> SEQ ID NO 108
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 108

Ala Val Ala Ala Xaa
1               5

```
<210> SEQ ID NO 109
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 109

Ala Val Ala Val Ala
1               5

<210> SEQ ID NO 110
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 110

Ala Val Ala Val Met
1               5

<210> SEQ ID NO 111
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 111

Ala Val Ala Val Xaa
1               5

<210> SEQ ID NO 112
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 112

Ala Val Ala Ser Xaa
1               5

<210> SEQ ID NO 113
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 113

Ala Ser Val Ala Trp
1               5

<210> SEQ ID NO 114
<211> LENGTH: 5
<212> TYPE: PRT
<213> ORGANISM: Artificial sequence
<220> FEATURE:
```

<223> OTHER INFORMATION: amino acid recognition sequence

<400> SEQUENCE: 114

Ala Ser Val Ala Ala
1               5

<210> SEQ ID NO 115
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 115

Ala Ser Val Ala Met
1               5

<210> SEQ ID NO 116
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 116

Ala Ser Val Ala Xaa
1               5

<210> SEQ ID NO 117
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 117

Ala Ser Val Val Trp
1               5

<210> SEQ ID NO 118
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 118

Ala Ser Val Val Ala
1               5

<210> SEQ ID NO 119
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 119

Ala Ser Val Val Met
1               5

<210> SEQ ID NO 120
<211> LENGTH: 5

```
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 120

Ala Ser Val Val Xaa
1               5

<210> SEQ ID NO 121
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 121

Ala Ser Val Ser Ala
1               5

<210> SEQ ID NO 122
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 122

Ala Ser Val Ser Met
1               5

<210> SEQ ID NO 123
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 123

Ala Ser Val Ser Xaa
1               5

<210> SEQ ID NO 124
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 124

Ala Ser Ala Ala Trp
1               5

<210> SEQ ID NO 125
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 125
```

Ala Ser Ala Ala Ala
1               5

<210> SEQ ID NO 126
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 126

Ala Ser Ala Ala Met
1               5

<210> SEQ ID NO 127
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 127

Ala Ser Ala Ala Xaa
1               5

<210> SEQ ID NO 128
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 128

Ala Ser Ala Val Trp
1               5

<210> SEQ ID NO 129
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 129

Ala Ser Ala Val Ala
1               5

<210> SEQ ID NO 130
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 130

Ala Ser Ala Val Met
1               5

<210> SEQ ID NO 131
<211> LENGTH: 5
<212> TYPE: PRT
<213> ORGANISM: Artificial sequence
<220> FEATURE:

```
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 131

Ala Ser Ala Val Xaa
1               5

<210> SEQ ID NO 132
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 132

Ala Ser Ala Ser Ala
1               5

<210> SEQ ID NO 133
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 133

Ala Ser Ala Ser Met
1               5

<210> SEQ ID NO 134
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 134

Ala Ser Ala Ser Xaa
1               5

<210> SEQ ID NO 135
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 135

Ala Tyr Val Ala Trp
1               5

<210> SEQ ID NO 136
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 136

Ala Tyr Val Ala Ala
1               5
```

```
<210> SEQ ID NO 137
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 137

Ala Tyr Val Ala Met
1               5

<210> SEQ ID NO 138
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 138

Ala Tyr Val Ala Xaa
1               5

<210> SEQ ID NO 139
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 139

Ala Tyr Val Val Trp
1               5

<210> SEQ ID NO 140
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 140

Ala Tyr Val Val Ala
1               5

<210> SEQ ID NO 141
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 141

Ala Tyr Val Val Met
1               5

<210> SEQ ID NO 142
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
```

```
<222> LOCATION: (5)..(5)
<223> OTHER INFORMATION: Xaa = norleucine

<400> SEQUENCE: 142

Ala Tyr Val Val Xaa
1               5

<210> SEQ ID NO 143
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 143

Ala Tyr Val Ser Trp
1               5

<210> SEQ ID NO 144
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 144

Ala Tyr Val Ser Ala
1               5

<210> SEQ ID NO 145
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 145

Ala Tyr Val Ser Met
1               5

<210> SEQ ID NO 146
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 146

Ala Tyr Val Ser Xaa
1               5

<210> SEQ ID NO 147
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 147

Ala Tyr Ala Ala Trp
1               5

<210> SEQ ID NO 148
```

```
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 148

Ala Tyr Ala Ala Ala
1               5

<210> SEQ ID NO 149
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 149

Ala Tyr Ala Ala Met
1               5

<210> SEQ ID NO 150
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 150

Ala Tyr Ala Ala Xaa
1               5

<210> SEQ ID NO 151
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 151

Ala Tyr Ala Val Trp
1               5

<210> SEQ ID NO 152
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 152

Ala Tyr Ala Val Ala
1               5

<210> SEQ ID NO 153
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 153

Ala Tyr Ala Val Met
1               5
```

```
<210> SEQ ID NO 154
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 154

Ala Tyr Ala Val Xaa
1               5

<210> SEQ ID NO 155
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 155

Ala Tyr Ala Ser Trp
1               5

<210> SEQ ID NO 156
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 156

Ala Tyr Ala Ser Ala
1               5

<210> SEQ ID NO 157
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 157

Ala Tyr Ala Ser Met
1               5

<210> SEQ ID NO 158
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 158

Ala Tyr Ala Ser Xaa
1               5

<210> SEQ ID NO 159
<211> LENGTH: 5
<212> TYPE: PRT
<213> ORGANISM: Artificial sequence
```

```
<220> FEATURE:
<223> OTHER INFORMATION: amino acid recognition sequence

<400> SEQUENCE: 159

Met Ala Val Ala Ala
1               5

<210> SEQ ID NO 160
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 160

Met Ala Val Ala Met
1               5

<210> SEQ ID NO 161
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 161

Met Ala Val Ala Xaa
1               5

<210> SEQ ID NO 162
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 162

Met Ala Val Val Xaa
1               5

<210> SEQ ID NO 163
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 163

Met Ala Val Ser Xaa
1               5

<210> SEQ ID NO 164
<211> LENGTH: 5
<212> TYPE: PRT
<213> ORGANISM: Artificial sequence
<220> FEATURE:
<223> OTHER INFORMATION: amino acid recognition sequence
```

<400> SEQUENCE: 164

Met Ala Ala Ala Ala
1               5

<210> SEQ ID NO 165
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 165

Met Ala Ala Ala Met
1               5

<210> SEQ ID NO 166
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 166

Met Ala Ala Ala Xaa
1               5

<210> SEQ ID NO 167
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 167

Met Ala Ala Val Trp
1               5

<210> SEQ ID NO 168
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 168

Met Ala Ala Val Ala
1               5

<210> SEQ ID NO 169
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 169

Met Ala Ala Val Met
1               5

<210> SEQ ID NO 170
<211> LENGTH: 5
<212> TYPE: PRT

```
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 170

Met Ala Ala Val Xaa
1               5

<210> SEQ ID NO 171
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 171

Met Ala Ala Ser Xaa
1               5

<210> SEQ ID NO 172
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 172

Met Val Val Ala Trp
1               5

<210> SEQ ID NO 173
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 173

Met Val Val Ala Ala
1               5

<210> SEQ ID NO 174
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 174

Met Val Val Ala Met
1               5

<210> SEQ ID NO 175
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
```

```
<223> OTHER INFORMATION: Xaa = norleucine

<400> SEQUENCE: 175

Met Val Val Ala Xaa
1               5

<210> SEQ ID NO 176
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 176

Met Val Val Val Met
1               5

<210> SEQ ID NO 177
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 177

Met Val Val Val Xaa
1               5

<210> SEQ ID NO 178
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 178

Met Val Val Ser Xaa
1               5

<210> SEQ ID NO 179
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 179

Met Val Ala Ala Met
1               5

<210> SEQ ID NO 180
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine
```

```
<400> SEQUENCE: 180

Met Val Ala Ala Xaa
1               5

<210> SEQ ID NO 181
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 181

Met Val Ala Val Met
1               5

<210> SEQ ID NO 182
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 182

Met Val Ala Val Xaa
1               5

<210> SEQ ID NO 183
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 183

Met Val Ala Ser Xaa
1               5

<210> SEQ ID NO 184
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 184

Met Ser Val Ala Trp
1               5

<210> SEQ ID NO 185
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 185

Met Ser Val Ala Ala
1               5
```

```
<210> SEQ ID NO 186
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 186

Met Ser Val Ala Met
1               5

<210> SEQ ID NO 187
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 187

Met Ser Val Ala Xaa
1               5

<210> SEQ ID NO 188
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 188

Met Ser Val Val Trp
1               5

<210> SEQ ID NO 189
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 189

Met Ser Val Val Ala
1               5

<210> SEQ ID NO 190
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 190

Met Ser Val Val Met
1               5

<210> SEQ ID NO 191
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine
```

```
<400> SEQUENCE: 191

Met Ser Val Val Xaa
1               5

<210> SEQ ID NO 192
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 192

Met Ser Val Ser Met
1               5

<210> SEQ ID NO 193
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 193

Met Ser Val Ser Xaa
1               5

<210> SEQ ID NO 194
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 194

Met Ser Ala Ala Trp
1               5

<210> SEQ ID NO 195
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 195

Met Ser Ala Ala Ala
1               5

<210> SEQ ID NO 196
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 196

Met Ser Ala Ala Met
1               5

<210> SEQ ID NO 197
<211> LENGTH: 5
<212> TYPE: PRT
```

```
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 197

Met Ser Ala Ala Xaa
1               5

<210> SEQ ID NO 198
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 198

Met Ser Ala Val Trp
1               5

<210> SEQ ID NO 199
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 199

Met Ser Ala Val Ala
1               5

<210> SEQ ID NO 200
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 200

Met Ser Ala Val Met
1               5

<210> SEQ ID NO 201
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 201

Met Ser Ala Val Xaa
1               5

<210> SEQ ID NO 202
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 202
```

Met Ser Ala Ser Met
1               5

<210> SEQ ID NO 203
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 203

Met Ser Ala Ser Xaa
1               5

<210> SEQ ID NO 204
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 204

Met Tyr Val Ala Trp
1               5

<210> SEQ ID NO 205
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 205

Met Tyr Val Ala Ala
1               5

<210> SEQ ID NO 206
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 206

Met Tyr Val Ala Met
1               5

<210> SEQ ID NO 207
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 207

Met Tyr Val Ala Xaa
1               5

<210> SEQ ID NO 208
<211> LENGTH: 5

```
<212> TYPE: PRT
<213> ORGANISM: Artificial sequence
<220> FEATURE:
<223> OTHER INFORMATION: amino acid recognition sequence

<400> SEQUENCE: 208

Met Tyr Val Val Trp
1               5

<210> SEQ ID NO 209
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 209

Met Tyr Val Val Ala
1               5

<210> SEQ ID NO 210
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 210

Met Tyr Val Val Met
1               5

<210> SEQ ID NO 211
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 211

Met Tyr Val Val Xaa
1               5

<210> SEQ ID NO 212
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 212

Met Tyr Val Ser Trp
1               5

<210> SEQ ID NO 213
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 213

Met Tyr Val Ser Ala
1               5
```

<210> SEQ ID NO 214
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 214

Met Tyr Val Ser Met
1               5

<210> SEQ ID NO 215
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 215

Met Tyr Val Ser Xaa
1               5

<210> SEQ ID NO 216
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 216

Met Tyr Ala Ala Trp
1               5

<210> SEQ ID NO 217
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 217

Met Tyr Ala Ala Ala
1               5

<210> SEQ ID NO 218
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 218

Met Tyr Ala Ala Met
1               5

<210> SEQ ID NO 219
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)

-continued

```
<223> OTHER INFORMATION: Xaa = norleucine

<400> SEQUENCE: 219

Met Tyr Ala Ala Xaa
1               5

<210> SEQ ID NO 220
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 220

Met Tyr Ala Val Trp
1               5

<210> SEQ ID NO 221
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 221

Met Tyr Ala Val Ala
1               5

<210> SEQ ID NO 222
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 222

Met Tyr Ala Val Met
1               5

<210> SEQ ID NO 223
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 223

Met Tyr Ala Val Xaa
1               5

<210> SEQ ID NO 224
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 224

Met Tyr Ala Ser Trp
1               5

<210> SEQ ID NO 225
<211> LENGTH: 5
```

```
<212> TYPE: PRT
<213> ORGANISM: Artificial sequence
<220> FEATURE:
<223> OTHER INFORMATION: amino acid recognition sequence

<400> SEQUENCE: 225

Met Tyr Ala Ser Ala
1               5

<210> SEQ ID NO 226
<211> LENGTH: 5
<212> TYPE: PRT
<213> ORGANISM: Artificial sequence
<220> FEATURE:
<223> OTHER INFORMATION: amino acid recognition sequence

<400> SEQUENCE: 226

Met Tyr Ala Ser Met
1               5

<210> SEQ ID NO 227
<211> LENGTH: 5
<212> TYPE: PRT
<213> ORGANISM: Artificial sequence
<220> FEATURE:
<223> OTHER INFORMATION: amino acid recognition sequence
<220> FEATURE:
<221> NAME/KEY: MISC_FEATURE
<222> LOCATION: (5)..(5)
<223> OTHER INFORMATION: Xaa = norleucine

<400> SEQUENCE: 227

Met Tyr Ala Ser Xaa
1               5

<210> SEQ ID NO 228
<211> LENGTH: 239
<212> TYPE: PRT
<213> ORGANISM: Artificial sequence
<220> FEATURE:
<223> OTHER INFORMATION: modified antibody fragment Fc-Sec-His
<220> FEATURE:
<221> NAME/KEY: MISC_FEATURE
<222> LOCATION: (233)..(233)
<223> OTHER INFORMATION: Xaa = selenocysteine

<400> SEQUENCE: 228

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
```

```
            130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
                210                 215                 220

Ser Leu Ser Leu Ser Pro Gly Ala Xaa His His His His His
225                 230                 235

<210> SEQ ID NO 229
<211> LENGTH: 483
<212> TYPE: PRT
<213> ORGANISM: Artificial sequence
<220> FEATURE:
<223> OTHER INFORMATION: modified antibody fragment Anti-CD138-scFv-Fc-
      Sec-His
<220> FEATURE:
<221> NAME/KEY: MISC_FEATURE
<222> LOCATION: (477)..(477)
<223> OTHER INFORMATION: Xaa = selenocysteine

<400> SEQUENCE: 229

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
                20                  25                  30

Leu Asn Trp Tyr Gln Gln Lys Pro Asp Gly Thr Val Glu Leu Leu Ile
                35                  40                  45

Tyr Tyr Thr Ser Thr Leu Gln Ser Gly Val Pro Ser Arg Phe Ser Gly
                50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Gln Val Gln Leu Gln Gln
                115                 120                 125

Ser Gly Ser Glu Leu Met Met Pro Gly Ala Ser Val Lys Ile Ser Cys
                130                 135                 140

Lys Ala Thr Gly Tyr Thr Phe Ser Asn Tyr Trp Ile Glu Trp Val Lys
145                 150                 155                 160

Gln Arg Pro Gly His Gly Leu Glu Trp Ile Gly Glu Ile Leu Pro Gly
                165                 170                 175

Thr Gly Arg Thr Ile Tyr Asn Glu Lys Phe Lys Gly Lys Ala Thr Phe
                180                 185                 190

Thr Ala Asp Ile Ser Ser Asn Thr Val Gln Met Gln Leu Ser Ser Leu
                195                 200                 205
```

Thr Ser Glu Asp Ser Ala Val Tyr Tyr Cys Ala Arg Arg Asp Tyr Tyr
    210                 215                 220

Gly Asn Phe Tyr Tyr Ala Met Asp Tyr Trp Gly Gln Gly Thr Ser Val
225                 230                 235                 240

Thr Val Ser Ser Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Ala Xaa His His His
465                 470                 475                 480

His His His

<210> SEQ ID NO 230
<211> LENGTH: 19
<212> TYPE: PRT
<213> ORGANISM: Homo sapiens

<400> SEQUENCE: 230

Met Asp Trp Thr Trp Arg Ile Leu Phe Leu Val Ala Ala Ala Thr Gly
1               5                   10                  15

Ala His Ser

CYCLIC PEPTIDE CONJUGATES AND METHODS OF USE

CROSS-REFERENCE TO RELATED APPLICATION

The present application is a continuation of U.S. application Ser. No. 15/024,928, filed Mar. 25, 2016, which claims the benefit of U.S. Provisional Application Ser. No. 61/883,910, filed Sep. 27, 2013, which are hereby incorporated by reference herein in their entireties, including any figures, tables, nucleic acid sequences, amino acid sequences, or drawings.

GOVERNMENT SUPPORT

This invention was made with government support under Grant number 1R43CA180308-01 awarded by the National Institutes of Health (NIH). The government has certain rights in the invention.

BACKGROUND OF THE INVENTION

Multiple myeloma is a disease characterized by the homing and uncontrolled growth of malignant plasma cells within the confines of the bone marrow. Despite the recent advances in therapy, multiple myeloma remains an incurable disease. 14,000 new cases of multiple myeloma are diagnosed each year in the United States with a five year survival rate of 37%. Although standard therapy will typically cause an initial response, myeloma patients ultimately develop drug resistance and become unresponsive to a variety of anti-cancer agents, a phenomenon known as multidrug resistance (MDR). Clinical observations indicate that despite divergent genetic changes typical of myeloma, current therapy is not curative in any subset of patients. The bone marrow microenvironment presents a rich source of extracellular matrices, cytokines and growth factors produced by constituents residing in the bone marrow stroma, including mesenchymal stem cells, fibroblast and mature osteoblasts, suggesting that the bone marrow microenvironment may contribute to the resistant phenotype and the failure of standard chemotherapy. It has been reported that adhesion of myeloma and leukemia cells to components of the extracellular matrix is sufficient to cause drug resistance. Targeting interactions between the microenvironment and myeloma cells may be an attractive strategy for increasing the efficacy of standard therapy.

BRIEF SUMMARY OF THE INVENTION

The development of drug-resistant malignancies presents significant challenges when treating multiple myeloma (MM) within the bone marrow microenvironment. By utilizing necrosis as an alternative cytotoxic pathway and blocking MM-induced bidirectional stromal cell signaling, a cyclic, peptidomimetic drug (MTI-101) has recently been produced with near nM $IC_{50}$ potency. Still, with rapid blood clearance of the small molecule and the hazard of localized inflammation due to a necrotic mechanism, it is favorable to pursue half-life and specificity augmenting strategies via antibody engineering. In combination with selenocysteine incorporation techniques, the inventors generated two mAb fragments, both IgG-derived Fc-Sec-His6 and scFv-αCD138-Fc-Sec-His6. Selective conjugation with MTI-101 then yielded ADCs with defined 1:1 drug:antibody ratios. Strong mono-affinity to targeted CD44 and bispecific CD44/CD138 binding with improved cytotoxic profiles in vitro were demonstrated, as well as improved survival in vivo. These results provide compelling data for the applicability of ADCs as therapeutics with the potential for even higher efficacy in vivo from additional effector mediation functions.

BRIEF DESCRIPTION OF THE DRAWINGS

FIG. 12A-12H show cytotoxicity of Fc-Sec-His/MTI-101 as revealed by flow cytometry. FSC/SSC scatter densities distinguished live cells (right population) and dead cells (left population). This was confirmed by PI staining.

FIGS. 14A-14D show cytotoxicity of anti-CD138-scFv-Fc-Sec-His/MTI-101 as revealed by flow cytometry.

MTI-101 toward U266 cells. Blue columns (left bar at each concentration) show the cytotoxicity of the indicated MTI-101 conjugates; red columns (right bar at each concentration) show the corresponding stop proteins at the same concentrations.

Figure 16:
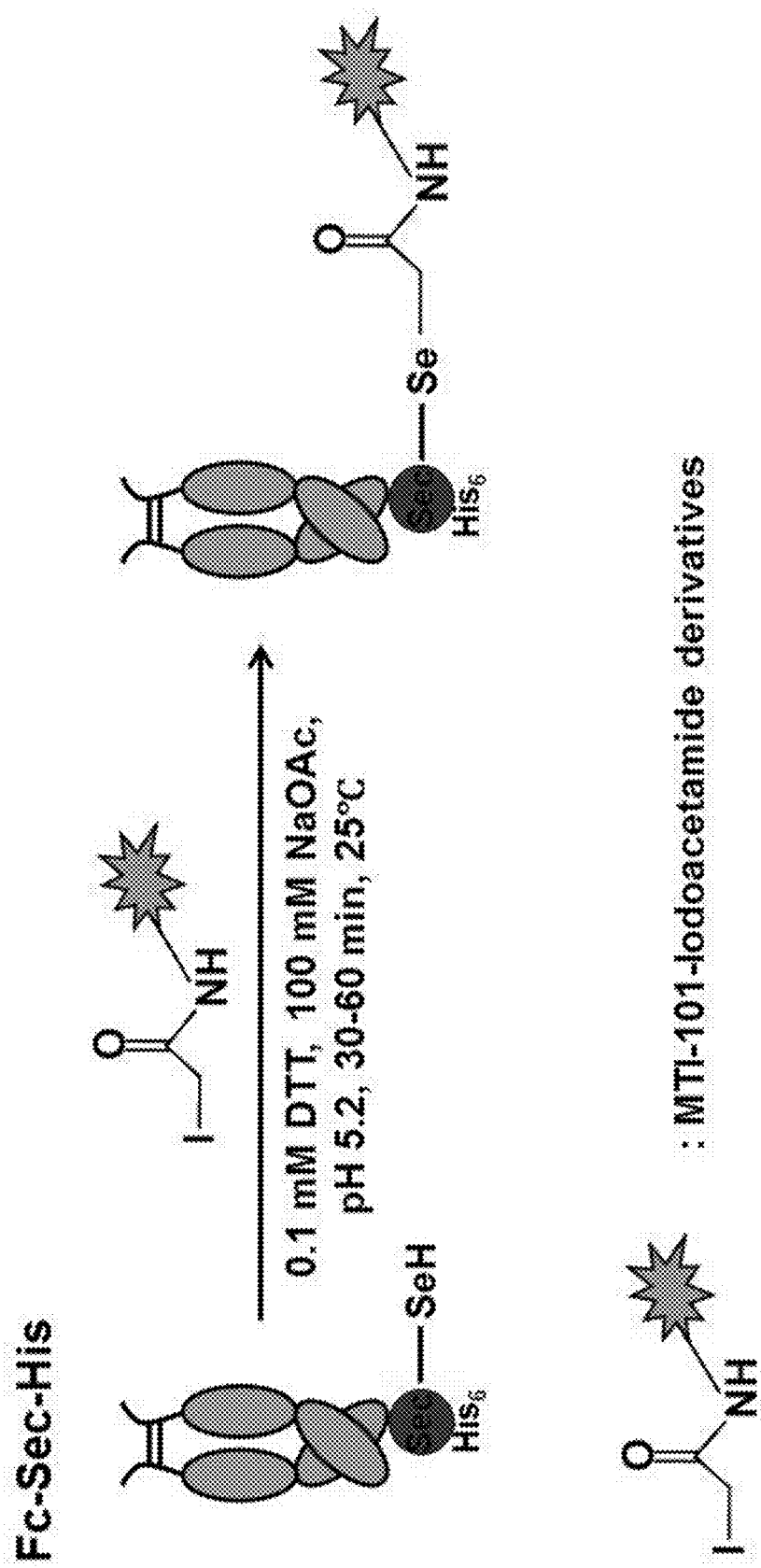

FIG. 16 shows an example of a reaction scheme for producing conjugates of the invention. Specifically, FIG. 16 depicts site-selective conjugation of MTI-101-iodoacetamide to Fc fragments with an engineered C-terminal selenocysteine (Sec) residue using slightly reducing and acidic conditions.

Figure 17:
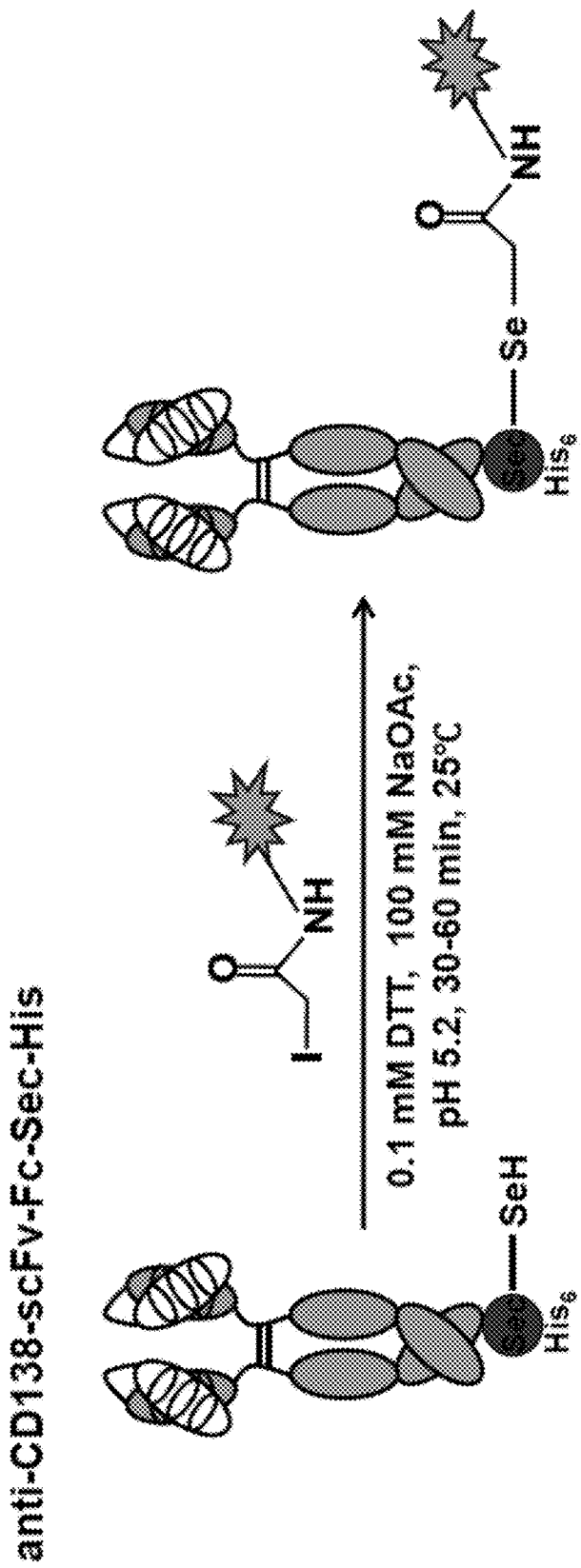

FIG. 17 shows an example of a reaction scheme for producing conjugates of the invention. Specifically, FIG. 17 depicts site-selective conjugation of MTI-101-iodoacetamide to an anti-CD138 mAb in scFv-Fc format with an engineered C-terminal selenocysteine (Sec) residue using slightly reducing and acidic conditions.

Figure 18A:
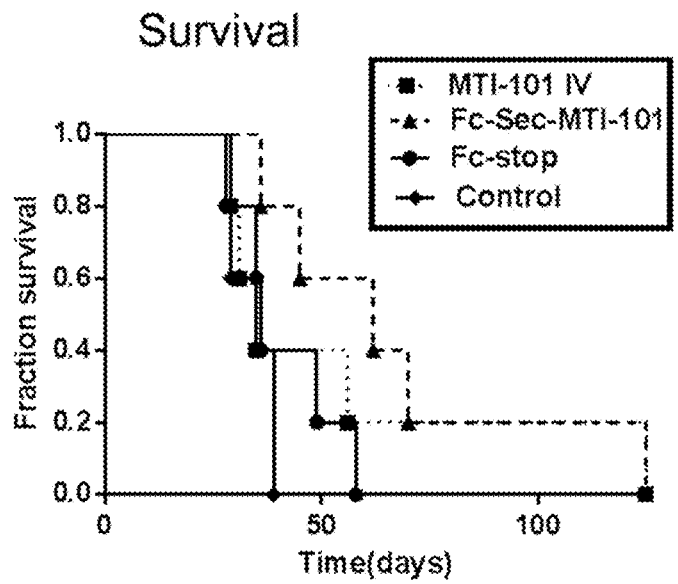
Figure 18B:
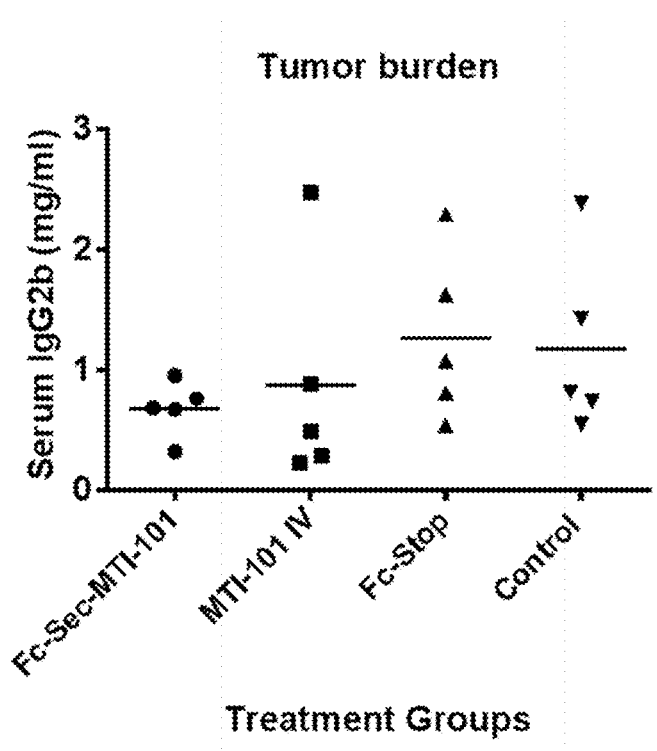

FIGS. 18A-18B show cytotoxicity of Fc-Sec-His/MTI-101 in vivo and tumor burden over time. One million 5TGM1 cells were injected intravenously (i.v.) in C57BL6/KaLwRij mice. Mice injected i.v. were treated once weekly for 3 weeks with 10 mg/kg Fc-Sec-MTI-101, 10 mg/kg Fc-stop, or an equal payload of MTI-101 (0.3285 mg/kg). The mice were monitored daily and euthanized if they exhibited hind leg paralysis, lethargy, or tumor masses exceeding 2 cm long. Medium survival was 35 days for control and MTI-101 IV equal payload, 26 days for FC-Sec-MTI-101 and 62 days for Fc-Sec-MTI-101 (n=5 animals per group), as shown in FIG. 18B. IgG2b levels were measured by ELISA 28 days following tumor inoculation. Mice treated with Fc-Sec-MTI-101 demonstrate a significant reduction in IgG2b levels compared to control and Fc-Stop.

DETAILED DESCRIPTION OF THE INVENTION

Figure 1:
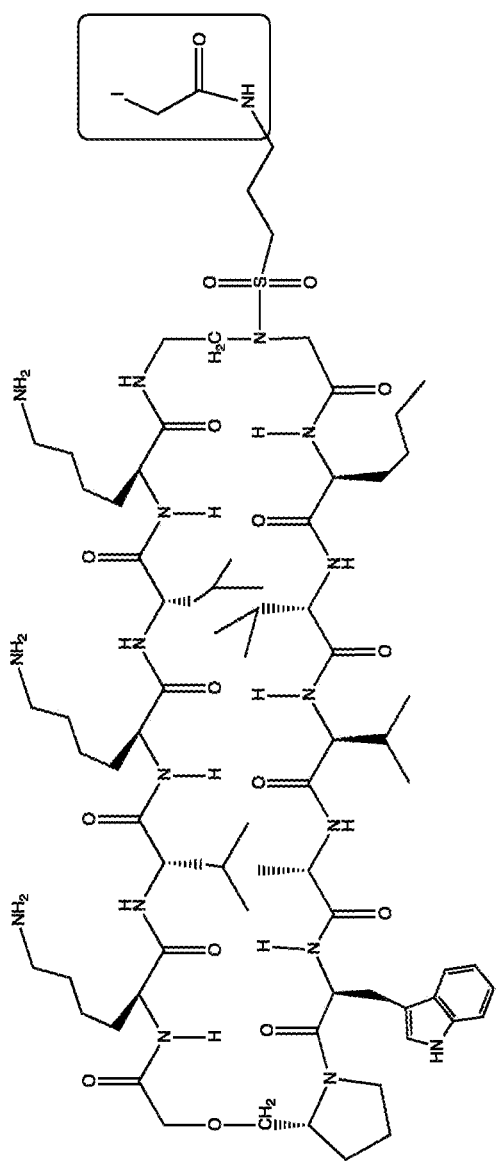
FIG. 1 shows an MTI-101 iodoacetamide adduct of the invention.

MTI-101 is an anti-CD44 targeting circular peptide (Gebhard, A. W., et al., "MTI-101 (cyclized HYD1) binds a CD44 containing complex and induces necrotic cell death in multiple myeloma," *Mol Cancer Ther,* 2013, 12, 2446-2458; cyclic peptide 16 in PCT Application No. PCT/US2011/000512, published as WO 2011/115688 ("Integrin Interaction Inhibitors for the Treatment of Cancer" on Sep. 22, 2011), which are each incorporated herein by reference its entirety. An iodoacetamide derivative of MTI-101 is shown in FIG. 1.

With the goals of improving both the circulatory half-life and selectivity of the MTI-101 peptide and similar circular peptides for disease treatment (e.g., multiple myeloma treatment), the inventors have applied antibody engineering and conjugation strategies (Hofer, Thomas, et al. "An engineered selenocysteine defines a unique class of antibody derivatives." *Proceedings of the National Academy of Sciences.* 105.34 (2008): 12451-12456; Hofer, T., et al., "Molecularly defined antibody conjugation through a selenocysteine interface," *Biochemistry,* 2009, 48, 12047-12057; and Li, X., et al., "Antibody conjugation via one and two C-terminal selenocysteines," *Methods* 2014, 65, 133-138, which are each incorporated herein by reference in its entirety) to develop a cyclic peptide conjugate bearing a carrying agent.

Figure 2:
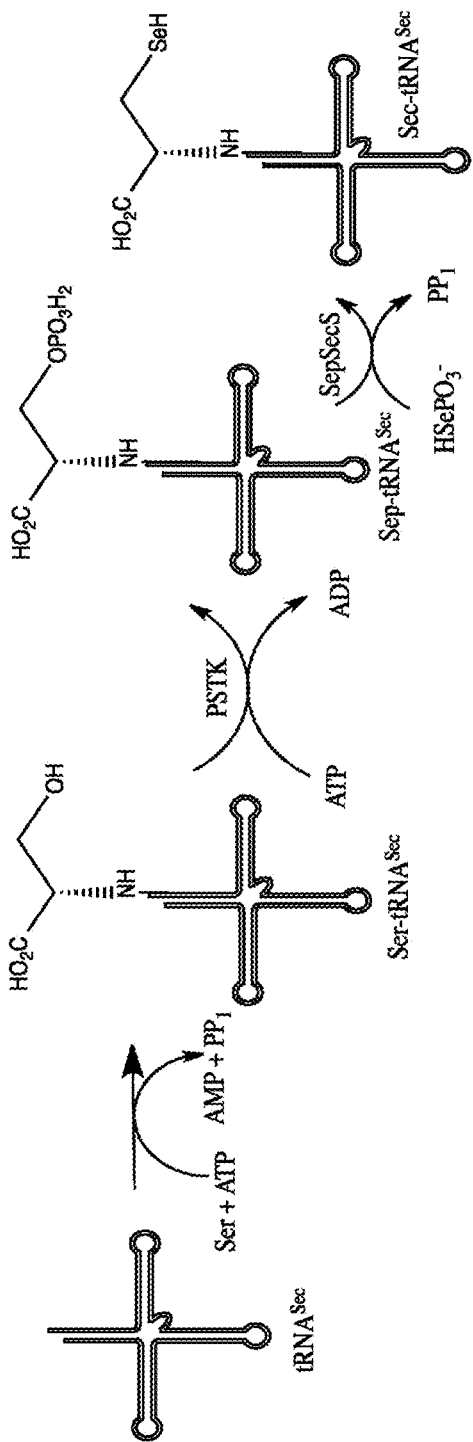
FIG. 2 shows a mechanism and strategy for selenocysteine incorporation.

Under certain conditions (Palioura, Sotiria, et al. "The human SepSecS-tRNASec complex reveals the mechanism of selenocysteine formation." *Science* 325.5938 (2009): 321-325, which is incorporated herein by reference in its entirety) as shown in FIG. 2, monoclonal antibodies and antigen binding fragments thereof ("antibody fragments") can be equipped with a C-terminal selenocysteine residue, the 21st natural amino acid, with unique chemical properties.

These conditions include a selenol pKa of about 5.2, which allows for selective conjugation in a 1:1 defined carrier:payload ratio. Compared to conventional cysteine and lysine conjugation technologies with heterogeneous drug:antibody ratios (DARs), defined DARs increase therapeutic indices, as these antibody-drug conjugates (ADCs) lack large batch-to-batch variability and the potential for undesired toxicity. Most importantly, this methodology provides a strategy to adjoin small molecules to mAbs and antibody fragments, which should increase the circulatory half-life of the small molecule owing to both increased size and FcRn-mediated recycling (Roopenian D C, Akilesh S. "FcRn: The neonatal Fc receptor comes of age." *Nat Rev Immunol* 7:715725. (2007), which is incorporated herein by reference in its entirety), and augment the potency of the small molecule by equipping it with the cytotoxic effector functions of the antibody molecule.

An aspect of the invention concerns a cyclic compound (a conjugate), comprising a recognition sequence and a non-recognition sequence, wherein the recognition sequence comprises at least four amino acids, wherein the non-recognition sequence comprises at least four amino acids, and wherein the recognition sequence is joined to the non-recognition sequence by a first linker and a second linker, wherein the first linker and the second linker are independently selected from the structures:

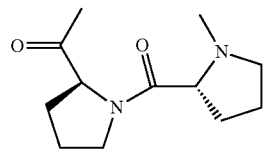 [SMILES: CC(=O)[C@@H]1CCCN1C(=O)[C@H]1CCCN1C]

(D-Pro-L-Pro);

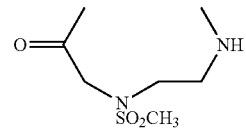

(methylsulfonamido aminoethylglycine);

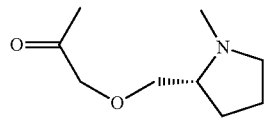

((pyrrolidin-2-ylmethoxy)acetate),

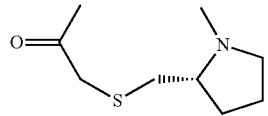

((pyrrolidin-2-ylmeththiyl)acetate);

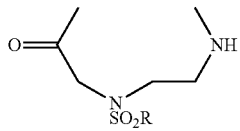

(substituted sulfonamide aminoethylglycine); or

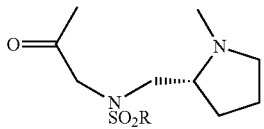

wherein R is a substituted or unsubstituted $C_2$-$C_{30}$ alkyl, aryl, alkylaryl, or arylalky group; wherein at least one of the first linker and the second linker is, or

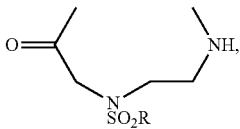

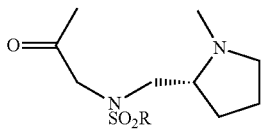

(N-(pyrrolidin-2-ylmethyl substituted sulfamido glycine), wherein at least one R is:

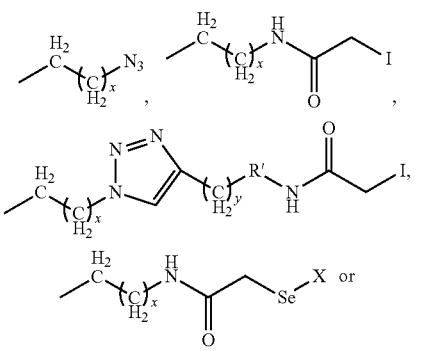

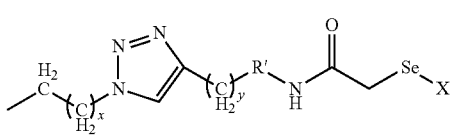

wherein x is 1-12, y is 1-12, R' is

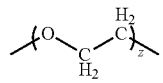

or absent, z is 1 to 20, and X comprises a carrying agent.

As used herein, the terms "cyclic compound", "cyclic peptide conjugate", "antibody drug conjugate", "ADC", "carrying agent:cyclic compound adduct" and "conjugate" refer to compounds of the invention.

In some embodiments, the non-recognition sequence is five amino acids selected from KLQLK (SEQ ID NO:1), QLKLK (SEQ ID NO:2), KQKLK (SEQ ID NO:3), (SEQ ID NO:4), or ELKLK (SEQ ID NO:5) wherein X=sarcosine and the recognition sequence is five amino acids selected from WAVAW (SEQ ID NO:6), WAVAA (SEQ ID NO:7), WAVAM (SEQ ID NO:8), WAVAN* (SEQ ID NO:9), WAVVN* (SEQ ID NO:10), WAVSN* (SEQ ID NO:11), WAAAW (SEQ ID NO:12), WAAAA (SEQ ID NO:13), WAAAM (SEQ ID NO:14), WAAAN* (SEQ ID NO:15), WAAVW (SEQ ID NO:16), WAAVA (SEQ ID NO:17), WAAVM (SEQ ID NO:18), WAAVN* (SEQ ID NO:19), WAASN* (SEQ ID NO:20), WVVAW (SEQ ID NO:21), WVVAA (SEQ ID NO:22), WVVAM (SEQ ID NO:23), WVVAN* (SEQ ID NO:24), WVVVW (SEQ ID NO:25), WVVVA (SEQ ID NO:26), WVVVM (SEQ ID NO:27), WVVVN* (SEQ ID NO:28), WVVSN* (SEQ ID NO:29), WVAAN* (SEQ ID NO:30), WVAVW (SEQ ID NO:31), WVAVA (SEQ ID NO:32), WVAVM (SEQ ID NO:33), WVAVN* (SEQ ID NO:34), WVASN* (SEQ ID NO:35), WSVAW (SEQ ID NO:36), WSVAA (SEQ ID NO:37), WSVAM (SEQ ID NO:38), WSVAN* (SEQ ID NO:39), WSVVW (SEQ ID NO:40), WSVVA (SEQ ID NO:41), WSVVM (SEQ ID NO:42), WSVVN* (SEQ ID NO:43), WSVSW (SEQ ID NO:44), WSVSA (SEQ ID NO:45), WSVSM (SEQ ID NO:46), WSVSN* (SEQ ID NO:47), WSAAW (SEQ ID NO:48), WSAAA (SEQ ID NO:49), WSAAM (SEQ ID NO:50), WSAAN* (SEQ ID NO:51), WSAVW (SEQ ID NO:52), WSAVA (SEQ ID NO:53), WSAVM (SEQ ID NO:54), WSAVN* (SEQ ID NO:55), WSASW (SEQ ID NO:56), WSASA (SEQ ID NO:57), WSASM (SEQ ID NO:58), WSASN* (SEQ ID NO:59), WYVAW (SEQ ID NO:60), WYVAA (SEQ ID NO:61), WYVAM (SEQ ID NO:62), WYVAN* (SEQ ID NO:63), WYVVW (SEQ ID NO:64), WYVVA (SEQ ID NO:65), WYVVM (SEQ ID NO:66), WYVVN* (SEQ ID NO:67), WYVSW (SEQ ID NO:68), WYVSA (SEQ ID NO:69), WYVSM (SEQ ID NO:70), WYVSN* (SEQ ID NO:71), WYAAW (SEQ ID NO:72), WYAAA (SEQ ID NO:73), WYAAM (SEQ ID NO:74), WYAAN* (SEQ ID NO:75), WYAVW (SEQ ID NO:76), WYAVA (SEQ ID NO:77), WYAVM (SEQ ID NO:78), WYAVN* (SEQ ID NO:79), WYASW (SEQ ID NO:80), WYASA (SEQ ID NO:81), WYASM (SEQ ID NO:82), WYASN* (SEQ ID NO:83), AAVAA (SEQ ID NO:84), AAVAM (SEQ ID NO:85), AAVAN* (SEQ ID NO:86), AAVVN* (SEQ ID NO:87), AAVSN* (SEQ ID NO:88), AAAAA (SEQ ID NO:89), AAAAM (SEQ ID NO:90), AAAAN* (SEQ ID NO:91), AAAVW (SEQ ID NO:92), AAAVA (SEQ ID NO:93), AAAVM (SEQ ID NO:94), AAAVN* (SEQ ID NO:95), AAASM (SEQ ID NO:96), AAASN* (SEQ ID NO:97), AVVAW (SEQ ID NO:98), AVVAA (SEQ ID NO:99), AVVAM (SEQ ID NO:100), AVVAN* (SEQ ID NO:101), AVVVA (SEQ ID NO:102), AVVVM (SEQ ID NO:103), AVVVN* (SEQ ID NO:104), AVVSN* (SEQ ID NO:105), AVAAW (SEQ ID NO:106), AVAAM (SEQ ID NO:107), AVAAN* (SEQ ID NO:108), AVAVA (SEQ ID NO:109), AVAVM (SEQ ID NO:110), AVAVN* (SEQ ID NO:111), AVASN* (SEQ ID NO:112), ASVAW (SEQ ID NO:113), ASVAA (SEQ ID NO:114), ASVAM (SEQ ID NO:115), ASVAN* (SEQ ID NO:116), ASVVW (SEQ ID NO:117), ASVVA (SEQ ID NO:118), ASVVM (SEQ ID NO:119), ASVVN* (SEQ ID NO:120), ASVSA (SEQ ID NO:121), ASVSM (SEQ ID NO:122), ASVSN* (SEQ ID NO:123), ASAAW (SEQ ID NO:124), ASAAA (SEQ ID NO:125), ASAAM (SEQ ID NO:126), ASAAN* (SEQ ID NO:127), ASAVW (SEQ ID NO:128), ASAVA (SEQ ID NO:129), ASAVM (SEQ ID NO:130), ASAVN* (SEQ ID NO:131), ASASA (SEQ ID NO:132), ASASM (SEQ ID NO:133), ASASN* (SEQ ID NO:134), AYVAW (SEQ ID NO:135), AYVAA (SEQ ID NO:136), AYVAM (SEQ ID NO:137), AYVAN* (SEQ ID NO:138), AYVVW (SEQ ID NO:139), AYVVA (SEQ ID NO:140), AYVVM (SEQ ID NO:141), AYVVN* (SEQ ID NO:142), AYVSW (SEQ ID NO:143), AYVSA (SEQ ID NO:144), AYVSM (SEQ ID NO:145), AYVSN* (SEQ ID NO:146), AYAAW (SEQ ID NO:147), AYAAA (SEQ ID NO:148), AYAAM (SEQ ID NO:149), AYAAN* (SEQ ID NO:150), AYAVW (SEQ ID NO:151), AYAVA (SEQ ID NO:152), AYAVM (SEQ ID NO:153), AYAVN* (SEQ ID NO:154), AYASW (SEQ ID NO:155), AYASA (SEQ ID NO:156), AYASM (SEQ ID NO:157), AYASN* (SEQ ID NO:158), MAVAA (SEQ ID NO:159), MAVAM (SEQ ID NO:160), MAVAN* (SEQ ID NO:161), MAVVN* (SEQ ID NO:162), MAVSN* (SEQ ID NO:163), MAAAA (SEQ ID NO:164), MAAAM (SEQ ID NO:165), MAAAN* (SEQ ID NO:166), MAAVW (SEQ ID NO:167), MAAVA (SEQ ID NO:168), MAAVM (SEQ ID NO:169), MAAVN* (SEQ ID NO:170), MAASN* (SEQ ID NO:171), MVVAW (SEQ ID NO:172), MVVAA (SEQ ID NO:173), MVVAM (SEQ ID NO:174), MVVAN* (SEQ ID NO:175), MVVVM (SEQ ID NO:176), MVVVN* (SEQ ID NO:177), MVVSN* (SEQ ID NO:178), MVAAM (SEQ ID NO:179), MVAAN* (SEQ ID NO:180), MVAVM (SEQ ID NO:181), MVAVN* (SEQ ID NO:182), MVASN* (SEQ ID NO:183), MSVAW (SEQ ID NO:184), MSVAA (SEQ ID NO:185), MSVAM (SEQ ID NO:186), MSVAN* (SEQ ID NO:187), MSVVW (SEQ ID NO:188), MSVVA (SEQ ID NO:189), MSVVM (SEQ ID NO:190), MSVVN* (SEQ ID NO:191), MSVSM (SEQ ID NO:192), MSVSN* (SEQ ID NO:193), MSAAW (SEQ ID NO:194), MSAAA (SEQ ID NO:195), MSAAM (SEQ ID NO:196), MSAAN* (SEQ ID NO:197), MSAVW (SEQ ID NO:198), MSAVA (SEQ ID NO:199), MSAVM (SEQ ID NO:200), MSAVN* (SEQ ID NO:201), MSASM (SEQ ID NO:202), MSASN* (SEQ ID NO:203), MYVAW (SEQ ID NO:204), MYVAA (SEQ ID NO:205), MYVAM (SEQ ID NO:206), MYVAN* (SEQ ID NO:207), MYVVW (SEQ ID NO:208), MYVVA (SEQ ID NO:209), MYVVM (SEQ ID NO:210), MYVVN* (SEQ ID NO:211), MYVSW (SEQ ID NO:212), MYVSA (SEQ ID NO:213), MYVSM (SEQ ID NO:214), MYVSN* (SEQ ID NO:215), MYAAW (SEQ ID NO:216), MYAAA (SEQ ID NO:217), MYAAM (SEQ ID NO:218), MYAAN* (SEQ ID NO:219), MYAVW (SEQ ID NO:220), MYAVA (SEQ ID NO:221), MYAVM (SEQ ID NO:222), MYAVN* (SEQ ID NO:223), MYASW (SEQ ID NO:224), MYASA (SEQ ID NO:225), MYASM (SEQ ID NO:226), or MYASN* (SEQ ID NO:227), wherein N*=norleucine, and wherein either end of the recognition sequence can be a N-terminus.

In some embodiments of the cyclic compound, R is:

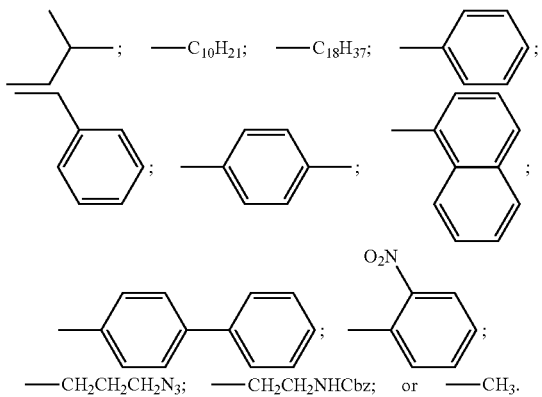

In some embodiments of the cyclic compound, R is H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl)amino $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_3$-$C_{30}$ alkylsulfonic acid, $C_3$-$C_{30}$ alkylsulfonate salt, $C_1$-$C_{30}$ carboxylate salt, $C_1$-$C_{30}$ thiocarboxylate salt, $C_1$-$C_{30}$ dithiocarboxylate salt, or $C_3$-$C_{30}$ alkyl$C_1$-$C_4$ trialkyammonium salt, wherein any carbon can be further substituted with any carbon can be substituted with a hydroxy, chloro, bromo, iodo, nitro, or carboxylic acid.

In some embodiments of the cyclic compound, the carrying agent comprises an amino acid, oligo(amino acid), poly(amino acid) or protein. For example, the carrying agent may comprise an antibody, or an Fc portion of an antibody, or an antigen-binding fragment of an antibody. In some embodiments, the carrying agent is a monoclonal antibody (mAb), or an Fc portion of a mAb, or an antigen binding fragment of a mAb, comprising a selenocysteine residue. In some embodiments, the carrying agent is a monoclonal antibody (mAb), or antigen binding fragment thereof, comprising a C-terminal selenocysteine residue.

Optionally, the carrying agent selected may be one that has the capacity to function as a targeting agent, targeting the cyclic compound to a desired site. A "targeting agent" as used herein refers to a moiety that recognizes, binds or adheres to a target moiety of a target molecule located for example in or on a cell, tissue (e.g., extracellular matrix), fluid, organism, or subset thereof. Thus, the term "carrying agent" is inclusive of targeting agents; therefore, every targeting agent is a carrying agent but a carrying agent is not necessarily a targeting agent.

Accordingly, in some embodiments, the carrying agent does not function as a targeting agent. For example, in some embodiments, the carrying agent is an Fc portion of an antibody (the Fc portion does not target any antigens). Selenocysteine-mediated site-specific and covalent linkage of the cyclic compound to the Fc-Sec-His protein prolongs the circulatory half-life of the cyclic compound, and, without wishing to be bound by theory, equips it with effector functions and bulkiness.

A targeting agent and its target molecule represent a binding pair of molecules, which interact with each other through any of a variety of molecular forces including, for example, ionic, covalent, hydrophobic, van der Waals, and hydrogen bonding, so that the pair have the property of binding specifically to each other. Specific binding means that the binding pair exhibit binding with each other under conditions where they do not bind to another molecule. Examples of binding pairs are biotin-avidin, hormone-receptor, receptor-ligand, enzyme-substrate, IgG-protein A, antigen-antibody, and the like. The targeting agent and its cognate target molecule exhibit a significant association for each other. This association may be evaluated by determining an equilibrium association constant (or binding constant) according to methods well known in the art. Affinity is calculated as $K_d = k_{off}/k_{on}$ ($k_{off}$ is the dissociation rate constant, $k_{on}$ is the association rate constant and $K_d$ is the equilibrium constant. Examples of targeting agents that may be used are disclosed in U.S. Patent Publication 20130171074 (Barbas, C. F. et al., "Targeting Compounds", assigned to The Scripps Research Institute, published Jul. 4, 2013, which is incorporated herein by reference in its entirety). Preferably, the target molecule (e.g., an antigen) is abundant in or on a target cell or tissue, relative to other cells or tissues. For example, the target molecule may be an antigen that is overexpressed in or on one or more tumors.

Carrying agents include, but are not limited to, small molecule organic compounds of 5,000 daltons or less such as drugs, proteins, peptides, peptidomimetics, glycoproteins, proteoglycans, lipids glycolipids, phospholipids, lipopolysaccharide, nucleic acids, proteoglycans, carbohydrates, and the like. Carrying agents may include well known therapeutic compounds including anti-neoplastic agents. Anti-neoplastic targeting agents may include targpaclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-octanoate, adriamycin-14-naphthaleneacetate, vinblastine, vincristine, mitomycin C, N-methyl mitomycin C, bleomycin Az, dideazatetrahydrofolic acid, aminopterin, methotrexate, cholchicine and cisplatin, and the like. Anti-microbial agents include aminoglycosides including gentamicin, antiviral compounds such as rifampicin, 3'-azido-3'-deoxythymidine (AZT) and acylovir, antifungal agents such as azoles including fluconazole, plyre macrolides such as amphotericin B, and candicidin, anti-parasitic compounds such as antimonials, and the like. Hormone targeting agents include toxins such as diphtheria toxin, cytokines such as CSF, GSF, GMCSF, TNF, erythropoietin, immunomodulators or cytokines such as the interferons or interleukins, a neuropeptide, reproductive hormone such as HGH, FSH, or LH, thyroid hormone, neurotransmitters such as acetylcholine, and hormone receptors such as the estrogen receptor.

In some embodiments, the carrying agent is an Fc portion of an antibody (which does not target any antigen), which does not function as a targeting agent.

In some embodiments, the carrying agent is an antibody or antigen-binding fragment thereof, which functions as a targeting agent.

The immunoglobulin may be a native immunoglobulin or modified immunoglobulin. In other embodiments, the targeting agent is not an antibody or antigen-binding fragment. For example, the targeting agent may be a small molecule. The carrying agent, including any linking moiety necessary for linking the carrying agent to an amino acid residue of the antibody combining site, may be about 300 daltons in size, and preferably may be at least about 400, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500 or even 5,000 daltons in size, with even larger sizes possible.

Suitable carrying agents in the invention can be a protein or peptide. "Polypeptide", "peptide," and "protein" are used interchangeably to refer to a polymer of amino acid residues (oligo(amino acid) or poly(amino acid)). As used herein, these terms are inclusive of amino acid polymers in which one or more amino acid residue is an artificial chemical analogue of a corresponding naturally occurring amino acid. These terms are also inclusive of naturally occurring amino acid polymers. Amino acids can be in the L or D form as long as the binding function of the peptide is maintained. Peptides can be of variable length, but are generally between about 4 and 200 amino acids in length. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well known in the art. See e.g., U.S. Pat. No. 6,013,625.

The term "protein" is also inclusive of antibodies and portions (i.e., fragments) of antibodies which or may not bind an antigen. For example, in some embodiments, the carrying agent comprises an antibody or antigen-binding portion thereof. In other embodiments, the carrying agent comprises an Fc portion of an antibody. In some embodiments, the antibodies are human antibodies. In some embodiments, the antibodies are non-human animal antibodies. Optionally, antibodies and antibody portions may be humanized.

Protein targeting agents that exhibit binding activity for a target molecule are well known in the art. For example, a targeting agent may be a viral peptide cell fusion inhibitor. This may include the T-20 HIV-1 gp41 fusion inhibitor which targets fusion receptors on HIV infected cells (for T-20, see U.S. Pat. Nos. 6,281,331 and 6,015,881 to Kang et al.; Nagashima et al. *J. Infectious Diseases* 183:1121, 2001; for other HIV inhibitors see U.S. Pat. No. 6,020,459 to Barney and WO 0151673A2 to Jeffs et al.), RSV cell fusion inhibitors (see WO 0164013A2 to Antczak and McKimm-Breschkin, *Curr. Opin. Invest. Drugs* 1:425-427, 2000 (VP-14637)), pneumovirus genus cell fusion inhibitors (see WO 9938508A1 by Nitz et al.), and the like. Targeting agents also include peptide hormones or peptide hormone analogues such as LHRH, bombesin/gastrin releasing peptide, somatastatin (e.g., RC-121 octapeptide), and the like, which may be used to target any of a variety of cancers, such as ovarian, mammary, prostate small cell of the lung, colorectal, gastric, and pancreatic. See, e.g., Schally et al., *Eur. J. Endocrinology*, 141:1-14, 1999.

Peptide targeting agents suitable for use in targeting compounds of the invention also may be identified using in vivo targeting of phage libraries that display a random library of peptide sequences (see, e.g., Arap et al., *Nature Medicine*, 2002 8(2):121-7; Arap et al., *Proc. Natl. Acad. Sci. USA* 2002 99(3):1527-1531; Trepel et al. *Curr. Opin. Chem. Biol.* 2002 6(3):399-404).

In some embodiments, the carrying agent specifically binds to a cell surface antigen, functioning as a targeting agent.

In some embodiments, the carrying agent specifically binds to a tumor associated antigen, functioning as a targeting agent.

In some embodiments, the targeting agent is specific for an integrin, such as alpha4 integrin, alpha3 integrin, and alpha6 integrin. In addition to antibodies and antigen-binding fragments thereof, suitable targeting agents for integrins include RGD peptides or peptidomimetics or non-RGD peptides or peptidomimetics. As used herein, reference to "Arg-Gly-Asp peptide" or "RGD peptide" is intended to refer to a peptide having one or more Arg-Gly-Asp containing sequence which may function as a binding site for a receptor of the "Arg-Gly-Asp family of receptors", e.g., an integrin. The term RGD peptide also includes amino acids that are functional equivalents (e.g., RLD or KGD) thereof provided they interact with the same RGD receptor. Peptides containing RGD sequences can be synthesized from amino acids by means well known in the art, using, for example, an automated peptide synthesizer, such as those manufactured by Applied Biosystems, Inc., Foster City, Calif. As used herein, "non-RGD" peptide refers to a peptide that is an antagonist or agonist of integrin binding to its ligand (e.g., fibronectin, vitronectin, laminin, collagen etc.) but does not involve an RGD binding site. Non-RGD integrin peptides are known (see, e.g., U.S. Pat. Nos. 5,767,071; 5,780,426; 6,365,619; Chang et al., *Bioorganic & Medicinal Chem Lett*, 12:159-163 (2002); Lin et al., *Bioorganic & Medicinal Chem Lett*, 12:133-136 (2002)), and the like.

In some embodiments, the carrying agent is a monoclonal antibody (mAb), or an Fc portion of a mAb, or an antigen binding fragment of a mAb, comprising a selenocycsteine residue. In some embodiments, the carrying agent is a monoclonal antibody (mAb), or Fc portion of a mAb, or antigen binding fragment thereof, comprising a C-terminal selenocysteine residue. In some embodiments, the targeting agent specifically binds to a cell surface antigen. In some embodiments, the carrying agent is a polyclonal antibody, or an Fc portion thereof, or an antigen-binding fragment thereof.

In some embodiments, the carrying agent specifically binds (targets) molecules, the abundance of which is associated with the disorder to be treated. Thus, a carrying agent can (optionally) be selected to target a molecule associated with a disease state, such as cancer. For example, a carrying agent that targets CD44 can be used for treatment of myeloma and other cancers. A carrying agent that targets alpha4 integrin can be used for treatment of hematopoietic cancers or metastatic solid tumors that home to bone.

In some embodiments, the targeting agent specifically binds to a tumor associated antigen. For example, the tumor associated antigen that is the target of the targeting agent may be an antigen overexpressed in tumors, hematopoietic differentiation antigen, cell surface differentiation antigen, growth factor receptor, angiogenesis or stromal antigen, etc. Non-limiting examples of antigens that may be targeted are disclosed in Carter P. et al., "Identification and validation of cell surface antigens for antibody targeting in oncology", *Endocrine-Related Cancer*, 2004, 11:659-687; Alonso-Camino V. et al., "CARbodies: Human Antibodies Against Cell Surface Tumor Antigens Selected from Repertoires Displayed on T Cell Chimeric Antigen Receptors", Molecular Therapy-Nucleic Acids, 2013:2:e93; Scott A. M. et al., "Tumour Antigens Recognized by Antibodies," Encyclopedia of Life Sciences, 2001, pp. 1-7; Part One: Tumor-associated Antigens (TAAs): Subclasses of TAAS, in Tumor-Associated Antigens, Edited by Olivier Gires and Barbara Seliger, 2009; Kiessling A. et al., "Tumor-Associated Antigens for Specific Immunotherapy of Prostate Cancer," *Cancers*, 2012, 4:193-217, which are incorporated herein by reference in their entirety.

In some embodiments, the targeting agent specifically binds to one or more antigens selected from among CD138, CD44, alpha4 integrin, alpha3 integrin, alpha6 integrin, EGFR, tumor suppressor cell antigen, cytotoxic T cell antigen, 17-1A, 707-AP, AFP, Annexin II, ART-4, BAGE, BAGE-1, β-catenin, BCG, bcr/abl, Bcr/abl e14a2 fusion junction, bcr-abl (b3a2), bcr-abl (b3a2), bcr-abl p190 (e1a2), bcr-abl p210 (b2a2), bcr-abl p210 (b3a2), bcr-abl p210 (b3a2), bullous pemphigoid antigen-1, CA19-9, CA125, CA215, CAG-3, CAMEL, Cancer-testis antigen, Caspase-8, CCL3, CCL4, CD16, CD20, CD3, CD30, CD55, CD63, CDC27, CDK-4, CDR3, CEA, cluster 5, cluster-5A, cyclin-dependent kinase-4, Cyp-B, DAM-10, DAM-6, Dek-cain, E7, EGFRvIII, EGP40, ELF2 M, EpCAM, FucGM1, G250, GA733, GAGE, GAGE-1-8, gastrin cancer associated antigen, GD2, GD3, globoH, glycophorin, GM1, GM2, GM3, GnTV, Gn-T-V, gp100, Her-2/neu, HERV-K-ME, high molecular weight-associated antigen, high molecular weight proteo-glycan (HMPG), HPV-16 E6, HPV-16 E7, HPVE6, HSP70-2M, HST-2, hTERT, human chorionic gonadotropin (HCG), Human milk fat globule (HMFG), iCE, KIAA0205, KK-LC-1, KM-HN-1, L6, LAGE-1, Lcose4Cer, LDLR/FUT, Lewis A, Lewis v/b, M protein, MAGE-1, MVC, MAGE-A1-12, MAGE-C2, MAHGE-3, MART-1/Melan-A, MC1R, ME491, MUC1, MUC2, mucin, MUM-1, MUM-2, MUM-3, mutated p53, Myosin, MZ2-E, N9 neuraminidase, NA88, NA88-A, nasopharyngeal carcinoma antigen, NGA, NK1/c-3, Novel bcr/ablk fusion BCR exons 1, 13, 14 with ABL exons 4, NY-ESO-1/LAGE-2, NY-ESO-1b, OC125, osteosarcoma associated antigen-1, P15, p190 mimor bcr-abl (e1a2), p53, Pml/RARα, Polysialic acid, PRAME, PSA, PSM, RU1, RU2, SAGE, SART-1, SART-2, SART-3, Sialyl LeA, Sp17, SSX-2, SSX-4, surface immunoglobulin, TAG-1, TAG-2, TEL/AML1, TPI, TRAG-3, TRP-1 (gp75), TRP-2, TRP2-INT2, hTRT, tumor associated glycoprotein-72 (TAG-72), tyrosinase, u-PA, WT1, and XAGE-1b, or an immunogenic fragment of any of the foregoing antigens.

In some embodiments, the tumor associated antigen is identified by the SEREX (serological analysis of recombinant expression cloning) approach or based on the serological screening of cDNA expression library generated from tumor tissues of various origin or cancer cell lines, and identifying immunogenic tumor proteins based on their reactivity with autologous patient sera.

Cyclic peptides, which may be used for making conjugates of the invention, and methods for making such cyclic peptides, are described in International Publication No. WO 2011/115688 (Hazlehurst et al., "Integrin Interaction Inhibitors for the Treatment of Cancer", published Sep. 22, 2011), which is incorporated by reference herein in its entirety.

Selenocysteine technology for making selenocysteine mediated hybrid antibody molecules is disclosed in U.S. Patent Publication 2010/0104510 (Rader C. et al.), published Apr. 29, 2010, which is incorporated by reference herein in its entirety.

The amino acid sequences of the mouse anti-human CD138 monoclonal antibody are disclosed in U.S. Patent Publication 2009/0169570 (Daelkin B. et al.), published Jul. 2, 2009, which is incorporated herein by reference in its entirety.

In some embodiments, the structure of the cyclic compound is:
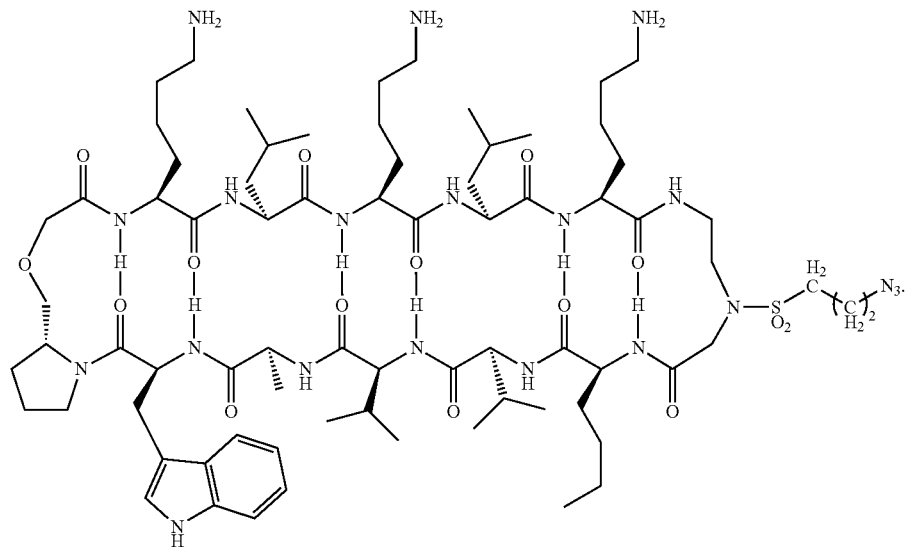
In some embodiments, the structure of the cyclic compound is:
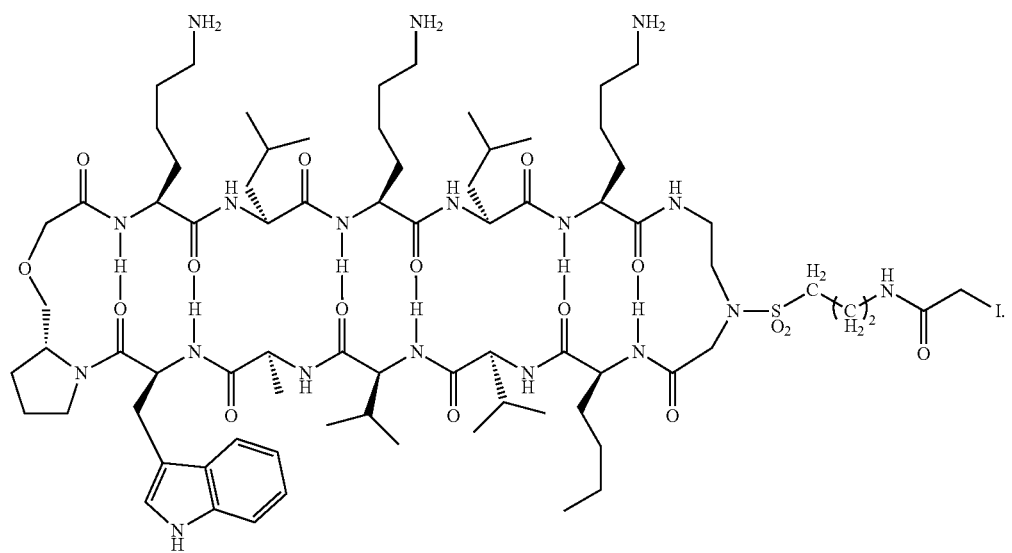

In some embodiments, the structure of the cyclic compound is:
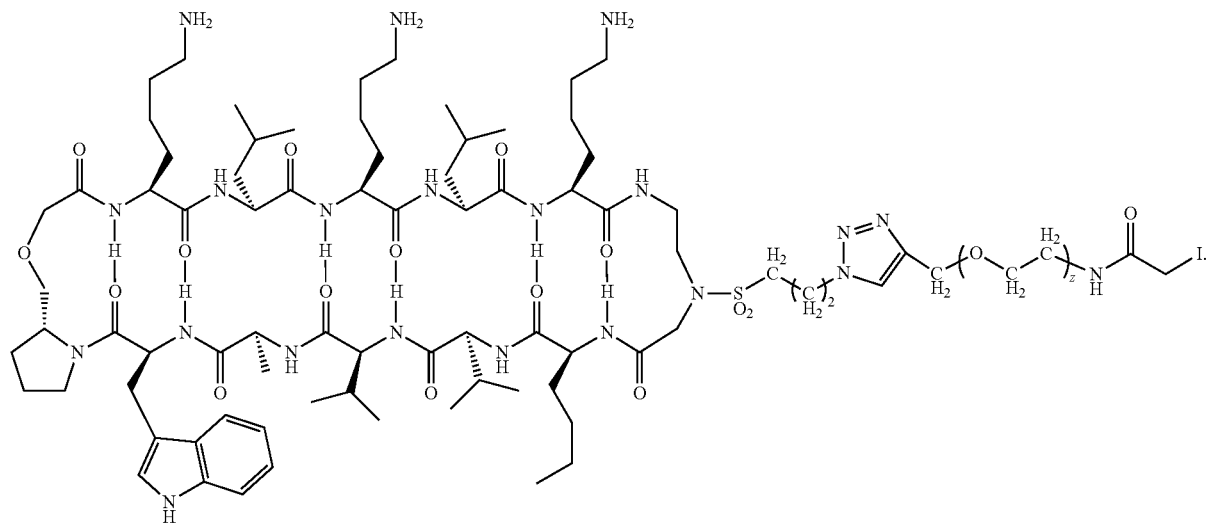
In some embodiments, the structure of the cyclic compound is:
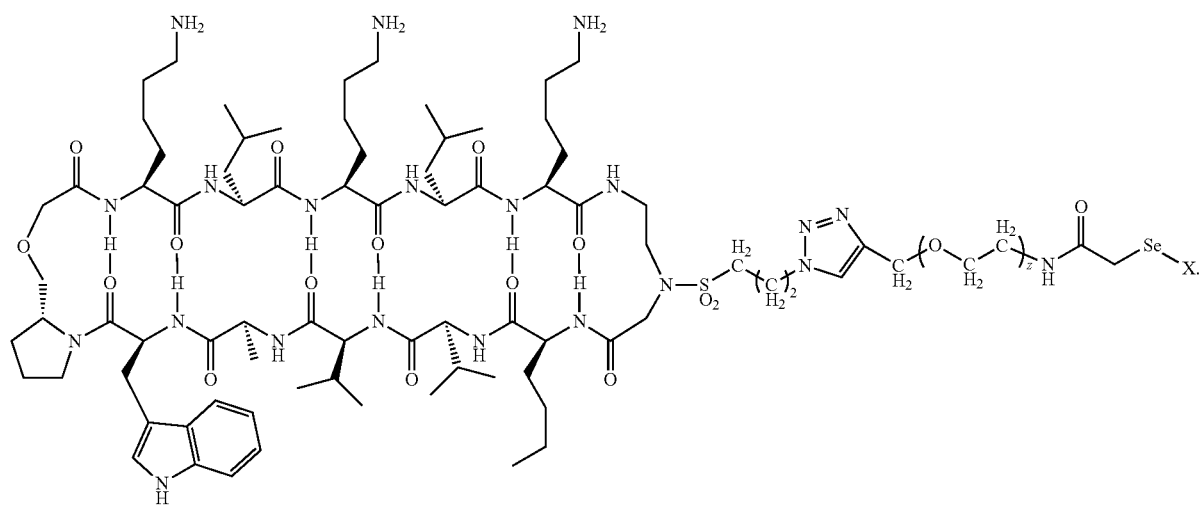

In some embodiments, the structure of the cyclic compound is:

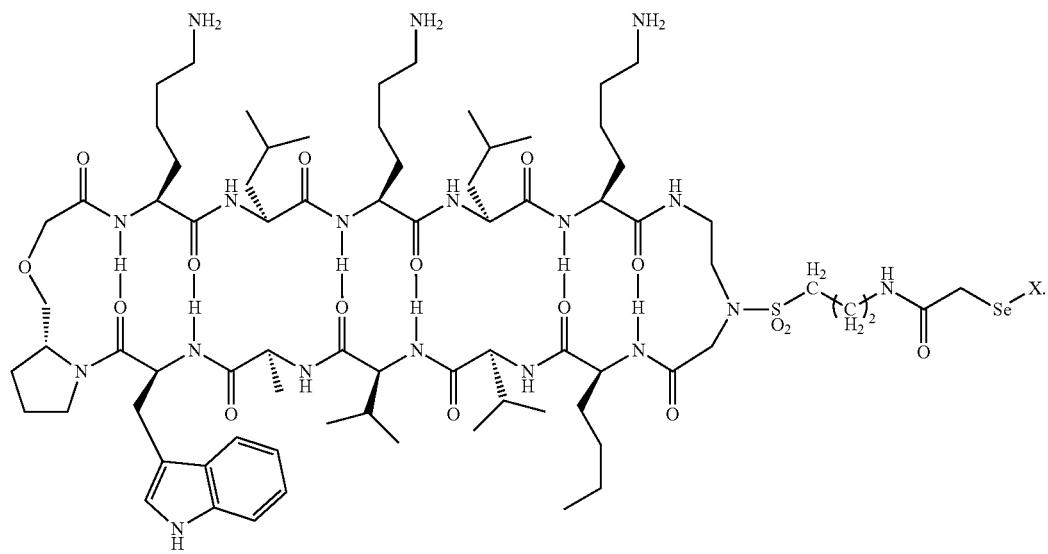

Another aspect of the invention is a linker, comprising:

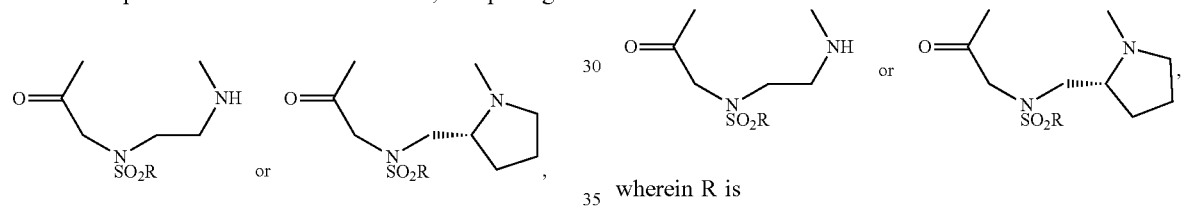

wherein R is

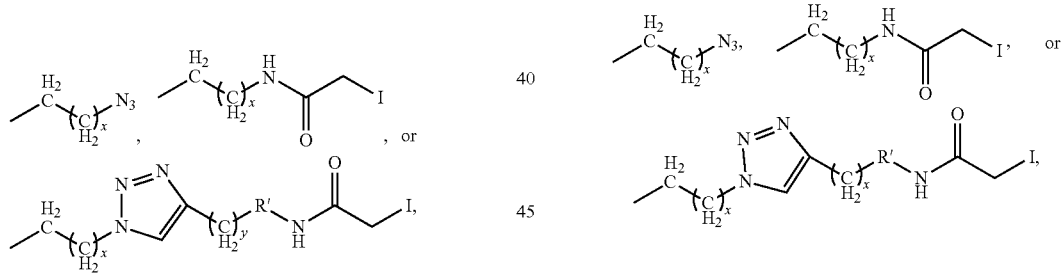

wherein x is 1-12, y is 1-12, R' is

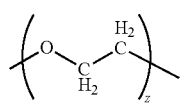

and z is 1 to 20.

Another aspect of the invention is a method of preparing a carrying agent:cyclic compound adduct, comprising:

providing a cyclic compound comprising a recognition sequence and a non-recognition sequence, wherein the recognition sequence comprises at least four amino acids, wherein the non-recognition sequence comprises at least four amino acids, and wherein the recognition sequence is joined to the non-recognition sequence by a first linker and a second linker, wherein at least one of the first linker and the second linker is:

wherein R is wherein x is 1-12, y is 1-12, R' is

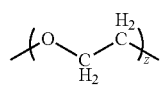

and z is 1 to 20;

providing a carrying agent X comprising a selenocysteine residue; and combining the carrying agent and the cyclic compound in an aqueous solution.

In some embodiments of the method of preparing a carrying agent:cyclic compound adduct, the aqueous solution comprises dithiothreitol (DTT) and the aqueous solution has an acidic pH.

In some embodiments of the method of preparing a carrying agent:cyclic compound adduct, wherein the pH is 4-6 and the concentration of DTT is 0.1-1 mM.

In some embodiments of the method of preparing a carrying agent:cyclic compound adduct, the cyclic compound comprises:

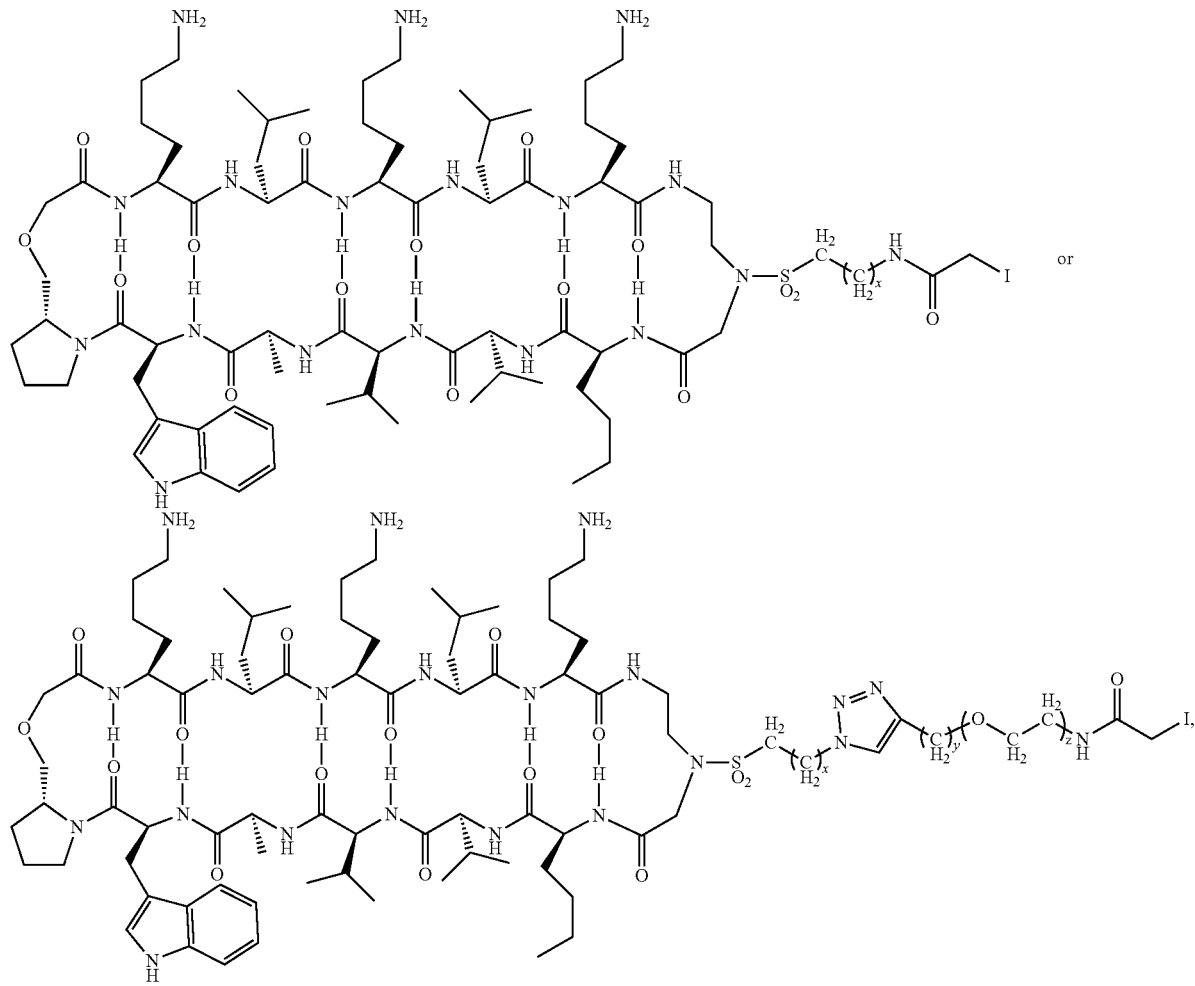

wherein x is 1-12, y is 1-12, and z is 1.

In some embodiments of the method of preparing a carrying agent:cyclic compound adduct, the carrying agent comprises an oligo(amino acid), poly(amino acid) or protein comprising a selenocysteine residue.

In some embodiments of the method of preparing a carrying agent:cyclic compound adduct, the carrying agent X is a monoclonal antibody (mAb) comprising a selenocysteine residue.

In some embodiments of the method of preparing a carrying agent:cyclic compound adduct the carrying agent X is the modified antibody Fc-Sec-His having the sequence: EPKSSDKTHTCPPCPAPELLGGPSVFLFPPKPKDTLM IS RTPEVTCVVVDVSHEDP EVKFNWYVDGVEVHNA KTKPREEQYNSTYRVVSVLTVLHQDWLNGKEYKC KVSNKALPAPIEKTISKAKGQPREPQVYTLPPSRDEL TKNQVSLTCLVKGFYPSDIAV EWESNGQPENNYKT T PPVLDSDGSFFLYSKLTVDKSRWQQGNVFSCSV M H EALH NHYTQKSLSLSPGAUHHHHHH (SEQ ID NO: 228) where U is the single letter amino acid code for selenocysteine.

In some embodiments of the method of preparing a carrying agent:cyclic compound adduct, the carrying agent X is a targeting agent that is the modified antibody Anti-CD138-scFv-Fc-Sec-His having the sequence: DIQMT QSTSSLSASLGDRVTISCSASQGINNYLNWYQQKPD GTVELLIYYTSTLQS GVPSRFSGSGSGTDYSLTISNL E PEDIGTYYCQQYSKLPRTFGGGTKLEIKGGGGS GGG GSGGGGSQVQLQQSGSELMMPGASVKISCKATGYT FSNYWIEWVKQRPGH GLEWIGEILPGTGRTIYNEKF KGKATFTADISSNTVQMQLSSLTSEDSAVYYCARRD Y YGNFYYAMDYWGQGTSVTVSSEPKSSDKTHTCPP CPAPELLGGPSVFLFPPKP KDTLMISRTPEVTCVVVD VSHEDPEVKFNWYVDGVEVHNAKTKPREEQYNSTY RVVSVLTVLHQDWLNGKEYKCKVSNKALPAPIEKT ISKAKGQPREPQVYTLPPSR DELTKNQVSLTCLVKG FYPSDIAVEWESNGQPENNYKTTPPVLDSDGSFFLY- SKL TVDKSRWQQGNVFSCSVMHEALHNHYTQKS LSLSPGAUHHHHHH (SEQ ID NO:229) where U is the single letter amino acid code for selenocysteine. This sequence lacks the signal peptide sequence of the anti-CD138 antibody (MDWTWRILFLVAAATGAHS (SEQ ID NO:230)), which is the first 19 amino acid sequence that will typically be cleaved off during antibody purification, prior to combining with the cyclic compound.

In some embodiments of the method of preparing a carrying agent:cyclic compound adduct, the carrying agent X comprises a residue of selenocysteine having a

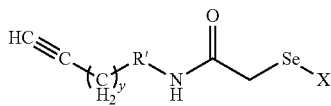

and wherein the cyclic compound comprises:

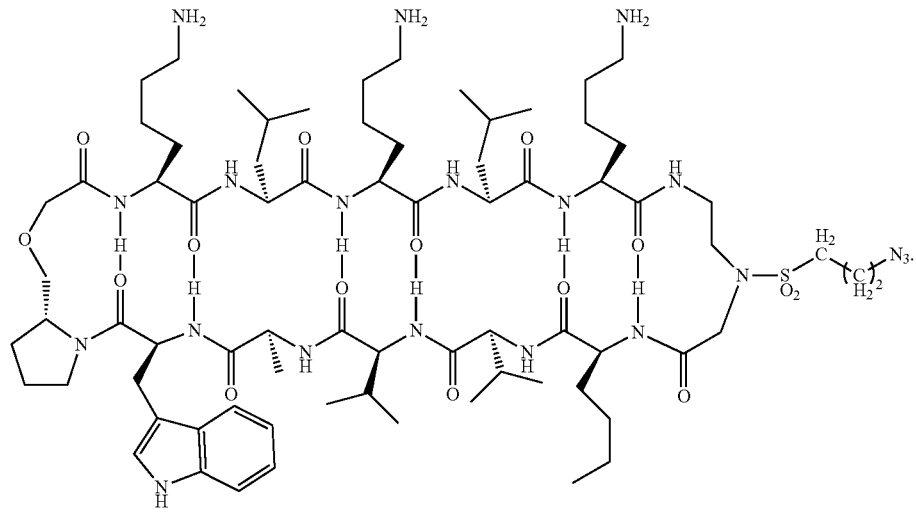

Another aspect of the invention concerns a method for treating a disorder in a subject, comprising administering an effective amount of a cyclic compound (conjugate) disclosed herein to the subject. In some embodiments, the subject is human. In other embodiments, the subject is a non-human animal.

In some embodiments, the disorder is a proliferation disorder, bone deficiency, or autoimmune disease.

In some embodiments, the proliferation disorder is myeloma or another malignancy.

In some embodiments, the cyclic compound is administered in a composition further comprising a pharmaceutically acceptable carrier.

Another aspect of the invention concerns a method of suppressing the growth of, or inducing apoptosis in, cells, comprising contacting the cells with an effective amount of a cyclic compound (conjugate) disclosed herein. In some embodiments, the cyclic compound is in a composition further comprising a pharmaceutically acceptable carrier.

In some embodiments, the contacting is carried out in vivo. In other embodiments, the contacting is carried out in vitro.

In some embodiments, the cells are human cells. In other embodiments, the cells are non-human animal cells. In some embodiments, the cells are mammalian cells.

In some embodiments, the cells are myeloma cells or other malignant cells.

Another aspect of the invention concerns a composition comprising a cyclic compound disclosed herein; and a pharmaceutically acceptable carrier. The composition may include additional agents, such as anti-cancer agent.

In some embodiments, the proliferation disorder to be treated is a cancer. In some embodiments, the proliferation disorder to be treated is a cancer producing a tumor characterized by β1 integrin signaling or β1 integrin mediated adhesion.

Examples of susceptible cancer types include, but are not limited to, cancer of the breast, pancreas, prostate, melanoma, myeloma, acute myeloid leukemia (AML), and lung. In some embodiments, the proliferation disorder to be treated is a cancer producing a tumor characterized by the CAM-DR phenotype. In some embodiments, the proliferation disorder to be treated is a cancer that exhibits elevated levels of the cleaved form of a4 integrin. In some embodiments, the proliferation disorder to be treated is a hematopoietic cancer. In some embodiments, the proliferation disorder to be treated is a metastatic solid tumor that homes to bone.

In some embodiments, the treatment methods further include determining whether the proliferation disorder exhibits the aforementioned characteristics β1 integrin signaling or β1 integrin mediated adhesion; CAM-DR phenotype; elevated α4 integrin level) prior to administration of the one or more compounds of the invention.

In some embodiments, the proliferation disorder to be treated is characterized by a proliferation of T-cells such as autoimmune disease, e.g., type 1 diabetes, lupus and multiple sclerosis, and pathological states such as graft rejection induced by the presentation of a foreign antigen such as a graft in response to a disease condition (e.g., kidney failure). Other non-malignant diseases characterized by proliferation of cells include cirrhosis of the liver and restenosis.

The methods of the present invention can be advantageously combined with at least one additional treatment method, including but not limited to, chemotherapy, radiation therapy, or any other therapy known to those of skill in the art for the treatment and management of proliferation disorders such as cancer.

While compounds of the invention can be administered to cells in vitro and in vivo as isolated agents, it is preferred to administer these compounds as part of a pharmaceutical composition. The subject invention thus further provides compositions comprising a compound of the invention in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The compounds of the invention can be formulated according to known methods for preparing pharmaceutically useful compositions. Formulations are described in a number of sources which are well known and readily available to those skilled in the art. For example, *Remington's Pharmaceutical Science* (Martin, E. W., 1995, Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of compounds may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

As used herein, the term "analogs" refers to compounds which are substantially the same as another compound but which may have been modified by, for example, adding side groups, oxidation or reduction of the parent structure. Analogs of the specifically disclosed compounds, and other agents disclosed herein, can be readily prepared using commonly known standard reactions. These standard reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature (Greene, T. W. and Wuts, P. G. M. "Protective Groups in Organic Synthesis" John Wiley & Sons, Inc. New York. 3rd Ed. pg. 819, 1999; Honda, T. et al. *Bioorg. Med. Chem. Lett.*, 1997, 7:1623-1628; Honda, T. et al. *Bioorg. Med. Chem. Lett.*, 1998, 8:2711-2714; Konoike, T. et al. *J. Org. Chem.*, 1997, 62:960-966; Honda, T. et al. *J. Med. Chem.*, 2000, 43:4233-4246; each of which are hereby incorporated herein by reference in their entirety). Analogs, fragments, and variants of the compounds exhibiting the desired biological activity (such as induction of cell death, cytotoxicity, cytostaticity, induction of cell cycle arrest, etc.) can be identified or confirmed using cellular assays or other in vitro or in vivo assays.

The compounds of the invention are useful for various non-therapeutic and therapeutic purposes. The compounds may be used for reducing aberrant cell growth in animals and humans. Because of such anti-proliferative properties of the compounds, they are useful in reducing unwanted cell growth in a wide variety of settings including in vitro and in vivo. In addition to their use in treatment methods, the compounds of the invention are useful as agents for investigating the role of integrin signaling and/or integrin mediated adhesion in cellular metabolism, and controlling integrin mediated malignant or non-malignant cell growth in vitro or in vivo.

Therapeutic application of the compounds and compositions comprising them can be accomplished by any suitable therapeutic method and technique presently or prospectively known to those skilled in the art. Further, the compounds of the invention can be used as starting materials or intermediates for the preparation of other useful compounds and compositions.

Compounds of the invention may be locally administered at one or more anatomical sites, such as sites of unwanted cell growth (such as a tumor site, e.g., injected or topically applied to the tumor), optionally in combination with a pharmaceutically acceptable carrier such as an inert diluent. Compounds of the invention may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds may be incorporated into sustained-release preparations and devices.

The active agent (e.g., the compounds (conjugates) of the invention) may also be administered intravenously or intraperitoneally by infusion or injection. Solutions of the active agent can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating the compounds of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compounds may be applied in pure-form, i.e., when they are liquids. However, it will generally be desirable to administer them topically to the skin as compositions, in combination with a dermatologically acceptable carrier, which may be a solid or a liquid.

The compounds of the subject invention can be applied topically to a subject's skin to reduce the size (and may include complete removal) of malignant or benign growths. The compounds of the invention can be applied directly to the growth. Preferably, the compound is applied to the growth in a formulation such as an ointment, cream, lotion, solution, tincture, or the like. Drug delivery systems for delivery of pharmacological substances to dermal lesions can also be used, such as that described in U.S. Pat. No. 5,167,649 (Zook).

Useful solid carriers include finely divided solids such as talc, clay, microcrystalline cellulose, silica, alumina and the like. Useful liquid carriers include water, alcohols or glycols or water-alcohol/glycol blends, in which the peptide can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the peptides to the skin are disclosed in Jacquet et al. (U.S. Pat. No. 4,608,392), Geria (U.S. Pat. No. 4,992,478), Smith et al. (U.S. Pat. No. 4,559,157) and Woltzman (U.S. Pat. No. 4,820,508).

Useful dosages of the pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Accordingly, the present invention includes a pharmaceutical composition comprising compound of the invention in combination with a pharmaceutically acceptable carrier. Pharmaceutical compositions adapted for oral, topical or parenteral administration, comprising an amount of a compound of the invention constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition. Advantageously, in some embodiments, administration of the compounds of the invention does not induce weight loss or overt signs of toxicity in the subject.

Depending upon the disorder or disease condition to be treated (e.g., a proliferation disorder, bone deficiency, or autoimmune disorder), a suitable dose(s) may be that amount that will reduce proliferation or growth of the target cell(s), or induce cell death. In the context of cancer, a suitable dose(s) is that which will result in a concentration of the active agent (one or more compounds of the invention) in cancer tissue, such as a malignant tumor, which is known to achieve the desired response. The preferred dosage is the amount which results in maximum inhibition of cancer cell growth, without unmanageable side effects. Administration of a compound of the invention can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds of the invention based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient", "subject", and "individual" are used interchangeably and are intended to include such human and non-human species. Likewise, in vitro methods of the present invention can be carried out on cells of such human and non-human species.

Patients in need of treatment using the methods of the present invention can be identified using standard techniques known to those in the medical or veterinary professions, as appropriate.

The terms "cancer" and "malignancy" are used herein interchangeably to refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer. In some embodiments, the cancer is multiple myeloma or another hematologic malignancy.

In some embodiments, the cancer or malignancy is one that expresses CD44. In some embodiments, the methods of the invention further comprise obtaining a sample of the cancer cells and determining whether the cells express one or more biomarkers, such as CD44, prior to administration of a peptide of the invention. Optionally, the methods may further comprise administering the peptide if the cancer sample expresses CD44.

Other non-limiting examples of cancers that may be treated are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may potentially be treated using the compounds of the present invention are also listed in Table 1.

TABLE 1

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| Acute Myeloid Leukemia, Adult | Hepatocellular (Liver) Cancer, Adult (Primary) |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sezary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |

TABLE 1-continued

Examples of Cancer Types

Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sezary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sezary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Uterine Cancer, Endometrial
Uterine Sarcoma Lymphoma, Primary Central Nervous System
Macroglobulinemia, Waldenstrom's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood

TABLE 1-continued

Examples of Cancer Types

Vaginal Cancer
Visual Pathway and Hypothalamic Glioma, Childhood
Vulvar Cancer
Waldenstrom's Macroglobulinemia
Wilms' Tumor As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site. The treatment methods of the invention can be utilized for early, middle, or late stage disease, and acute or chronic disease. In some embodiments, the tumor is characterized as one exhibiting the CAM-DR phenotype.

In some embodiments, the disorder to be treated is a proliferation disorder, bone deficiency, or autoimmune disease. In addition to cancer, the proliferation disorder may be a disorder involving an aberrant number of activated T-cells. Thus, administration of the compounds may be used to reduce the number of activated T-cells in a subject.

In some embodiments, the disorder to be treated is a bone deficiency or autoimmune disease, and the carrying agent is a non-targeting agent, such as an Fc portion of an antibody.

In some embodiments, the disorder to be treated is a bone deficiency caused by an osteopenic disorder, such as osteoporosis, Paget's disease, lytic bone metastases, periodontitis, rheumatoid arthritis, and bone loss due to immobilization.

In some embodiments, the subject has a cancer that increases osteoclast activity and/or induces bone resorption.

In some embodiments, the subject does not have a proliferation disorder, such as cancer.

The compounds of the invention may also be administered to treat an autoimmune disorder. In some embodiments, the autoimmune disorder selected from among: AIDS-associated myopathy, AIDS-associated neuropathy, Acute disseminated encephalomyelitis, Addison's Disease, Alopecia Areata, Anaphylaxis Reactions, Ankylosing Spondylitis, Antibody-related Neuropathies, Antiphospholipid Syndrome, Arthritis (e.g., rheumatoid arthritis, psoriatic arthritis, juvenile idiopathic arthritis), Autism, Autoimmune Atherosclerosis, Autoimmune Diabetes Insipidus, Autoimmune Endometriosis, Autoimmune Eye Diseases, Autoimmune Gastritis, Autoimmune Hemolytic Anemia, Autoimmune Hemophilia, Auto immune Hepatitis, Auto immune Interstitial Cystitis, Auto immune Lymphoproliferative Syndrome, Autoimmune Myopathy, Autoimmune Myocarditis, Autoimmune Neuropathies, Autoimmune Oophoritis, Autoimmune Orchitis, Autoimmune Thrombocytopenia, Autoimmune Thyroid Diseases, Autoimmune Urticaria, Autoimmune Uveitis, Autoimmune Vasculitis, Behcet's Disease, Bell's Palsy, Bullous Pemphigoid, CREST, Celiac Disease, Cerebellar degeneration (paraneoplastic), Chronic Fatigue Syndrome, Chronic Rhinosinusitis, Chronic inflammatory demyelinating polyneuropathy, Churg Strauss Syndrome, Connective Tissue Diseases, Crohn's Disease, Cutaneous Lupus, Dermatitis Herpetiformis, Dermatomyositis, Diabetes Mellitus, Discoid Lupus Erythematosus, Drug-induced Lupus, Endocrine Orbitopathy, Glomerulonephritis, Goodpasture Syndrome, Goodpasture's Syndrome, Graft-versus-Host Disease (GVHD), Graves Disease, Guillian-Barre Syndrome, Miller Fisher variant of the Guillian Barre Syndrome, axonal Guillian Bane Syndrome, demyelinating Guillian Barre Syndrome, Hashimoto Thyroiditis, Herpes Gestationis, Human T-cell lymphomavirus-associated myelopathy, Huntington's Disease, IgA Nephropathy, Immune Thrombocytopenic Purpura, Inclusion body myositis, Interstitial Cystitis, Isaacs syndrome, Lambert Eaton myasthenic syndrome, Limbic encephalitis, Lower motor neuron disease, Lyme Disease, MCTD, Microscopic Polyangiitis, Miller Fisher Syndrome, Mixed Connective Tissue Disease, Mononeuritis multiplex (vasculitis), Multiple Sclerosis (relapsing-remitting MS (RRMS), secondary-progressive MS (SPMS), primary-progressive MS (PPMS), and progressive-relapsing MS (PRMS)), Myasthenia Gravis, Myxedema, Meniere Disease, Neonatal LE, Neuropathies with dysproteinemias, Opsoclonus-myoclonus, PBC, POEMS syndrome, Paraneoplastic Autoimmune Syndromes, Pemphigus, Pemphigus Foliaceus, Pemphigus Vulgaris, Pernicious Anemia, Peyronie's Disease, Plaque Psoriasis, Plasmacytoma/myeloma neuropathy, Poly-Dermatomyositis, Polyarteritis *Nodosa*, Polyendocrine Deficiency Syndrome, Polyendocrine Deficiency Syndrome Type 1, Polyendocrine Deficiency Syndrome Type 2, Polyglandular Autoimmune Syndrome Type I, Polyglandular Autoimmune Syndrome Type II, Polyglandular Autoimmune Syndrome Type III, Polymyositis, Primary Biliary Cirrhosis, Primary Glomerulonephritis, Primary Sclerosing Cholangitis, Psoriasis, Psoriatic Arthritis, Rasmussen's Encephalitis, Raynaud's Disease, Relapsing Polychondritis, Retrobulbar neuritis, Rheumatic Diseases, Rheumatoid Arthritis, Scleroderma, Sensory neuropathies (paraneoplastic), Sjogren's Syndrome, Stiff-Person Syndrome, Subacute Thyroiditis, Subacute autonomic neuropathy, Sydenham Chorea, Sympathetic Ophthalmitis, Systemic Lupus Erythematosus, Transverse myelitis, Type 1 Diabetes, Ulcerative Colitis, Vasculitis, Vitiligo, Wegener's Granulomatosis, acrocyanosis, anaphylacetic reaction, autoimmune inner ear disease, bilateral sensorineural hearing loss, cold agglutinin hemolytic anemia, cold-induced immune hemolytic anemia, idiopathic endolymphatic hydrops, idiopathic progressive bilateral sensorineural hearing loss, immune-mediated inner ear disease, and mixed autoimmune hemolysis.

In some embodiments, the subject has graft-versus-host disease (GVHD), and the compound is administered to treat the GVHD in the subject. In some embodiments, the compound is administered before, during, and/or after a transplant to delay the onset of graft-versus-host disease (GVHD). In some embodiments, the transplant comprises an allograft or xenograft. In some embodiments, the transplant comprises an allogeneic stem cell, bone marrow, or organ transplant.

Combination Treatments

According to the method of the subject invention, a compound disclosed herein (a conjugate) can be administered to a subject by itself, or co-administered with one or more other agents such as another compound of the invention (another conjugate), or a different agent or agents. In some embodiments, the additional agent is one or more anti-cancer agents. Anti-cancer agents include but are not limited to the chemotherapeutic agents listed Table 3.

Co-administration can be carried out simultaneously (in the same or separate formulations) or consecutively with the additional agent administered before and/or after one or more compounds disclosed herein. Furthermore, according to the method of the subject invention, peptides of the invention can be administered to a subject as adjuvant therapy. For example, peptides of the invention can be administered to a patient in conjunction with chemotherapy.

Thus, the compounds of the invention, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the compounds of the invention, or act towards preventing any potential side effects which may be posed as a result of administration of the compounds. The compounds of the subject invention can be further conjugated to a therapeutic agent, as well.

Additional agents that can be co-administered to target cells in vitro or in vivo, such as in a subject, in the same or as a separate formulation, include those that modify a given biological response, such as immunomodulators. The additional agents may be, for example, small molecules, polypeptides (proteins, peptides, or antibodies or antibody fragments), or nucleic acids (encoding polypeptides or inhibitory nucleic acids such as antisense oligonucleotides or interfering RNA). For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more anti-cancer agents, such as cytotoxic agents, chemotherapeutic agents, anti-signaling agents, and anti-angiogenic agents.

In some embodiments, the compositions of the invention include at least one additional anti-cancer agent (e.g., a chemotherapeutic agent). In some embodiments of the methods of the invention, at least one additional anti-cancer agent is administered with the compound of the invention. In some embodiments, the anti-cancer agent is selected from among suberoylanilide hydroxamic acid (SAHA) or other histone deacetylase inhibitor, arsenic trioxide, doxorubicin or other anthracycline DNA intercalating agent, and etoposide or other topoisomerase II inhibitor.

In some embodiments, the compositions of the invention include one or more proteasome inhibitors (e.g., bortezomib), inhibitors of autophagy (e.g., chloroquine), alkylating agents (e.g., melphalan, cyclophosphamide), MEK inhibitors (e.g., PD98509), FAK/PYK2 inhibitors (e.g., PF562271), or EGFR inhibitors (e.g., erlotinib, gefitinib, cetuximab, panitumumab, zalutumumab, nimotuzumab, matuzumab), or a combination of two or more of the foregoing. Likewise, the methods of the invention include administration of one or more proteasome inhibitors, inhibitors of autophagy, alkylating agents, MEK inhibitors, FAK/PYK2 inhibitors, EGFR inhibitors, or a combination of two or more of the foregoing to cancer cells in vitro or to a subject before, during (in the same composition or separate compositions), or after administration of a compound (conjugate) disclosed herein.

In some embodiments, the compounds of the invention are administered before, during, or after:

(a) an agent for treatment of a bone deficiency, selected from among bisphosphonate (e.g., alendronate, risedronate, ibandronate, zoledronic acid), teriparatide, denosumab, and calcitonin; or (b) an agent for treatment of an autoimmune disorder, selected from among a corticosteroid (such as prednisone), nonsteroid drug such as azathioprine, cyclophosphamide, methotrexate, mycophenolate, mofetil, sirolimus, rituximab, tacrolimus, cyclosporine, or other immunosuppressive agent. The agent may be administered in the same composition as the compound of the invention or separately.

Compounds as described herein may include residues of L-amino acids, D-amino acids, or any combination thereof. In some embodiments, all amino acids of the peptide are D-amino acids. Amino acids may be from natural or non-natural sources. The 20 L-amino acids commonly found in proteins are identified herein by the conventional one-letter abbreviations known in the art, and the corresponding D-amino acids are generally designated by a lower case one letter symbol. Compounds of the invention may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylamino), with or without any of a wide variety of side chain modifications and/or substitutions (e.g., methylation, benzylation, t-butylation, tosylation, alkoxycarbonylamino, and the like). Such modifications and derivatives of an amino acid sequence, and others known to those of skill in the art, are herein termed "variants". Some derivatives include amino acids having an N-acetyl group (such that the amino group that represents the N-terminus of the peptide is acetylated) and/or a C-terminal amide group (i.e., the carboxy terminus of the peptide is amidated). Residues other than common amino acids that may be present include, but are not limited to, penicillamine, tetramethylene cysteine, pentamethylene cysteine, mercaptopropionic acid, pentamethylene-mercaptopropionic acid, 2-mercaptobenzene, 2-mercaptoaniline, 2-mercaptoproline, ornithine, diaminobutyric acid, aminoadipic acid, m-aminomethylbenzoic acid, and diaminopropionic acid.

Functional fragments according to the subject invention can comprise a contiguous span of at least 4 consecutive amino acids of a recognition sequence (also referred to as the recognition portion) and/or a non-recognition sequence (also referred to as the non-recognition portion) of the compounds disclosed herein. Peptides fragments according to the subject invention can be any integer in length from at least 4 consecutive amino acids to 1 amino acid less than a full length peptide (e.g., 1 amino acid less than the full length peptide). Thus, in some embodiments, functional fragments may be 4, 5, 6, 7, 8, or 9 amino acids in length (e.g., a span of 4, 5, 6, 7, 8, or 9 consecutive amino acids).

Each fragment of the subject invention can also be described in terms of its N-terminal and C-terminal positions. For example, combinations of N-terminal to C-terminal fragments of 6 contiguous amino acids to 1 amino acid less than the full length peptide of are included in the present invention. Thus, a 6 consecutive amino acid fragment could occupy positions selected from the group consisting of 1-6, 2-7, 3-8, 4-9, 5-10, etc. It is noted that all ranges used to describe any embodiment of the present invention are inclusive unless specifically set forth otherwise and that fragments of a given peptide can be any integer in length, provided that the length of the peptide fragment is at least one amino acid shorter than the full-length peptide from which the fragment is derived.

Fragments, as described herein, can be obtained by cleaving the peptides of the invention with a proteolytic enzyme (such as trypsin, chymotrypsin, or collagenase) or with a chemical reagent, such as cyanogen bromide (CNBr). Alternatively, peptide fragments can be generated in a highly acidic environment, for example at pH 2.5. Such peptide fragments may be equally well prepared by chemical synthesis or using hosts transformed with an expression vector according to the invention.

In certain preferred embodiments, fragments of the peptides disclosed herein retain at least one property or activity of the full-length peptide from which the fragments are derived.

Various detectable moieties may be attached to the compounds of the invention, such as at a nitrogen atom on one or more linkers. Such moieties that may find use with the compounds of the present invention can include but not be limited to sugars, lectins, antigens, intercalators, chelators, biotin, digoxygenin and combinations thereof. The particular choice of a dye as a labeling agent or cell uptake facilitator may depend upon physical characteristics such as absorption maxima, emission maxima, quantum yields, chemical stability and solvent solubility. A large number of fluorescent and chemiluminescent compounds have been shown to be useful for labeling proteins and nucleic acids. Examples of compounds that may be used as the dye portion can include but not be limited to xanthene, anthracene, cyanine, porphyrin and coumarin dyes. Examples of xanthene dyes that may be coupled to the peptides of the present invention can include but not be limited to fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2',7'-dimethoxyfluorescein (JOE), 5-carboxy-2',4',5',7'-tetrachlorofluorescein (ZOE) rhodol, rhodamine, tetramethylrhodamine (TAMRA), 4,7-dichlorotetramethyl rhodamine (DTAMRA), rhodamine X (ROX) and Texas Red. Examples of cyanine dyes that may find use with the peptides of the present invention can include but not be limited to Cy 3, Cy 3.5, Cy 5, Cy 5.5, Cy 7 and Cy 7.5. Other dyes that may find use with the peptides of the present invention can include but not be limited to energy transfer dyes, composite dyes and other aromatic compounds that give fluorescent signals. Chemiluminescent compounds that may be used with the peptides of the present invention can include but not be limited to dioxetane and acridinium esters. It should also be understood that ligands and dyes are not mutually exclusive groups. For instance, fluorescein is a well known example of a moiety that has been used as a fluorescent label and also as an antigen for labeled antibodies. Detectable moieties may be detected using devices and methodologies appropriate for the label in question.

The compounds expressly provided herein, as well as the fragments thereof, may further comprise linker elements that facilitate the attachment of the fragments to other molecules, amino acids, or polypeptide sequences. The linkers can also be used to attach the peptides, or fragments thereof, to solid support matrices for use in affinity purification protocols. Non-limiting examples of "linkers" suitable for the practice of the invention include chemical linkers (such as those sold by Pierce, Rockford, Ill.), or peptides that allow for the connection combinations of peptides (see, for example, linkers such as those disclosed in U.S. Pat. Nos. 6,121,424, 5,843,464, 5,750,352, and 5,990,275, hereby incorporated by reference in their entirety).

In other embodiments, the linker element can be an amino acid sequence (a peptide linker). In some embodiments, the peptide linker has one or more of the following characteristics: a) it allows for the free rotation of the peptides that it links (relative to each other); b) it is resistant or susceptible to digestion (cleavage) by proteases; and c) it does not interact with the peptides it joins together. In various embodiments, a multimeric construct according to the subject invention includes a peptide linker and the peptide linker is 5 to 60 amino acids in length. More preferably, the peptide linker is 10 to 30, amino acids in length; even more preferably, the peptide linker is 10 to 20 amino acids in length. In some embodiments, the peptide linker is 17 amino acids in length.

A "variant" or "variant peptide" (or peptide variant) is to be understood to designate peptides exhibiting, in relation to the peptides disclosed herein, certain modifications. These modifications can include a deletion, addition, or substitution of at least one amino acid (e.g., one, two, three or more amino acids), a truncation, an extension, a chimeric fusion (fusion protein), a mutation, or polypeptides exhibiting post-translational modifications. These modifications can occur anywhere in the peptide, e.g., one or both ends and/or in the middle. Among these homologous variant peptides, are those comprising amino acid sequences exhibiting between at least (or at least about) 20.00% to 99.99% (inclusive) identity to the full length, native, or naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length. Thus, variant peptides can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the peptide sequences of the instant invention. In a preferred embodiment, a variant or modified peptide exhibits at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity to the reference peptide. The percent identity is calculated with reference to the full-length polypeptide or the length of the fragment of a particular SEQ ID NO: that is identified. Preferably, the variant peptides retain at least one of the biological activities associated with the reference peptide.

For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 2). Conservative substitutions also include substitutions by amino acids having chemically modified side chains that do not eliminate the biological function of the resulting variant.

TABLE 2

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Fusion proteins according to the subject invention comprise one or more heterologous peptide sequences (e.g., tags that facilitate purification of the peptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental Biology* 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," J. of Chromatography A. 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", Biomolecular Engineering 16:79-86, Elsevier Science, B. V.; Smith [1998] "Cookbook for Eukaryotic Protein Expression: Yeast, Insect, and Plant Expression Systems," *The* Scientist 12(22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.).

In other embodiments, peptides of the subject invention can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety).

Peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.,* 1963, 85:2149, which involves assembling a linear peptide chain on a resin support using protected amino acids. Solid phase peptide synthesis typically utilizes either the Boc or Fmoc strategy, which are well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

The compounds disclosed herein may be modified by attachment of a second molecule that confers a desired property upon the peptide, such as increased half-life in the body, for example, pegylation. Such modifications also fall within the scope of the term "variant" as used herein.

Covalent attachment of a molecule or solid support may generally be achieved by first reacting the support material with a bifunctional reagent that will also react with a functional group, such as a hydroxyl, thiol, carboxyl, ketone or amino group, on the modulating agent. A preferred method of generating a linkage is via amino groups using glutaraldehyde. A peptide may be linked to cellulose via ester linkages. Similarly, amide linkages may be suitable for linkage to other molecules such as keyhole limpet hemocyanin or other support materials.

Within certain aspects of the present invention, one or more compounds as described herein may be present within a pharmaceutical composition. A pharmaceutical composition comprises one or more compounds of the invention in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A compound may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

Various techniques may be utilized to facilitate delivery of the compounds of the invention to the target cells in vitro (including ex vivo) and in vivo (Cellular Drug Delivery: Principles and Practice, edited by Lu, D. R. and Oie, S., Human Press, Totowa, N.J., 2004). Optionally, it may be desirable to facilitate delivery of the compounds of the invention through the outer cell membrane. Various protein carrier molecules may be further coupled to the compounds of the invention to assist penetration through biological membranes. For example, small regions (e.g., 9-16 amino acids) of proteins called protein transduction domains (PTDs) cell penetrating peptides (CPP) possess the ability to traverse biological membranes through protein transduction (Barnett, E. M. et al., *Invest. Opthalmol. Vis. Sci.*, 2006, 47:2589-2595; Schwarze S. R. et al., *Science*, 1999, 285 (5433):1569-1572; Wadia, J. S. and Dowdy, S. F., *Advanced Drug Delivery Reviews*, 2005, 57(4): 579-596; Wadia, J. S. and Dowdy, S. F., *Curr. Opin. Biotechnol.*, 2002, 13(1)52-56; Ho A. et al., *Cancer Research,* 2001, 61:474-477; Futaki et al., *J. Biol.* Chem., 2001, February, 276(8):5836-5840; Cao G. et al., *J. Neurosci.*, 2002, 22(13):5423-5431; Becker-Hapk, M. et al., Methods, 2001, 24:247-256; Snyder, E. L. and Dowdy, S. F., *Curr. Opin. Mol. Ther.*, 2001, 3:147-152; Lewin, M. et al., *Nat. Biotechnol.*, 2000, 18:410-414; Tung, C. H. et al., *Bioorg. Med. Chem.*, 2002, 10:3609-3614; Richard, J. P., et al., *J. Biol. Chem.*, Oct. 30, 2002, epub ahead of print). Transduction can occur in a receptor- and transporter-independent fashion that appears to target the lipid bilayer directly. Proteins (peptides) and compounds that are linked to PTDs (e.g., covalently) have the capability to traverse outer cell membranes. Preferably, the delivery peptide is a trans-activating transcriptional activator (TAT) peptide or an Antennapedia (ANT) peptide, or a derivative of either. PTDs can be linked to the peptides of the subject invention for transport across the cell membrane. One well characterized PTD is the human immunodeficient virus (HIV)-1 Tat peptide (see, for example, U.S. Pat. Nos. 5,804,604; 5,747,641; 5,674,980; 5,670,617; and 5,652,122). Peptides such as the homeodomain of Drosophila *antennapedia* (ANTP) and arginine-rich peptides display similar properties can be employed. VP22, a tegument protein from Herpes simplex virus type 1 (HSV-1), also has the ability to transport proteins across a cell membrane, and may be coupled to the compounds of the invention.

Definitions

As used herein, the terms "administering" or "administer" are defined as the introduction of a substance into cells in vitro or into the body of an individual in vivo by any route (for example, oral, nasal, ocular, rectal, vaginal and parenteral routes). Compounds of the invention (conjugates) may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN), or orally. For example, the compounds can be administered by direct injection into or on a tumor, or systemically (e.g., into the circulatory system), to kill circulating tumor cells (CTC).

In the context of the instant invention, the terms "oligopeptide", "polypeptide", "peptide" and "protein" can be used interchangeably; however, it should be understood that the invention does not relate to the peptides in natural form, that is to say that they are not in their natural environment but that the peptide may have been isolated or obtained by purification from natural sources or obtained from host cells prepared by genetic manipulation (e.g., the peptides, or fragments thereof, are recombinantly produced by host cells, or by chemical synthesis). Compounds of the invention may also contain non-natural amino acids, as will be described below. The terms "oligopeptide", "polypeptide", "peptide" and "protein" are also used, in the instant specification, to designate a series of residues of any length, typically L-amino acids, connected one to the other, typically by peptide bonds between the α-amino and carboxyl groups of adjacent amino acids. Linker elements can be joined to the peptides of the subject invention, for example, through peptide bonds or via chemical bonds (e.g., heterobifunctional chemical linker elements) as set forth below. Additionally, the terms "amino acid(s)" and "residue(s)" can be used interchangeably.

As used herein, the terms "treat" or "treatment" refer to both therapeutic treatment and prophylactic or preventative measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a compound of the invention may include reduction of undesirable cell proliferation, and/or induction of apoptosis and cytotoxicity. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., proliferation disorder) prior to administration of the compound of the invention.

As used herein, the term "(therapeutically) effective amount" refers to an amount of the compound of the invention or other agent (e.g., a drug) effective to treat a disease or disorder in a mammal. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; reduce (31 integrin signaling in the target cells, and/or relieve, to some extent, one or more of the symptoms associated with the cancer. To the extent the administered compound prevents growth of and/or kills existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" of the compound of the invention refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

The terms "cell" and "cells" are used interchangeably herein and are intended to include either a single cell or a plurality of cells, in vitro or in vivo, unless otherwise specified.

A compound of the invention may be administered before, during, or after administration of one or more other agents, such as an anti-cancer compound. If administered simultaneously, they may be administered within the same composition or separate compositions. As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). Anti-cancer agents include but are not limited to the chemotherapeutic agents listed Table 3.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the compounds of the invention are listed in Table 3. In a preferred embodiment, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 3

Examples of Chemotherapeutic Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |

TABLE 3-continued

Examples of Chemotherapeutic Agents

| | |
|---|---|
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |

TABLE 3-continued

Examples of Chemotherapeutic Agents

| | |
|---|---|
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

As used herein, the term "tumor" refers to all neoplastic cell growth and proliferation, whether malignant or benign, and all pre-cancerous and cancerous cells and tissues. For example, a particular cancer may be characterized by a solid tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The compounds of the invention are capable of inducing apoptosis in tumor cells and reducing tumor cell growth. The compounds of the invention can be administered locally at the site of a tumor (e.g., by direct injection) or remotely. The compounds of the invention can induce cell death in circulating tumor cells (CTC) in a subject, e.g., by administering the compounds intravenously. Furthermore, the compounds of the invention can prevent or reduce onset of metastasis to other tissues, e.g., to the bone.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

As used herein, the term "pharmaceutically acceptable salt or prodrug" is intended to describe any pharmaceutically acceptable form (such as an ester, phosphate ester, salt of an ester or a related group) of a compound of the invention or other agent, which, upon administration to a subject, provides the mature or base compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The terms "link" or "join" refers to any method known in the art for functionally connecting peptides, including, without limitation, recombinant fusion, covalent bonding, disulfide bonding, ionic bonding, hydrogen bonding, and electrostatic bonding.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state. Thus, compounds in accordance with the invention preferably do not contain materials normally associated with the peptides in their in situ environment.

As used in this specification, the singular forms "a", "an", and "the" include plural reference unless the context clearly dictates otherwise. Thus, for example, a reference to "a compound" includes more than one such compound. A reference to "a cell" includes more than one such cell, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Experimental controls are considered fundamental in experiments designed in accordance with the scientific method. It is routine in the art to use experimental controls in scientific experiments to prevent factors other than those being studied from affecting the outcome.

EXEMPLIFIED EMBODIMENTS

Examples of claimed embodiments of the invention include, but are not limited to:

Embodiment 1

A cyclic compound, comprising a recognition sequence and a non-recognition sequence, wherein said recognition sequence comprises at least four amino acids, wherein said non-recognition sequence comprises at least four amino acids, and wherein said recognition sequence is joined to said non-recognition sequence by a first linker and a second linker, wherein said first linker and said second linker are independently selected from the structures:

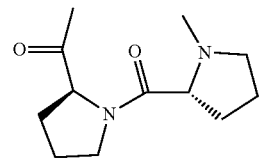 [SMILES: CC(=O)[C@@H]1CCCN1C(=O)[C@H]1CCCN1C]

(D-Pro-L-Pro);

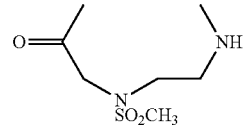

(methylsulfonamido aminoethylglycine);

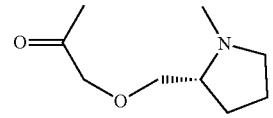

((pyrrolidin-2-ylmethoxy)acetate),

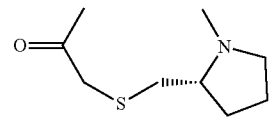

((pyrrolidin-2-ylmeththiyl)acetate);

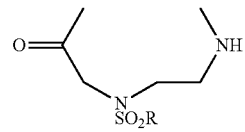

(substituted sulfonamide aminoethylglycine); or

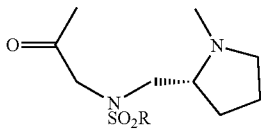

wherein R is a substituted or unsubstituted $C_2$-$C_{30}$ alkyl, aryl, alkylaryl, or arylalky group; wherein at least one of said first linker and said second linker is,

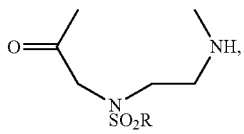

or

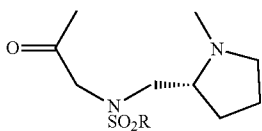

(N-(pyrrolidin-2-ylmethyl substituted sulfamido glycine), wherein at least one R is:

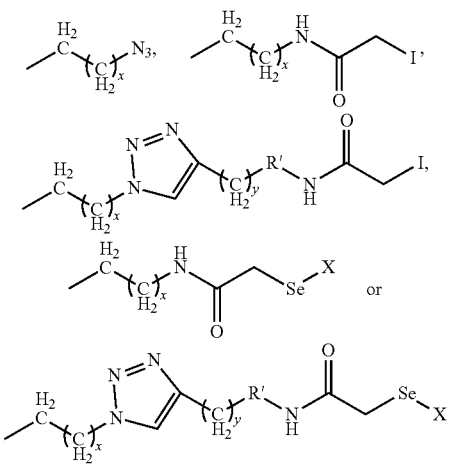

wherein x is 1-12, y is 1-12, R' is

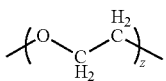

or absent, z is 1 to 20, and X comprises a carrying agent.

Embodiment 2

The cyclic compound of embodiment 1, wherein said non-recognition sequence is five amino acids selected from KLQLK (SEQ ID NO:1), QLKLK (SEQ ID NO:2), KQKLK (SEQ ID NO:3), KXKXK (SEQ ID NO:4), or ELKLK (SEQ ID NO:5) wherein X=sarcosine and the recognition sequence is five amino acids selected from WAVAW (SEQ ID NO:6), WAVAA (SEQ ID NO:7), WAVAM (SEQ ID NO:8), WAVAN* (SEQ ID NO:9), WAVVN* (SEQ ID NO:10), WAVSN* (SEQ ID NO:11), WAAAW (SEQ ID NO:12), WAAAA (SEQ ID NO:13), WAAAM (SEQ ID NO:14), WAAAN* (SEQ ID NO:15), WAAVW (SEQ ID NO:16), WAAVA (SEQ ID NO:17), WAAVM (SEQ ID NO:18), WAAVN* (SEQ ID NO:19), WAASN* (SEQ ID NO:20), WVVAW (SEQ ID NO:21), WVVAA (SEQ ID NO:22), WVVAM (SEQ ID NO:23), WVVAN* (SEQ ID NO:24), WVVVW (SEQ ID NO:25), WVVVA (SEQ ID NO:26), WVVVM (SEQ ID NO:27), WVVVN* (SEQ ID NO:28), WVVSN* (SEQ ID NO:29), WVAAN* (SEQ ID NO:30), WVAVW (SEQ ID NO:31), WVAVA (SEQ ID NO:32), WVAVM (SEQ ID NO:33), WVAVN* (SEQ ID NO:34), WVASN* (SEQ ID NO:35), WSVAW (SEQ ID NO:36), WSVAA (SEQ ID NO:37), WSVAM (SEQ ID NO:38), WSVAN* (SEQ ID NO:39), WSVVW (SEQ ID NO:40), WSVVA (SEQ ID NO:41), WSVVM (SEQ ID NO:42), WSVVN* (SEQ ID NO:43), WSVSW (SEQ ID NO:44), WSVSA (SEQ ID NO:45), WSVSM (SEQ ID NO:46), WSVSN* (SEQ ID NO:47), WSAAW (SEQ ID NO:48), WSAAA (SEQ ID NO:49), WSAAM (SEQ ID NO:50), WSAAN* (SEQ ID NO:51), WSAVW (SEQ ID NO:52), WSAVA (SEQ ID NO:53), WSAVM (SEQ ID NO:54), WSAVN* (SEQ ID NO:55), WSASW (SEQ ID NO:56), WSASA (SEQ ID NO:57), WSASM (SEQ ID NO:58), WSASN* (SEQ ID NO:59), WYVAW (SEQ ID NO:60), WYVAA (SEQ ID NO:61), WYVAM (SEQ ID NO:62), WYVAN* (SEQ ID NO:63), WYVVW (SEQ ID NO:64), WYVVA (SEQ ID NO:65), WYVVM (SEQ ID NO:66), WYVVN* (SEQ ID NO:67), WYVSW (SEQ ID NO:68), WYVSA (SEQ ID NO:69), WYVSM (SEQ ID NO:70), WYVSN* (SEQ ID NO:71), WYAAW (SEQ ID NO:72), WYAAA (SEQ ID NO:73), WYAAM (SEQ ID NO:74), WYAAN* (SEQ ID NO:75), WYAVW (SEQ ID NO:76), WYAVA (SEQ ID NO:77), WYAVM (SEQ ID NO:78), WYAVN* (SEQ ID NO:79), WYASW (SEQ ID NO:80), WYASA (SEQ ID NO:81), WYASM (SEQ ID NO:82), WYASN* (SEQ ID NO:83), AAVAA (SEQ ID NO:84), AAVAM (SEQ ID NO:85), AAVAN* (SEQ ID NO:86), AAVVN* (SEQ ID NO:87), AAVSN* (SEQ ID NO:88), AAAAA (SEQ ID NO:89), AAAAM (SEQ ID NO:90), AAAAN* (SEQ ID NO:91), AAAVW (SEQ ID NO:92), AAAVA (SEQ ID NO:93), AAAVM (SEQ ID NO:94), AAAVN* (SEQ ID NO:95), AAASM (SEQ ID NO:96), AAASN* (SEQ ID NO:97), AVVAW (SEQ ID NO:98), AVVAA (SEQ ID NO:99), AVVAM (SEQ ID NO:100), AVVAN* (SEQ ID NO:101), AVVVA (SEQ ID NO:102), AVVVM (SEQ ID NO:103), AVVVN* (SEQ ID NO:104), AVVSN* (SEQ ID NO:105), AVAAW (SEQ ID NO:106), AVAAM (SEQ ID NO:107), AVAAN* (SEQ ID NO:108), AVAVA (SEQ ID NO:109), AVAVM (SEQ ID NO:110), AVAVN* (SEQ ID NO:111), AVASN* (SEQ ID NO:112), ASVAW (SEQ ID NO:113), ASVAA (SEQ ID NO:114), ASVAM (SEQ ID NO:115), ASVAN* (SEQ ID NO:116), ASVVW (SEQ ID NO:117), ASVVA (SEQ ID NO:118), ASVVM (SEQ ID NO:119), ASVVN* (SEQ ID NO:120), ASVSA (SEQ ID NO:121), ASVSM (SEQ ID NO:122), ASVSN* (SEQ ID NO:123), ASAAW (SEQ ID NO:124), ASAAA (SEQ ID NO:125), ASAAM (SEQ ID NO:126), ASAAN* (SEQ ID NO:127), ASAVW (SEQ ID NO:128), ASAVA (SEQ ID NO:129), ASAVM (SEQ ID NO:130), ASAVN* (SEQ ID NO:131), ASASA (SEQ ID NO:132), ASASM (SEQ ID NO:133), ASASN* (SEQ ID NO:134), AYVAW (SEQ ID NO:135), AYVAA (SEQ ID NO:136), AYVAM (SEQ ID NO:137), AYVAN* (SEQ ID NO:138), AYVVW (SEQ ID NO:139), AYVVA (SEQ ID NO:140), AYVVM (SEQ ID NO:141), AYVVN* (SEQ ID NO:142), AYVSW (SEQ ID NO:143), AYVSA (SEQ ID NO:144), AYVSM (SEQ ID NO:145), AYVSN* (SEQ ID NO:146), AYAAW (SEQ ID NO:147), AYAAA (SEQ ID NO:148), AYAAM (SEQ ID NO:149), AYAAN* (SEQ ID NO:150), AYAVW (SEQ ID NO:151), AYAVA (SEQ ID NO:152), AYAVM (SEQ ID NO:153), AYAVN* (SEQ ID NO:154), AYASW (SEQ ID NO:155), AYASA (SEQ ID NO:156), AYASM (SEQ ID NO:157), AYASN* (SEQ ID NO:158), MAVAA (SEQ ID NO:159), MAVAM (SEQ ID NO:160), MAVAN* (SEQ ID NO:161), MAVVN* (SEQ ID NO:162), MAVSN* (SEQ ID NO:163), MAAAA (SEQ ID NO:164), MAAAM (SEQ ID NO:165), MAAAN* (SEQ ID NO:166), MAAVW (SEQ ID NO:167), MAAVA (SEQ ID NO:168), MAAVM (SEQ ID NO:169), MAAVN* (SEQ ID NO:170), MAASN* (SEQ ID NO:171), MVVAW (SEQ ID NO:172), MVVAA (SEQ ID NO:173), MVVAM (SEQ ID NO:174), MVVAN* (SEQ ID NO:175), MVVVM (SEQ ID NO:176), MVVVN* (SEQ ID NO:177), MVVSN* (SEQ ID NO:178), MVAAM (SEQ ID NO:179), MVAAN* (SEQ ID NO:180), MVAVM (SEQ ID NO:181), MVAVN* (SEQ ID NO:182), MVASN* (SEQ ID NO:183), MSVAW (SEQ ID NO:184), MSVAA (SEQ ID NO:185), MSVAM (SEQ ID NO:186), MSVAN* (SEQ ID NO:187), MSVVW (SEQ ID NO:188), MSVVA (SEQ ID NO:189), MSVVM (SEQ ID NO:190), MSVVN* (SEQ ID NO:191), MSVSM (SEQ ID NO:192), MSVSN* (SEQ ID NO:193), MSAAW (SEQ ID NO:194), MSAAA (SEQ ID NO:195), MSAAM (SEQ ID NO:196), MSAAN* (SEQ ID NO:197), MSAVW (SEQ ID NO:198), MSAVA (SEQ ID NO:199), MSAVM (SEQ ID NO:200), MSAVN* (SEQ ID NO:201), MSASM (SEQ ID NO:202), MSASN* (SEQ ID NO:203), MYVAW (SEQ ID NO:204), MYVAA (SEQ ID NO:205), MYVAM (SEQ ID NO:206), MYVAN* (SEQ ID NO:207), MYVVW (SEQ ID NO:208), MYVVA (SEQ ID NO:209), MYVVM (SEQ ID NO:210), MYVVN* (SEQ ID NO:211), MYVSW (SEQ ID NO:212), MYVSA (SEQ ID NO:213), MYVSM (SEQ ID NO:214), MYVSN* (SEQ ID NO:215), MYAAW (SEQ ID NO:216), MYAAA (SEQ ID NO:217), MYAAM (SEQ ID NO:218), MYAAN* (SEQ ID NO:219), MYAVW (SEQ ID NO:220), MYAVA (SEQ ID NO:221), MYAVM (SEQ ID NO:222), MYAVN* (SEQ ID NO:223), MYASW (SEQ ID NO:224), MYASA (SEQ ID NO:225), MYASM (SEQ ID NO:226), or MYASN* (SEQ ID NO:227), wherein N*=norleucine, and wherein either end of said recognition sequence can be a N-terminus.

Embodiment 3

The cyclic compound of embodiment 1, wherein one R is:

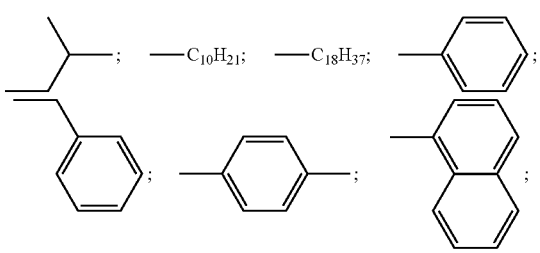

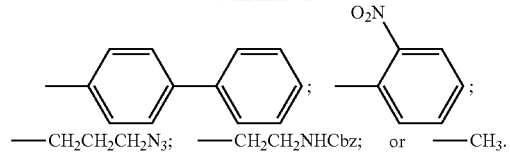

Embodiment 4

The cyclic compound of embodiment 1, wherein R is H, $C_1$-$C_{30}$ alkyl, $C_2$-$C_{30}$ alkenyl, $C_2$-$C_{30}$ alkynyl, $C_6$-$C_{14}$ aryl, $C_7$-$C_{30}$ arylalkyl, $C_8$-$C_{30}$ arylalkenyl, $C_8$-$C_{30}$ arylalkynyl, hydroxy, $C_1$-$C_{30}$ alkoxy, $C_6$-$C_{14}$ aryloxy, $C_7$-$C_{30}$ arylalkyloxy, $C_2$-$C_{30}$ alkenyloxy, $C_2$-$C_{30}$ alkynyloxy, $C_8$-$C_{30}$ arylalkenyloxy, $C_8$-$C_{30}$ arylalkynyloxy, $CO_2H$, $C_2$-$C_{30}$ alkylester, $C_7$-$C_{15}$ arylester, $C_8$-$C_{30}$ alkylarylester, $C_3$-$C_{30}$ alkenylester, $C_3$-$C_{30}$ alkynylester, $NH_2$, $C_1$-$C_{30}$ alkylamino, $C_6$-$C_{14}$ arylamino, $C_7$-$C_{30}$ (arylalkyl)amino, $C_2$-$C_{30}$ alkenylamino, $C_2$-$C_{30}$ alkynylamino, $C_8$-$C_{30}$ (arylalkenyl)amino, $C_8$-$C_{30}$ (arylalkynyl)amino, $C_2$-$C_{30}$ dialkylamino, $C_{12}$-$C_{28}$ diarylamino, $C_4$-$C_{30}$ dialkenylamino, $C_4$-$C_{30}$ dialkynylamino, $C_7$-$C_{30}$ aryl(alkyl)amino, $C_7$-$C_{30}$ di(arylalkyl)amino, $C_8$-$C_{30}$ alkyl(arylalkyl)amino, $C_{15}$-$C_{30}$ aryl(arylalkyl)amino, $C_8$-$C_{30}$ alkenyl(aryl)amino, $C_8$-$C_{30}$ alkynyl(aryl)amino $C(O)NH_2$ (amido), $C_2$-$C_{30}$ alkylamido, $C_7$-$C_{14}$ arylamido, $C_8$-$C_{30}$ (arylalkyl)amido, $C_2$-$C_{30}$ dialkylamido, $C_{12}$-$C_{28}$ diarylamido, $C_8$-$C_{30}$ aryl(alkyl)amido, $C_{15}$-$C_{30}$ di(arylalkyl)amido, $C_9$-$C_{30}$ alkyl(arylalkyl)amido, $C_{16}$-$C_{30}$ aryl(arylalkyl)amido, thiol, $C_1$-$C_{30}$ hydroxyalkyl, $C_6$-$C_{14}$ hydroxyaryl, $C_7$-$C_{30}$ hydroxyarylalkyl, $C_3$-$C_{30}$ hydroxyalkenyl, $C_3$-$C_{30}$ hydroxyalkynyl, $C_8$-$C_{30}$ hydroxyarylalkenyl, $C_8$-$C_{30}$ hydroxyarylalkynyl, $C_3$-$C_{30}$ polyether, $C_3$-$C_{30}$ polyetherester, $C_3$-$C_{30}$ polyester, $C_3$-$C_{30}$ polyamino, $C_3$-$C_{30}$ polyaminoamido, $C_3$-$C_{30}$ polyaminoether, $C_3$-$C_{30}$ polyaminoester, $C_3$-$C_{30}$ polyamidoester, $C_3$-$C_{30}$ alkylsulfonic acid, $C_3$-$C_{30}$ alkylsulfonate salt, $C_1$-$C_{30}$ carboxylate salt, $C_1$-$C_{30}$ thiocarboxylate salt, $C_1$-$C_{30}$ dithiocarboxylate salt, or $C_3$-$C_{30}$ alkyl$C_1$-$C_4$ trialkyammonium salt, wherein any carbon can be further substituted with any carbon can be substituted with a hydroxy, chloro, bromo, iodo, nitro, or carboxylic acid.

Embodiment 5

The cyclic compound of any preceding embodiment, wherein said carrying agent comprises an amino acid, oligo(amino acid), poly(amino acid) or protein.

Embodiment 6

The cyclic compound of any preceding embodiment, wherein said carrying agent comprises an antibody, or an Fc portion of an antibody, or an antigen-binding fragment of an antibody.

Embodiment 7

The cyclic compound of any preceding embodiment, wherein said carrying agent is a monoclonal antibody (mAb), or an Fc portion of a mAb, or an antigen binding fragment of a mAb, comprising a selenocysteine residue.

Embodiment 8

The cyclic compound of any preceding embodiment, wherein said carrying agent is a monoclonal antibody (mAb), or an Fc portion of a mAb, or antigen binding fragment of a mAb, comprising a C-terminal selenocysteine residue.

Embodiment 9

The cyclic compound of any preceding embodiment, wherein said carrying agent specifically binds to a cell surface antigen.

Embodiment 10

The cyclic compound of any preceding embodiment, wherein said carrying agent specifically binds to a tumor associated antigen.

Embodiment 11

The cyclic compound of any preceding embodiment, wherein said carrying agent specifically binds to one or more antigens selected from among CD138, CD44, alpha4 integrin, alpha3 integrin, alpha6 integrin, EGFR, tumor suppressor cell antigen, cytotoxic T cell antigen, 17-1A, 707-AP, AFP, Annexin II, ART-4, BAGE, BAGE-1, β-catenin, BCG, bcr/abl, Bcr/abl e14a2 fusion junction, bcr-abl (b3a2), bcr-abl (b3a2), bcr-abl p190 (e1a2), bcr-abl p210 (b2a2), bcr-abl p210 (b3a2), bcr-abl p210 (b3a2), bullous pemphigoid antigen-1, CA19-9, CA125, CA215, CAG-3, CAMEL, Cancer-testis antigen, Caspase-8, CCL3, CCL4, CD16, CD20, CD3, CD30, CD55, CD63, CDC27, CDK-4, CDR3, CEA, cluster 5, cluster-5A, cyclin-dependent kinase-4, Cyp-B, DAM-10, DAM-6, Dek-cain, E7, EGFRvIII, EGP40, ELF2 M, EpCAM, FucGM1, G250, GA733, GAGE, GAGE-1-8, gastrin cancer associated antigen, GD2, GD3, globoH, glycophorin, GM1, GM2, GM3, GnTV, Gn-T-V, gp100, Her-2/neu, HERV-K-ME, high molecular weight-associated antigen, high molecular weight proteo-glycan (HMPG), HPV-16 E6, HPV-16 E7, HPVE6, HSP70-2M, HST-2, hTERT, human chorionic gonadotropin (HCG), Human milk fat globule (HMFG), iCE, KIAA0205, KK-LC-1, KM-HN-1, L6, LAGE-1, Lcose4Cer, LDLR/FUT, Lewis A, Lewis v/b, M protein, MAGE-1, MVC, MAGE-A1-12, MAGE-C2, MAHGE-3, MART-1/Melan-A, MC1R, ME491, MUC1, MUC2, mucin, MUM-1, MUM-2, MUM-3, mutated p53, Myosin, MZ2-E, N9 neuraminidase, NA88, NA88-A, nasopharyngeal carcinoma antigen, NGA, NK1/c-3, Novel bcr/ablk fusion BCR exons 1, 13, 14 with ABL exons 4, NY-ESO-1/LAGE-2, NY-ESO-1b, OC125, osteosarcoma associated antigen-1, P15, p190 mimor bcr-abl (e1a2), p53, Pml/RARα, Polysialic acid, PRAME, PSA, PSM, RU1, RU2, SAGE, SART-1, SART-2, SART-3, Sialyl LeA, Sp17, SSX-2, SSX-4, surface immunoglobulin, TAG-1, TAG-2, TEL/AML1, TPI, TRAG-3, TRP-1(gp75), TRP-2, TRP2-INT2, hTRT, tumor associated glycoprotein-72 (TAG-72), tyrosinase, u-PA, WT1, and XAGE-1b, or an immunogenic fragment of any of the foregoing antigens.

Embodiment 12

The cyclic compound of embodiment 1, wherein the structure is:

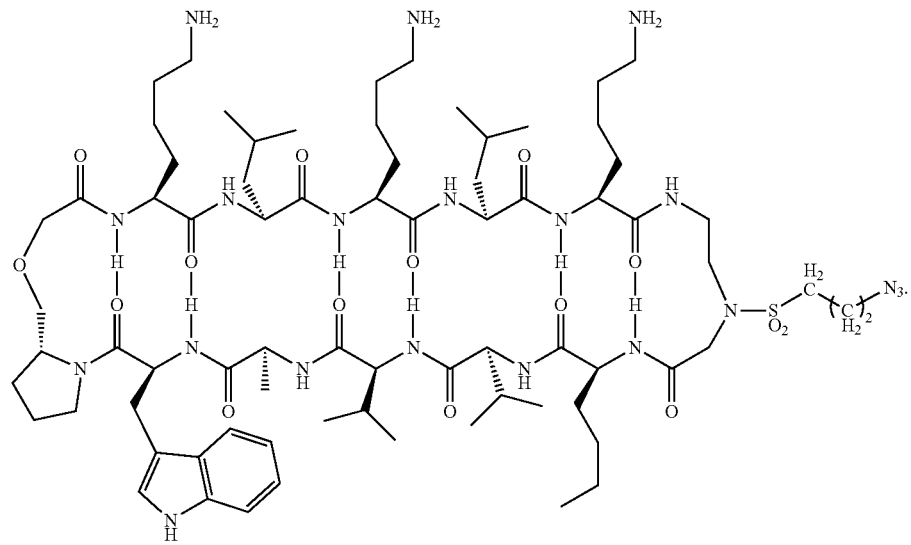

Embodiment 13
The cyclic compound of embodiment 1, wherein the structure is:
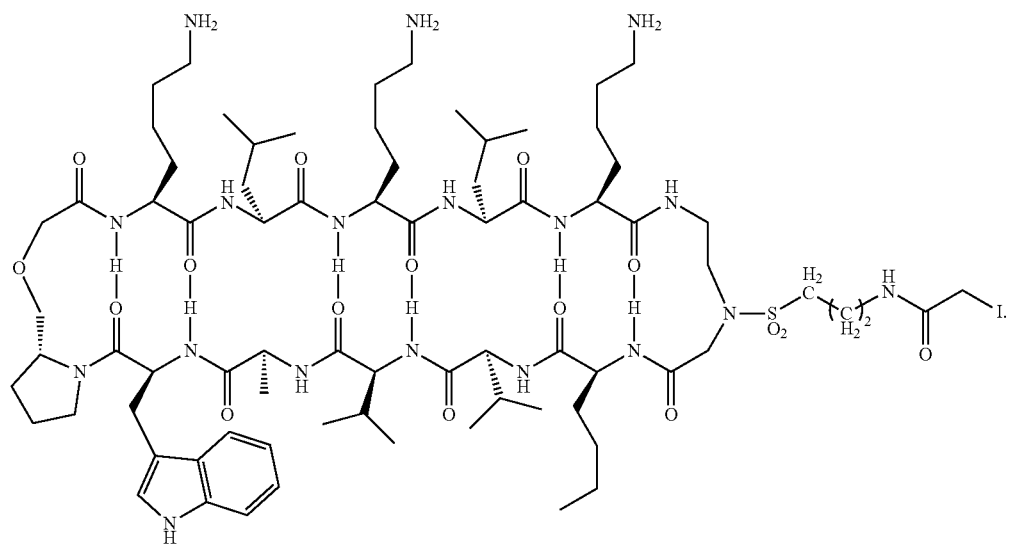
35
Embodiment 14
The cyclic compound of embodiment 1, wherein the structure is:
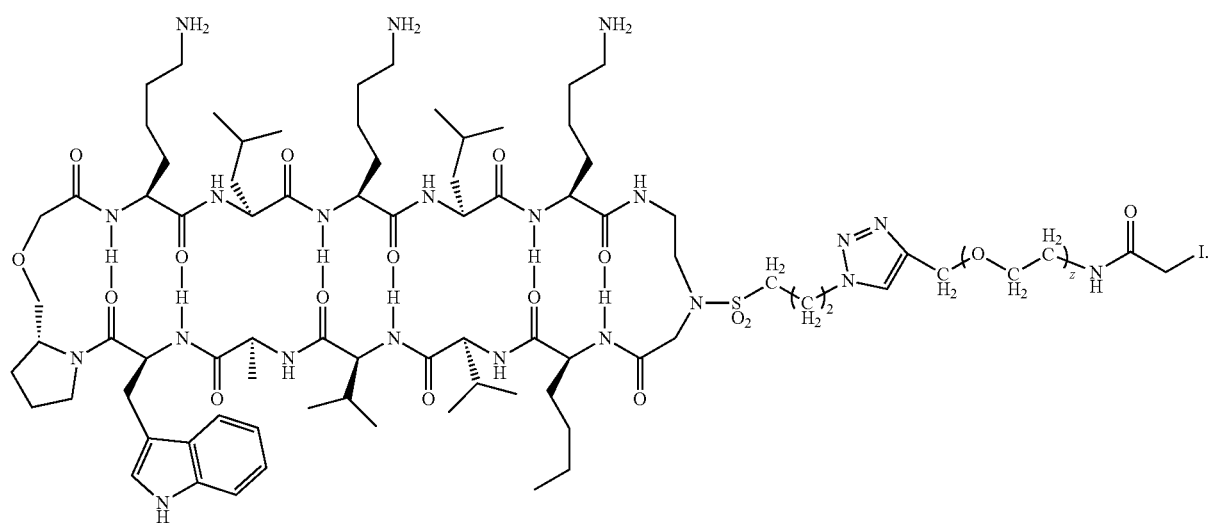

Embodiment 15
The cyclic compound of embodiment 1, wherein the structure is:
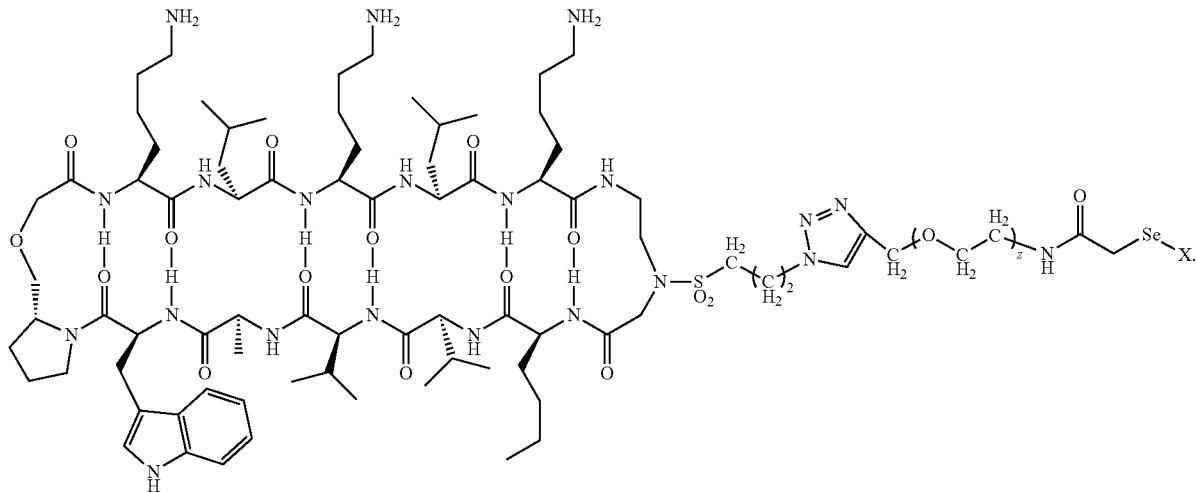
Embodiment 16
The cyclic compound of embodiment 1, wherein the structure is:
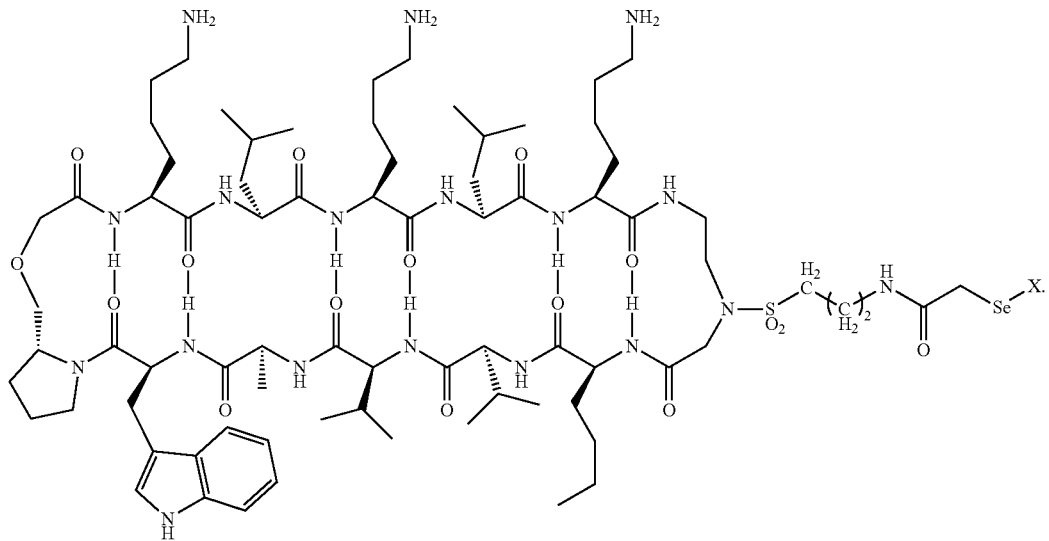
Embodiment 17
A linker, comprising:
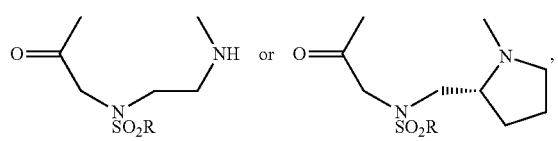
wherein R is
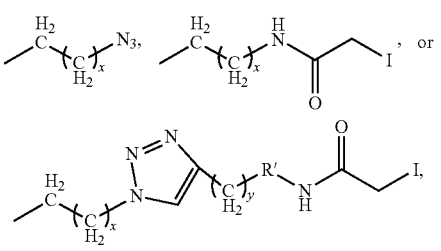

wherein x is 1-12, y is 1-12, R' is

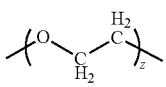

and z is 1 to 20.

Embodiment 18

A method of preparing a carrying agent:cyclic compound adduct, comprising:

providing a cyclic compound comprising a recognition sequence and a non-recognition sequence, wherein said recognition sequence comprises at least four amino acids, wherein said non-recognition sequence comprises at least four amino acids, and wherein said recognition sequence is joined to said non-recognition sequence by a first linker and a second linker, wherein at least one of said first linker and said second linker is:

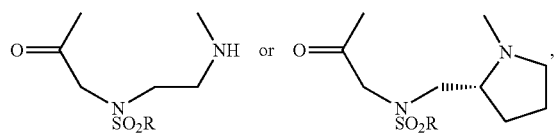

wherein R is

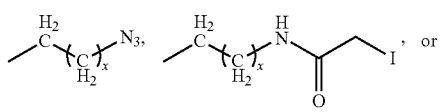

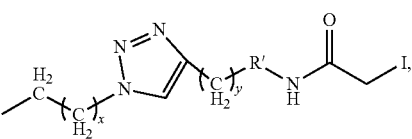

wherein x is 1-12, y is 1-12, R' is

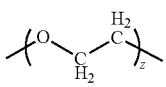

and z is 1 to 20;

providing a carrying agent X comprising a selenocysteine residue; and combining said carrying agent and said cyclic compound in an aqueous solution.

Embodiment 19

The method of preparing a carrying agent:cyclic compound adduct of embodiment 18, wherein said aqueous solution comprises dithiothreitol (DTT) and wherein said aqueous solution has an acidic pH.

Embodiment 20

The method of preparing a carrying agent:cyclic compound adduct of embodiment 19, wherein said pH is 4-6 and the concentration of DTT is 0.1-1 mM.

Embodiment 21

The method of preparing a carrying agent:cyclic compound adduct of claim 18, wherein the cyclic compound comprises:

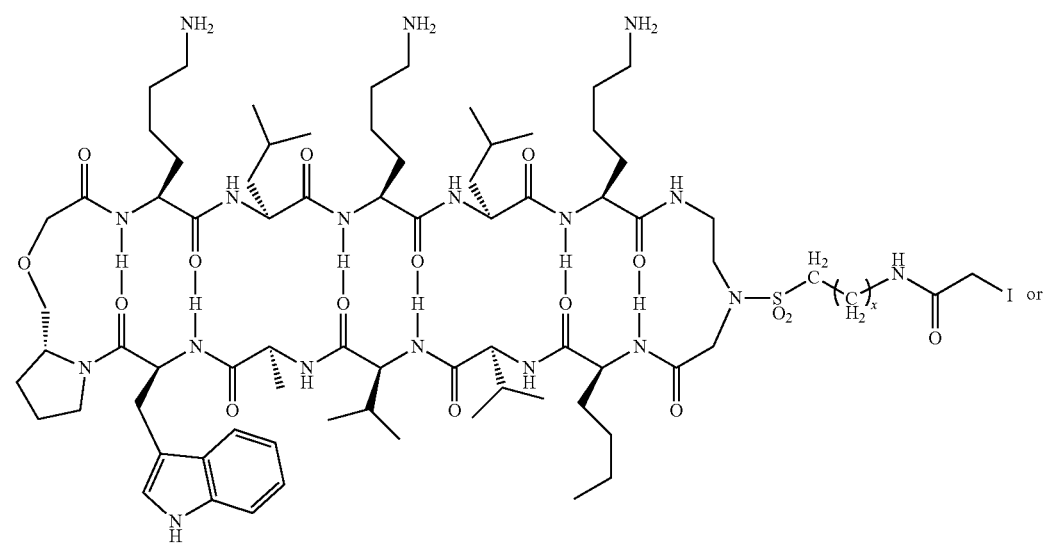

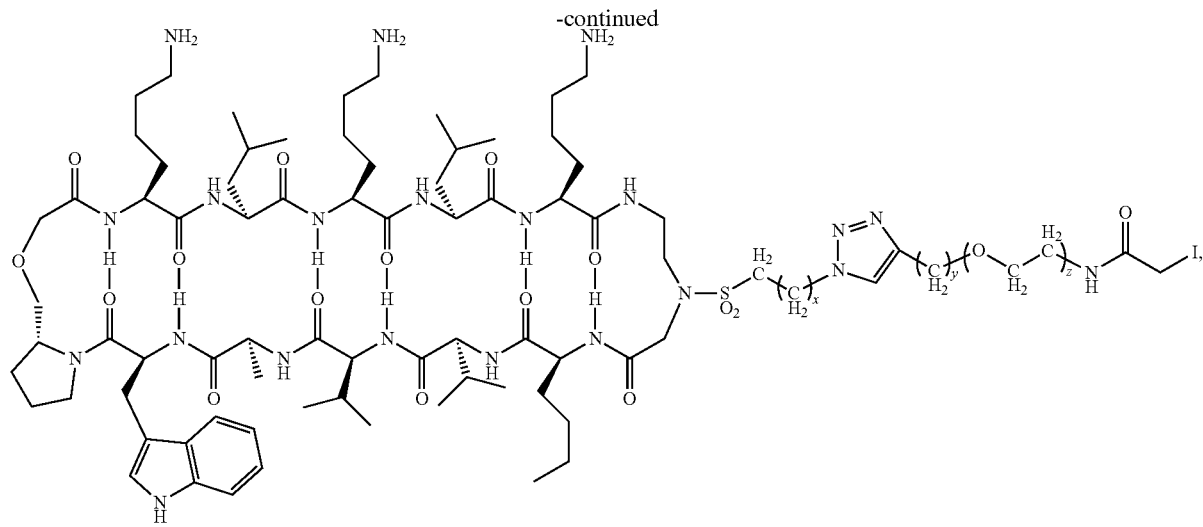

wherein x is 1-12, y is 1-12, and z is 1.

Embodiment 22

The method of preparing a carrying agent:cyclic compound adduct according to embodiment 18, wherein the carrying agent comprises an oligo(amino acid), poly(amino acid) or protein comprising a selenocysteine residue.

Embodiment 23

The method of preparing a carrying agent:cyclic compound adduct according to embodiment 18, wherein said carrying agent X is a monoclonal antibody (mAb) comprising a selenocysteine residue Embodiment 24. The method of preparing a carrying agent:cyclic compound adduct according to embodiment 18, wherein said carrying agent X is the modified antibody Fc-Sec-His having the sequence: EPKSSDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALH NHYTQKSLSLSPGAUHHHHHH (SEQ ID NO:228) where U is the single letter amino acid code for selenocysteine.

Embodiment 25

The method of preparing a carrying agent:cyclic compound adduct according to embodiment 18, wherein said carrying agent X is a targeting agent that is the modified antibody Anti-CD138-scFv-Fc-Sec-His having the sequence: DIQMTQSTSSLSASLGDRVTISCSASQGINNYLNWYQQKPDGTVELLIYYTSTLQSGVPSRFSGSGSGTDYSLTISNLEPEDIGTYYCQQYSKLPRTFGGGTKLEIKGGGGS GGGGSGGGGSQVQLQQSGSELMMPGASVKISCKATGYTFSNYWIEWVKQRPGHGLEWIGEILPGTGRTIYNEKFKGKATFTADISSNTVQMQLSSLTSEDSAVYYCARR DYYGNFYYAMDYWGQGTSVTVSSEPKSSDKTHTCPPCPAPELLGGPSVFLFPPKP KDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGAUHHHHHH (SEQ ID NO:229) where U is the single letter amino acid code for selenocysteine.

Embodiment 26

The method of preparing a carrying agent agent:cyclic compound adduct according to embodiment 18, wherein said carrying agent X comprises a residue of selenocysteine having a

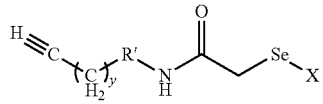

and wherein said cyclic compound comprises:

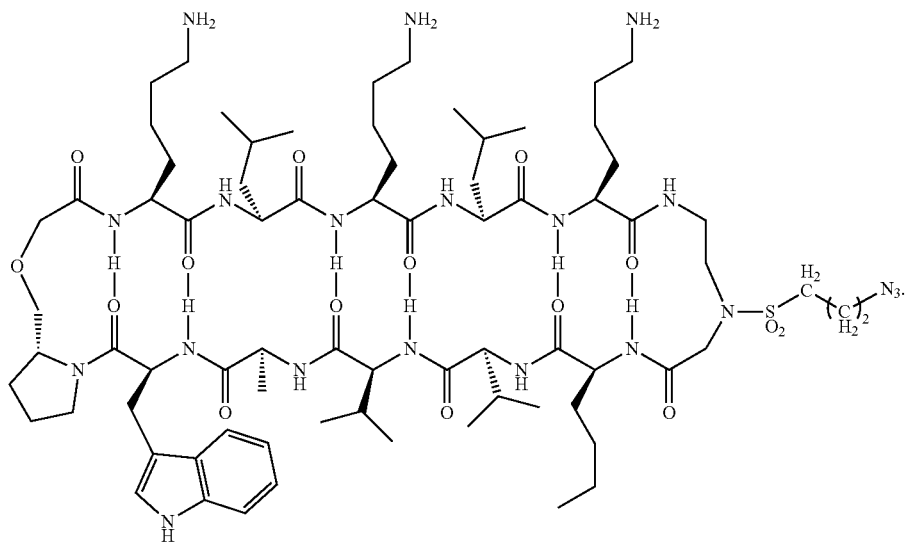

Embodiment 27

A method for treating a disorder in a subject, comprising administering an effective amount of a cyclic compound of any one of embodiments 1 to 16 to the subject.

Embodiment 28

The method of embodiment 27, wherein the subject is human.

Embodiment 29

The method of embodiment 27, wherein the disorder is a proliferation disorder, bone deficiency, or autoimmune disease.

Embodiment 30

The method of embodiment 28, wherein the proliferation disorder is myeloma or another malignancy.

Embodiment 31

The method of any one of embodiments 27 to 30, wherein the cyclic compound is administered in a composition further comprising a pharmaceutically acceptable carrier.

Embodiment 32

A method of suppressing the growth of, or inducing apoptosis in, cells, comprising contacting the cells with an effective amount of a cyclic compound of any one of embodiments 1 to 16.

Embodiment 33

The method of embodiment 32, wherein the cyclic compound is in a composition further comprising a pharmaceutically acceptable carrier.

Embodiment 34

The method of embodiment 32 or 33, wherein said contacting is carried out in vivo.

Embodiment 35

The method of any one of embodiments 32 to 34, wherein the cells are human cells.

Embodiment 36

The method of any one of embodiments 32 to 35, wherein the cells are myeloma cells or other malignant cells.

Embodiment 37

A composition comprising a cyclic compound of any one of embodiments 1 to 16; and a pharmaceutically acceptable carrier.

Materials and Methods

Outline of Selenocysteine Monoclonal Antibody (mAb) Expression and Purification.
1. pCEP4-mAb (Fc, αCD138) containing vectors transfected into 293F (Fc only) and
293P (both) HEK cells with Lipofectamine 2000 reagent.
2. Cells cultured in protein-free Freestyle Expression 293 Medium and supplemented with 1 μM Na2 SeO3
3. mAbs were collected (3×) every 3 days.
4. mAbs concentrated using 10-kDa cutoff ultrafiltration device under nitrogen gas.
5. mAbs purified via recombinant Protein G column and then IMAC HisTrap column.
SDS-PAGE Characterization.
1. 3 μg, 20 μl aliquots diluted in PBS. 1 μl (v/v) 1% β-mercaptoethanol added to reducing samples
2. Loaded onto NuPAGE Novex Bis-Tris 4-12% gradient gel and stained with SimplyBlue SafeStain.

Binding Confirmation.

Incubations for APC fluorochrome analysis were 30 min for each antibody at rt followed by (2×) PBS washings.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Production and Characterization of Cyclic Peptide Conjugates

Cloning and production of the antibodies were performed with designed expression cassettes in pCEP4 vector, which yielded approximately 2 mg of both Fc-Sec-His6 and scFv-Fc-αCD138 over a period of 3 weeks after a series of pilot studies. Utilizing the selective selenocysteine incorporation methodology (FIG. 2), MTI-101 was conjugated to each antibody in a 1:1 DAR with >90% yield. The antibody drug conjugates (ADCs) were then further characterized by reduced and non-reduced SDS-PAGE to verify putative MTI-101 incorporation.

The inventors investigated the conjugation of an iodoacetamide derivative of MTI-101 (FIG. 1) to two different carrier proteins; (i) the Fc fragment of human IgG1 and (ii) the scFv-Fc format of chimeric mouse/human monoclonal antibody (mAb) B-B4, which binds with high affinity and specificity to human CD138. Conjugate (i) constitutes a chemically programmed antibody (Rader, C., "Chemically programmed antibodies," *Trends Biotechnol*, 2014, 32, 186-197), in which the conventional antigen binding site is replaced with a synthetic component. Conjugate (ii) is a chemically programmed bispecific antibody with conventional (anti-CD138) and synthetic (anti-CD44) antigen binding sites.

As shown in FIGS. 16 and 17, mAbs and antibody fragments can be equipped with a C-terminal selenocysteine residue, the 21st natural amino acid with unique chemical properties, and stably and site-selectively conjugated to iodoacetamide derivatives. Conditions for conjugation included a selenol pKa of about 5.2, which allows for selective conjugation in a 1:1 defined carrier:payload ratio. Compared to conventional cysteine and lysine conjugation technologies with heterogeneous drug-to-antibody ratios (DARs), defined DARs increase therapeutic indices, as these ADCs lack large batch-to-batch variability and the potential for undesired toxicity. Most importantly, this methodology provides a strategy to adjoin small molecules to mAbs and antibody fragments, which should increase the circulatory half-life of the small molecule owing to both increased size and FcRn-mediated recycling (Roopenian, D. C. and Akilesh, S., "FcRn: the neonatal Fc receptor comes of age", *Nat Rev Immunol*, 2007, 7, 715-725), and augment the potency of the small molecule by equipping it with the cytotoxic effector functions of the antibody molecule.

As described below, carrier protein Fc-Sec-His (FIG. 16), was expressed and purified as described previously (Hofer, T., et al., "An engineered selenocysteine defines a unique class of antibody derivatives", *Proc Natl Acad Sci USA*, 2008, 105, 12451-12456), and analyzed by SDS-PAGE.

Figure 3:
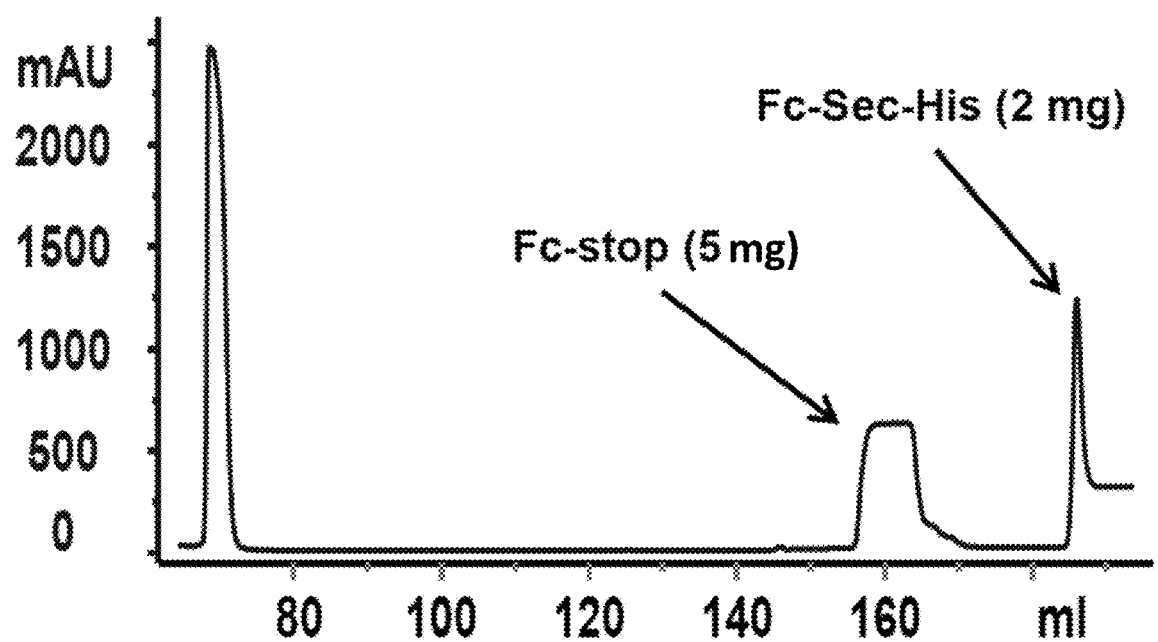
FIG. 3 shows results of Fc-Sec-His6 purification via recombinant Protein G column and IMAC HisTrap column. This demonstrates that the correct Fc-Sec-His6 mAb (with selenocysteine incorporation) was isolated with high fidelity.
Figure 4:
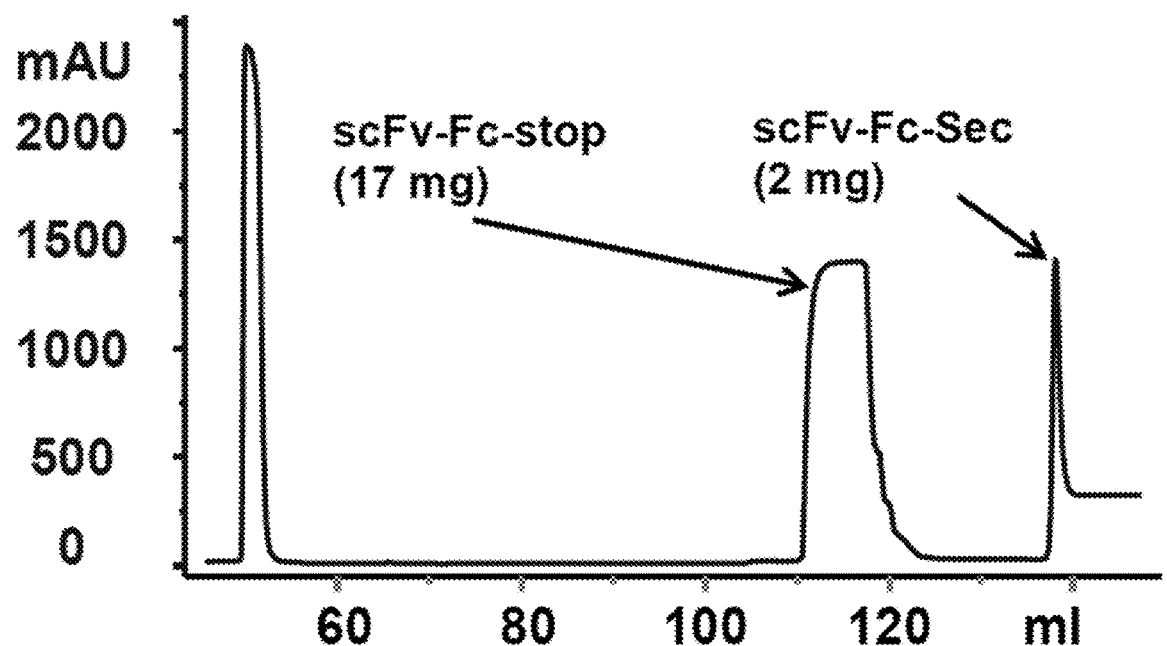
FIG. 4 shows scFv-Fc-αCD138-Sec-His6 purification via recombinant Protein G column and IMAC HisTrap column. This demonstrates that the correct scFv-Fc-αCD138-Sec-His6 mAb (with selenocysteine incorporation) was isolated with high fidelity.

Purification of Fc-Sec-His was performed by tandem Protein G affinity chromatography and immobilized metal affinity chromatography (IMAC). FIG. 3 shows the elution profile of Fc-Sec-His on a HisTrap column, which separates Fc-stop (without C-terminal selenocysteine) from Fc-Sec-His.

Figure 5:
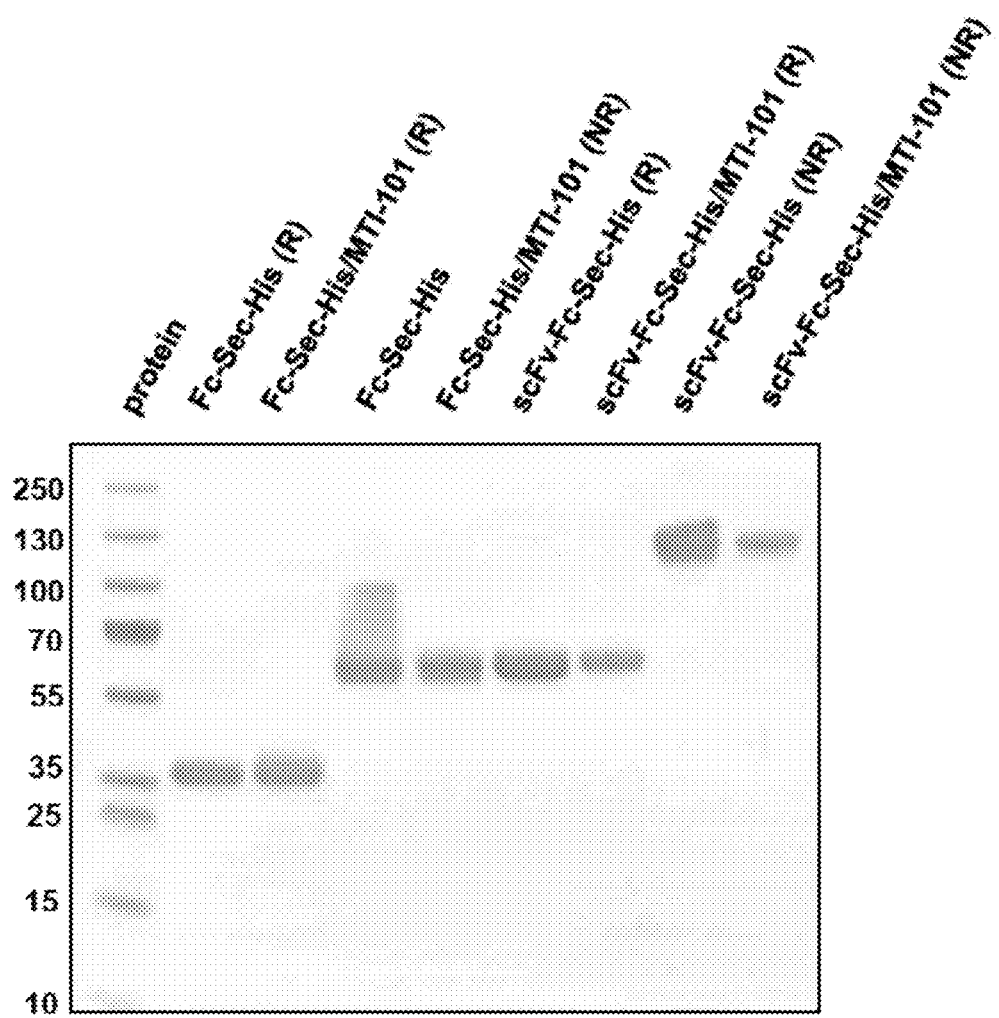
FIG. 5 shows SDS-PAGE analysis of reduced and non-reduced mAbs and mAb drug conjugates. The reducing lanes (with disulfide bridges broken) run further in their corresponding lanes (R=reducing; NR=non-reducing). Furthermore, the ADCs show slightly less movement down the lane than their selenocysteine counterparts. This shows that they are slightly heavier (since MTI-101=1.7 kDa) and verifies selective, 1:1 drug:antibody conjugation. The binding confirmation analysis also shows that the mAbs were correctly characterized.

SDS-PAGE analysis of purified Fc-Sec-His and scFc-Fc-Sec-His was carried out before and after conjugation to MTI-101-iodoacetamide. The proteins and conjugates were separated on a NuPAGE Novex Bis-Tris 4-12% gradient gel. SimplyBlue SafeStain was used to visualize the protein bands. R, reduced with β-mercaptoethanol; NR, non-reduced. Both Fc-Sec-His (~55-kD dimer) and scFv-Fc-Sec-His (~110-kD dimer) reveal the expected sizes. A slight shift is noticeable after conjugation of MTI-101-Iodoacetamide (1.7 kDa), as shown in FIG. 5.

Next, the inventors confirmed the binding of the Fc-Sec-His/MTI-101 conjugate to the cell surface of human MM cell lines U266 and H929 by flow cytometry (FIGS. 6A-6B), demonstrating successful chemical programming. APC flow cytometry (FCM) and human-CD44 ELISA were employed to confirm mono-affinity of Fc-Sec/MTI-101 to CD44. Further APC-FCM and human-CD138 ELISA data confirmed strong mono-affinity of the αCD138 ADC to CD138.

Figure 8A:
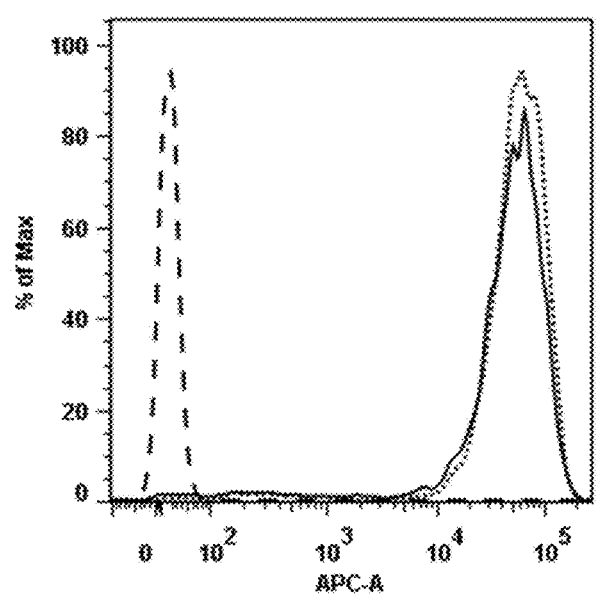
FIGS. 8A-8B show binding of scFv-Fc-Sec-His/MTI-101 to the MM cell surface (U266 cells in FIG. 8A; H929 cells in FIG. 8B). dashed, unstained cells; dotted, scFv-Fc-Sec-His (3 µg); solid, scFv-Fc-Sec-His/MTI-101 (3 µg). APC-conjugated goat anti-human IgG (Fcγ-specific) was used for detection.
Figure 8B:
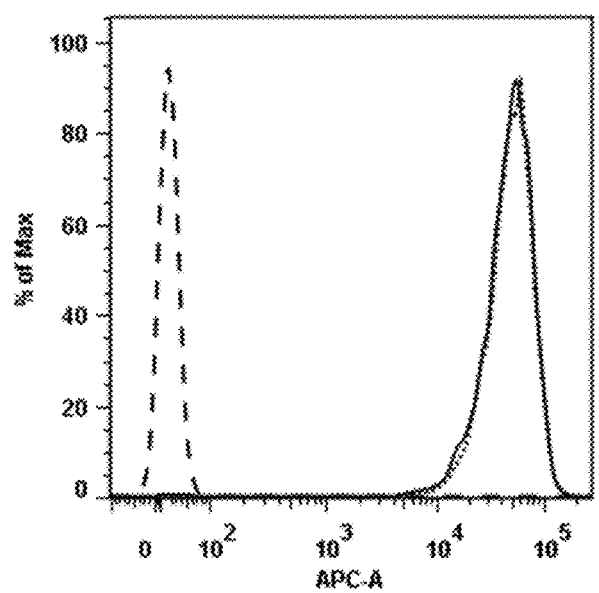
Figure 9:
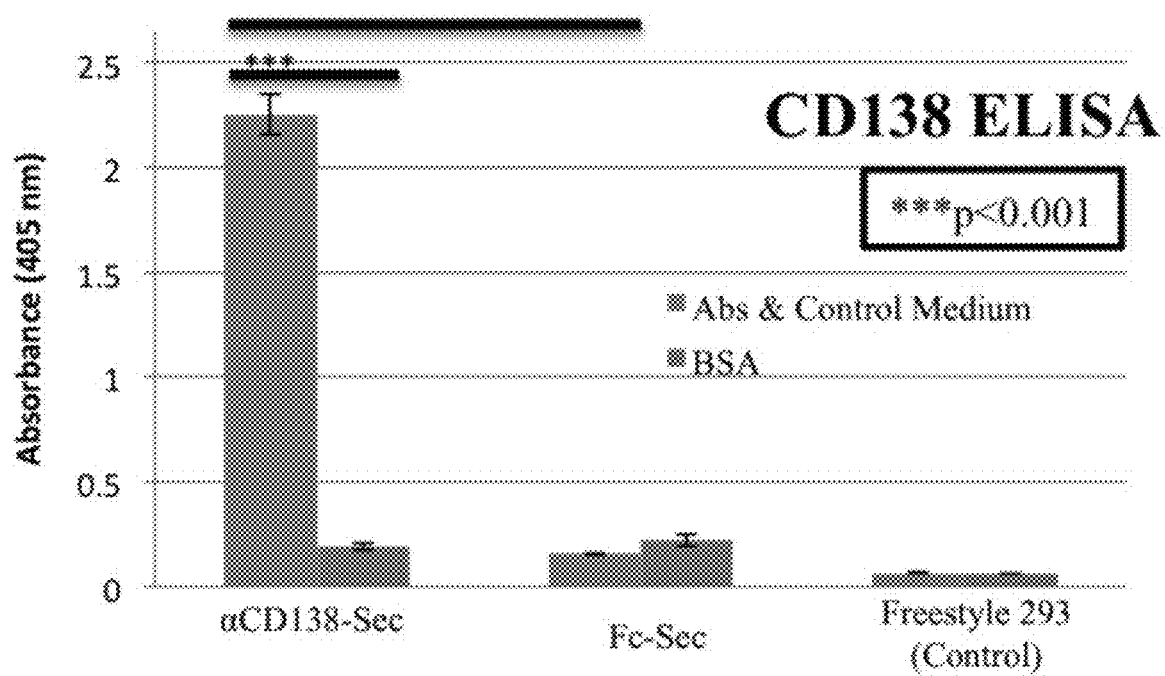
FIG. 9 shows ELISA binding to CD138 target.

Due to the dual expression of CD44 and CD138 on the myeloma cell surface, demonstrating successful chemical programming of the scFv-Fc-Sec/MTI-101 conjugate by flow cytometry is complicated. However, the inventors showed that both anti-CD138-scFv-Fc-Sec-His and anti-CD138-scFv-Fc-Sec-His/MTI-101 bound equally well to the cell surface of human MM cell lines U266 and H929, which express CD138 at high cell surface densities (FIGS. 8A-8B). Thus, conjugated MTI-101 does not interfere with CD138 binding. The development of suitable assays demonstrating simultaneous binding of anti-CD138-scFv-Fc-Sec-His/MTI-101 to CD138 and CD44 is ongoing.

Figure 6A:
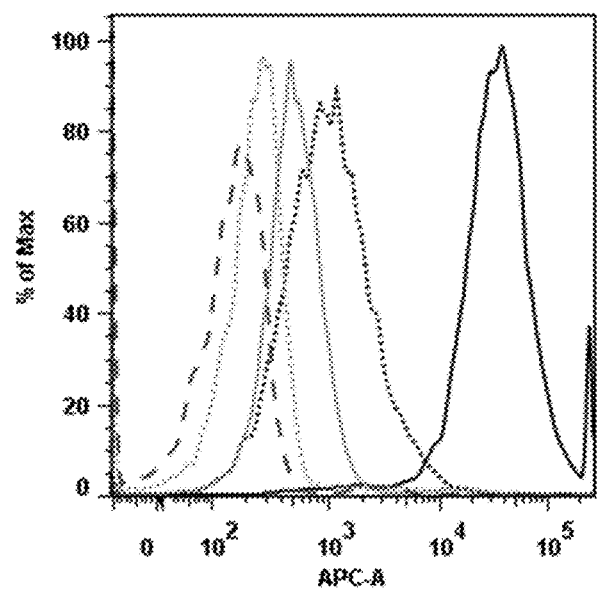
FIGS. 6A-6B show binding of Fc-Sec-His/MTI-101 to the MM cell surface (U266 cells in FIG. 6A; H929 cells in FIG. 6B). Dashed, unstained cells; dotted gray, Fc-Sec-His (0.3 µg); solid gray, Fc-Sec-His (3 µg); dotted black, Fc-Sec-His/MTI-101 (0.3 µg); solid black, Fc-Sec-His/MTI-101 (3 µg). APC-conjugated goat anti-human IgG (Fcγ-specific) was used for detection.
Figure 6B:
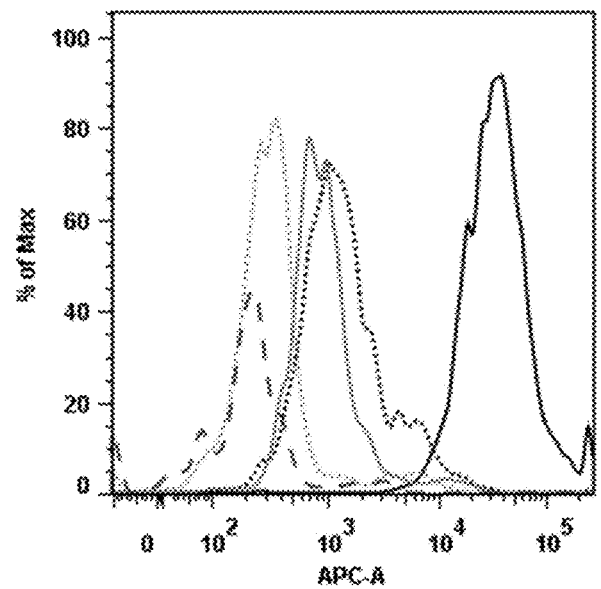
Figure 7:
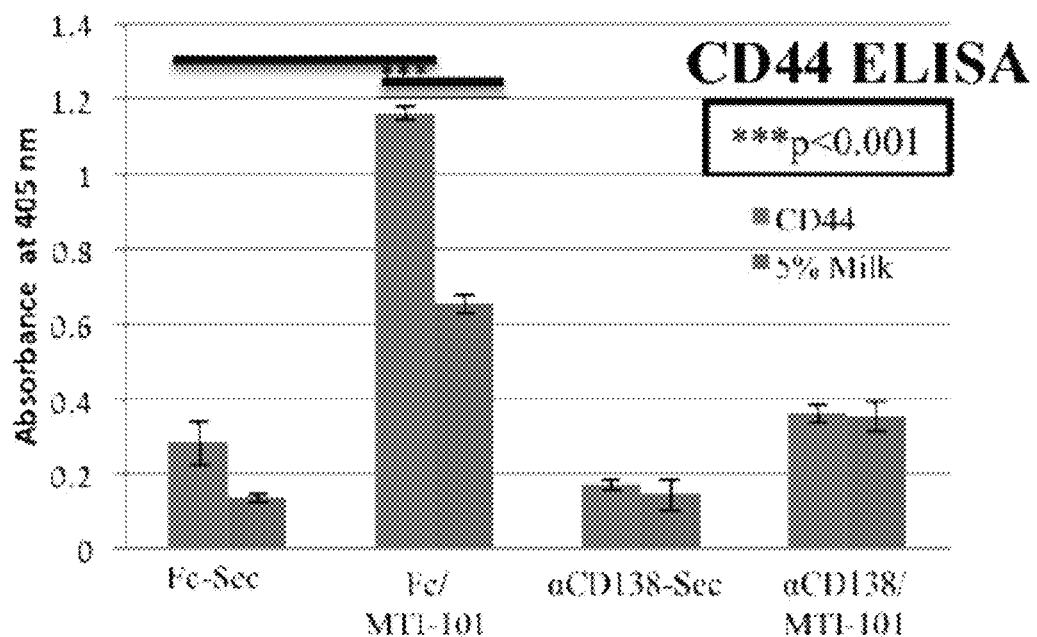
FIG. 7 shows ELISA binding to CD44 target.
Figure 11:
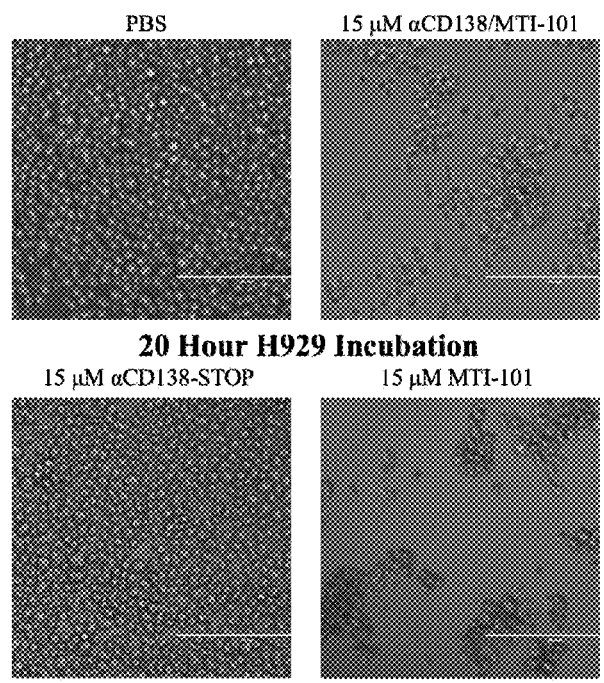
FIG. 11 shows a comparison of H929 multiple myeloma cells under microscopy.

Despite inconclusive bivalent data from FIGS. 6A-6B, FIG. 11 demonstrates cross-coupling and death of H929 cells analogously to MTI-101 but not the STOP mAb, strongly suggesting dual targeting in vitro. It is possible that the large relative size and mass of scFv-Fc-αCD138 against MTI-101 (110 vs. 1.7 kDa) induces steric hindrance from CD44 binding when plated in ELISA.

Significant in vitro killing of MM cell lines was shown in the 15-36 μM range for both ADCs using FCM FSC-A/SSC-A and digital microscopy. When overlaid with free MTI-101 and the iodoacetamide adduct titration data, the ADCs demonstrate increased potency via conjugation. Specifically, the inventors tested the cytotoxicity of Fc-Sec-His/MTI-101 (FIGS. 12A-12H) and anti-CD138-scFv-Fc-Sec-His/MTI-101 (FIGS. 14A-14D) toward MM cell lines U266 and H929 in vitro. The cells were incubated with the conjugates and negative and positive controls for 1 hour at 37° C. followed by propidium iodide (PI) staining and flow cytometry analysis using FSC/SSC scatter densities and fluorescence to distinguish live and dead cells. Whereas Fc-stop and anti-CD138-scFv-Fc-stop revealed no cytotoxicity when compared to medium alone (negative control), Fc-Sec-His/MTI-101, anti-CD138-scFv-Fc-Sec-His/MTI-101, and free MTI-101 clearly killed both U266 and H929 cells. Light microscopy confirmed the MTI-101-dependent cytotoxicity of both conjugates.

Figure 13:
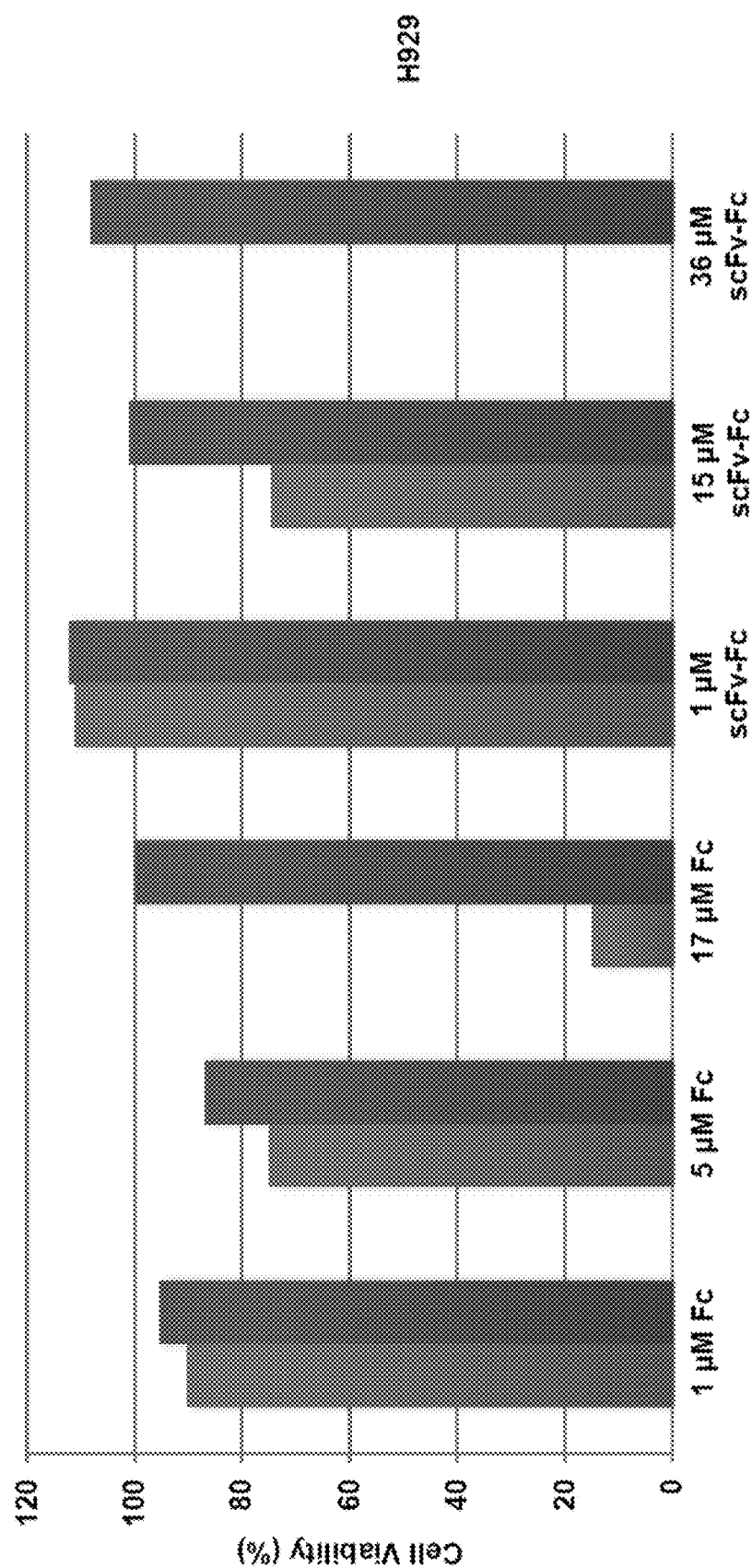
FIG. 13 shows concentration-dependent cytotoxicity of Fc-Sec-His/MTI-101 and anti-CD138-scFv-Fc-Sec-His/MTI-101 toward H929 cells. Blue columns (left bar at each concentration) show the cytotoxicity of the indicated MTI-101 conjugates; red columns (right bar at each concentration) show the corresponding stop proteins at the same concentrations.
Figure 15:
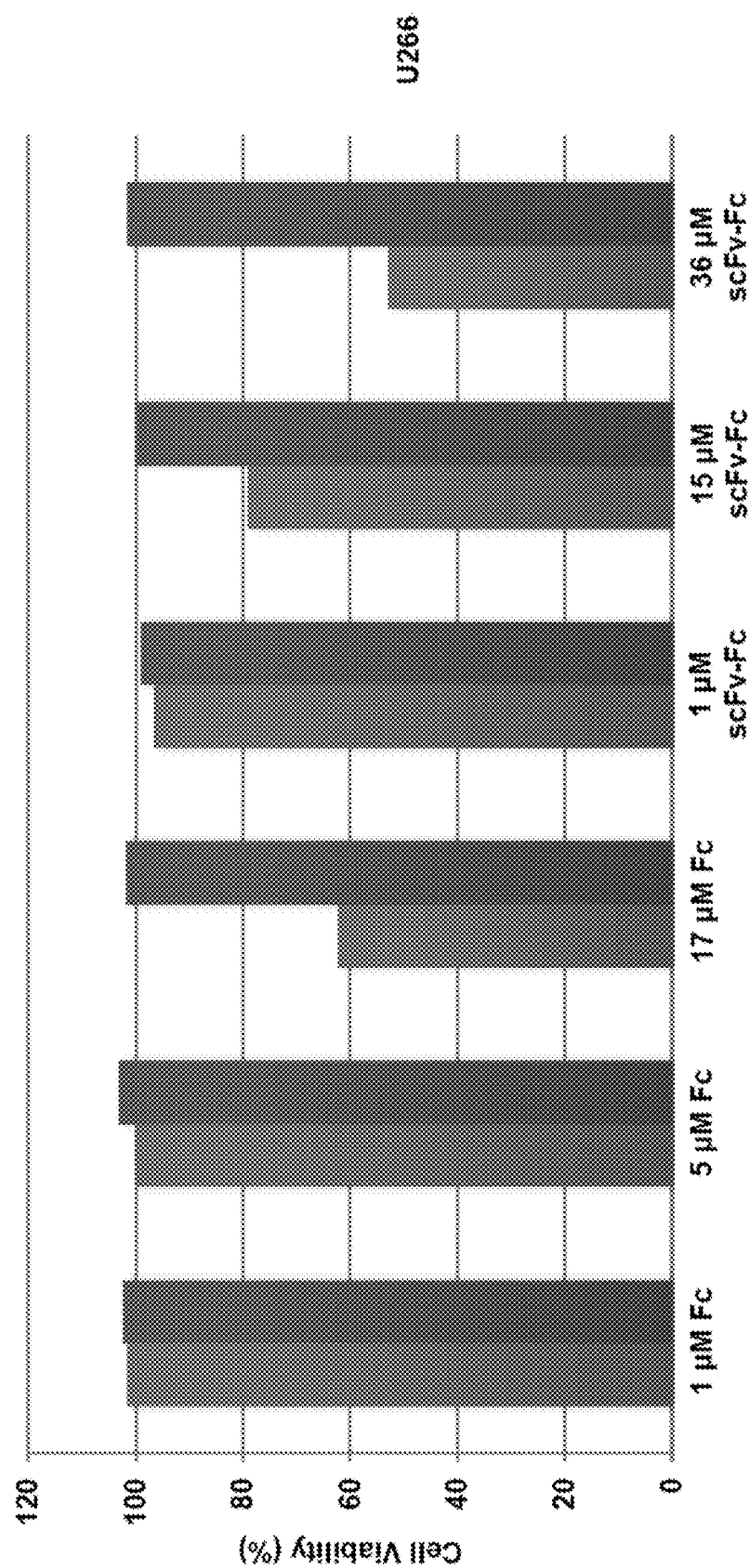
FIG. 15 shows concentration-dependent cytotoxicity of Fc-Sec-His/MTI-101 and anti-CD138-scFv-Fc-Sec-His/

Further experiments revealed that the killing is concentration-dependent with IC50s in the 10-50 μM range depending on conjugate and cell line (FIGS. 13 and 15).

Figure 10:
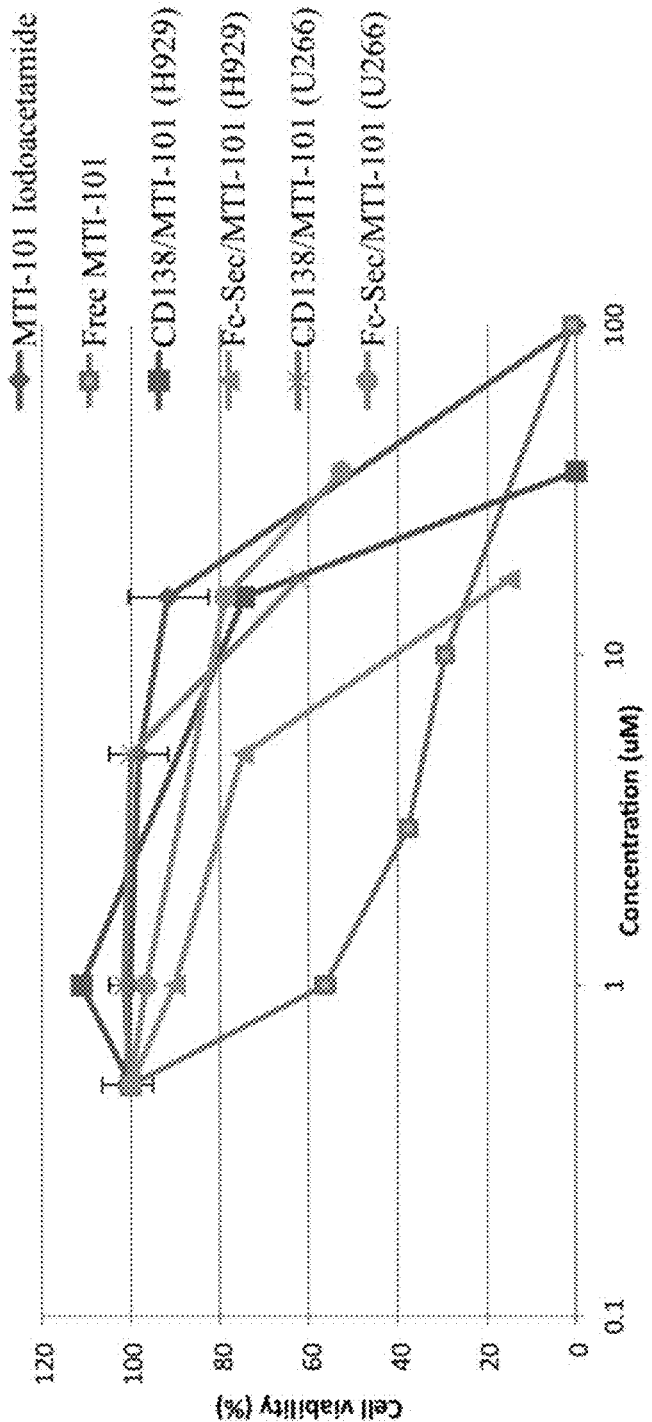
FIG. 10 shows normalized viability of H929 multiple myeloma cells across antibody drug conjugates (ADCs) and drug titrations.

The overall potency of the cyclic peptide conjugates showed an increase in cytotoxicity relative to the given MTI-101 iodoacetamide adduct (FIG. 10).

Under microscopy (see FIG. 11), the ADCs showed cell cross-linking and coagulation, which is in agreement with the action of the drug alone. This confirms both proper conjugation and can serve as a visual indicator of previous and concurrent cell death. Furthermore, the ADCs showed very potent cytotoxicity with little STOP effects when cell viability was compared via flow cytometry, in FIGS. 12A-12H, 13, 14A-14D, and 15.

The inventors then tested the cytotoxicity of Fc-Sec-His/MTI-101 in vivo, utilizing the 5TGM1 murine model (Garrett, I. R., et al., "A murine model of human myeloma bone disease. *Bone,* 1997, 20, 515-520). This is an excellent immune competent MM model in which drug response is monitored in the confines of the bone marrow microenvironment. The model demonstrates tumor burden in the bone and bone lesions typical of the clinical course of the disease. 5TGM1 cells ($1 \times 10^6$ in 100 μL of PBS) were injected intravenously (i.v.) into the tail vein of 6-week old C57 BL/KaLwRij mice (Harlen, Netherlands). Tumor was allowed to engraft for 10 days prior to the initiation of drug treatment. Four treatment groups were included: 1) Control animals; 2) MTI-101 (10 mg/kg) administered i.p. 3× weekly for three weeks (maximum tolerated dose); 3) Fc-Sec-His/MTI-101 conjugate (10 mg/kg) administered i.v. lx weekly for three weeks; 4) Fc-stop (10 mg/kg) administered i.v. lx weekly for three weeks; 5) equal payload of MTI-101 (0.3285 mg/kg) administered i.v. lx weekly for three weeks. Results are shown in FIG. 18A.

To quantify tumor burden, blood was collected by submandibular bleeding and mice were monitored weekly by measuring 5TGM1 secreted IgG2b (paraprotein) in the serum by ELISA (FIG. 18B). Hind limb paralysis and hunching were considered as additional surrogate markers for morbidity.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A carrying agent:cyclic compound adduct having the structure:

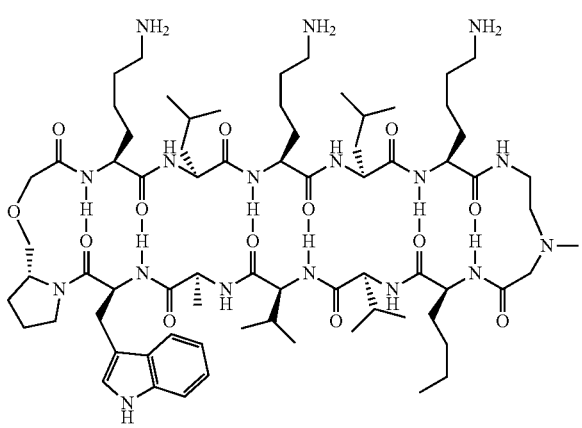

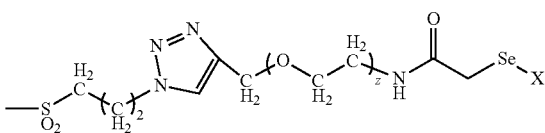

wherein X comprises a carrying agent and z is 1 to 20.

2. The carrying agent:cyclic compound adduct of claim 1, wherein said carrying agent comprises an amino acid, oligo (amino acid), poly(amino acid) or protein.

3. A composition comprising a cyclic compound of claim 2; and a pharmaceutically acceptable carrier.

* * * * *